US010927164B2

(12) United States Patent
Heywood et al.

(10) Patent No.: US 10,927,164 B2
(45) Date of Patent: Feb. 23, 2021

(54) METHOD FOR PROTEIN PURIFICATION

(71) Applicant: UCB BIOPHARMA SRL, Brussels (BE)

(72) Inventors: Sam Philip Heywood, Slough (GB); Gavin Barry Wild, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 106 days.

(21) Appl. No.: 15/566,231

(22) PCT Filed: Apr. 20, 2016

(86) PCT No.: PCT/EP2016/058774
§ 371 (c)(1),
(2) Date: Oct. 13, 2017

(87) PCT Pub. No.: WO2016/169992
PCT Pub. Date: Oct. 27, 2016

(65) Prior Publication Data

US 2018/0100007 A1 Apr. 12, 2018

(30) Foreign Application Priority Data

Apr. 22, 2015 (GB) ..................................... 1506868

(51) Int. Cl.
*C07K 16/06* (2006.01)
*C07K 1/22* (2006.01)
*C07K 16/18* (2006.01)
*C07K 16/28* (2006.01)

(52) U.S. Cl.
CPC .............. *C07K 16/065* (2013.01); *C07K 1/22* (2013.01); *C07K 16/18* (2013.01); *C07K 16/2878* (2013.01); *C07K 2317/31* (2013.01); *C07K 2317/55* (2013.01); *C07K 2317/62* (2013.01); *C07K 2317/622* (2013.01); *C07K 2317/624* (2013.01)

(58) Field of Classification Search
CPC .... C07K 16/065; C07K 1/22; C07K 2317/62; C07K 2317/31; C07K 2317/55; C07K 2317/622; C07K 2317/624
See application file for complete search history.

(56) References Cited

U.S. PATENT DOCUMENTS

| | | | | |
|---|---|---|---|---|
| 5,429,746 | A | 7/1995 | Shadle et al. | |
| 9,803,004 | B2 | 10/2017 | Adams et al. | |
| 2006/0257972 | A1* | 11/2006 | Ishihara | C07K 16/065 435/69.1 |
| 2013/0289247 | A1* | 10/2013 | Kremer | B01D 15/362 530/387.1 |
| 2014/0302033 | A1 | 10/2014 | Adams et al. | |
| 2015/0133640 | A1* | 5/2015 | Blein | C07K 16/2896 530/387.3 |
| 2018/0117153 | A1 | 5/2018 | Heywood et al. | |
| 2018/0142039 | A1 | 5/2018 | Heywood et al. | |

FOREIGN PATENT DOCUMENTS

| | | |
|---|---|---|
| WO | WO 00/69457 | 11/2000 |
| WO | WO 02/059264 | 8/2002 |
| WO | WO 2010/019493 | 2/2010 |
| WO | WO 2010/096418 | 8/2010 |
| WO | WO 2012/074463 | 6/2012 |
| WO | WO 2013/068563 | 5/2013 |
| WO | WO 2013/068571 | 5/2013 |
| WO | WO 2014/096390 | 6/2014 |
| WO | WO 2016/170137 | 10/2016 |
| WO | WO 2016/170138 | 10/2016 |

OTHER PUBLICATIONS

Fahrner et al. "Industrial Purification of Pharmaceutical antibodies: development, operation, and validation of chromatography processes" Biotechnology and Genetic Engineering Reviews, Jul. 18, 2001 (Year: 2001).*

Cunha, A. E. et al. "Methanol Induction Optimization for scFv Antibody Fragment Production in *Pichia pastoris" Biotechnology and Bioengineering*, May 20, 2004, pp. 458-467, vol. 86, No. 4.

Davies, J. et al. "'Camelising' human antibody fragments: NMR studies on VH domains" *FEBS Letters*, Feb. 21, 1994, pp. 285-290, vol. 339, No. 3.

Gargir, A. et al. "Single chain antibodies specific for fatty acids derived from a semi-synthetic phage display library" *Biochimica et Biophysica Acta*, Jan. 15, 2002, pp. 167-173, vol. 1569, Nos. 1-3.

Seldon, T. A. et al. "Improved Protein-A separation of $V_H3$ Fab from Fc after Papain Digestion of Antibodies" *Journal of Biomolecular Techniques*, Jul. 2011, pp. 50-52, vol. 22, No. 2.

Zhu, Z. et al. "High Level Secretion of a Humanized Bispecific Diabody from *Escherichia coli" Biotechnology*, Feb. 1996, pp. 192-196, vol. 14, No. 2.

Written Opinion in International Application No. PCT/EP2016/058774, dated Jul. 1, 2016, pp. 1-7.

Potter, K. N. et al. "Staphylococcal Protein A Binding to $V_{H3}$ Encoded Immunoglobulins" *Intern. Rev. Immunol.*, Sep. 3, 1996, pp. 291-308, vol. 14.

* cited by examiner

*Primary Examiner* — Daniel E Kolker
*Assistant Examiner* — James L Rogers
(74) *Attorney, Agent, or Firm* — Saliwanchik, Lloyd & Eisenschenk

(57) ABSTRACT

The present invention provides a method for recovering a human VH3 domain-containing antibody in monomeric form. In particular the present invention provides a new method that allows recovery of monomeric human VH3 domain-containing antibodies from a mixture containing monomeric and multimeric forms of the antibody.

15 Claims, 31 Drawing Sheets

Specification includes a Sequence Listing.

| Lane | Sample |
|---|---|
| 1 | Molecular Weight Markers (Novex Mk12) |
| 2 | MabSelect Load - Clarified Cell Culture Supernatant |
| 3 | MabSelect Flowthrough |
| 4 | Elution pH 3.8 |
| 5 | Elution pH 3.0 |

| Lane | Sample |
| --- | --- |
| 1 | Molecular Weight Markers (Novex Mk12) |
| 2 | MabSelect Load - Clarified Cell Culture Supernatant |
| 3 | MabSelect Flowthrough |
| 4 | Elution pH 3.8 |
| 5 | Elution pH 3.0 |

Fab = Heavy and Light Chain of Fab with a disulfide bond between the heavy and light chain and linkers joined to C-terminus of the constant region of the heavy chain and light chain to join to the dsFv dsFv = disulfide stabilised Fv and linkers to join to the Fab

Figure 13

(a) Light chain variable region of antibody A26 specific to OX40 (SEQ ID NO:7)

DIQMTQSPSSLSASVGDRVTITCRATQSIYNALAWYQQKPGKAPKLLIYNANTLHTGVPSRFSA
SGSGTDSTLTISSLQPEDFATYYCQQYYDYPLTFGGGTKVEIKR (b) Heavy chain variable region of antibody A26 specific to OX40 (SEQ ID NO:8)

EVQLVESGGGLVQPGGSLRLSCAASGFTFTNYGIHWIRQAPGKGLEWVASISPSGGLTYYRDSV
KGRFTISRDDAKNSPYLQMNSLRAEDTAVYYCATGGEGIFDYWGQGTLVTVSS (c)

CDRH1: NYGIH (SEQ ID NO:1)

CDRH2: SISPSGGLTYYRDSVKG (SEQ ID NO:2)

CDRH3: GGEGIFDY (SEQ ID NO:3)

CDRL1: RATQSIYNALA (SEQ ID NO:4)

CDRL2: NANTLHT (SEQ ID NO:5)

CDRL3: QQYYDYPLT (SEQ ID NO:6)

(d) Light chain of anti-OX40 antibody Fab component (SEQ ID NO:9)

DIQMTQSPSSLSASVGDRVTITCRATQSIYNALAWYQQKPGKAPKLLIYNANTLHTGVPSRFSA
SGSGTDSTLTISSLQPEDFATYYCQQYYDYPLTFGGGTKVEIKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGEC (e) Heavy chain of anti-OX40 antibody Fab component (SEQ ID NO:10)

EVQLVESGGGLVQPGGSLRLSCAASGFTFTNYGIHWIRQAPGKGLEWVASISPSGGLTYYRDSV
KGRFTISRDDAKNSPYLQMNSLRAEDTAVYYCATGGEGIFDYWGQGTLVTVSSASTKGPSVFPL
APSSKSTSGGTAALGCLVKDYFPEPVTVSWNSGALTSGVHTFPAVLQSSGLYSLSSVVTVPSSS
LGTQTYICNVNHKPSNTKVDKKVEPKSC

Figure 14

(a) Heavy chain of anti-albumin Fv component (SEQ ID NO:11)

EVQLLESGGGLVQPGGSLRLSCAVSGIDLSNYAINWVRQAPGKCLEWIGIIWASGTTFYATWAKGRFTISRDNSKNT
VYLQMNSLRAEDTAVYYCARTVPGYSTAPYFDLWGQGTLVTVSS (b) Light chain of anti-albumin Fv component (SEQ ID NO:12)

DIQMTQSPSSVSASVGDRVTITCQSSPSVWSNFLSWYQQKPGKAPKLLIYEASKLTSGVPSRFSGSGSGTDFTLTIS
SLQPEDFATYYCGGGYSSISDTTFGCGTKVEIKRT (c) Linker 1 (SEQ ID NO:13)

SGGGGSGGGGTGGGGS (d) Linker 2 (SEQ ID NO:14)

GGGGSGGGGSGGGGS (e) A26 Fab Heavy-(G4S,G4T,G4S)-645dsFv(gH5) (SEQ ID NO:15)

EVQLVESGGGLVQPGGSLRLSCAASGFTFTNYGIHWIRQAPGKGLEWVASISPSGGLTYYRDSVKGRFTISRDDAKN
SPYLQMNSLRAEDTAVYYCATGGEGIFDYWGQGTLVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDKKVEPKSCSGGGGSGGGGT
GGGGSEVQLLESGGGLVQPGGSLRLSCAVSGIDLSNYAINWVRQAPGKCLEWIGIIWASGTTFYATWAKGRFTISRD
NSKNTVYLQMNSLRAEDTAVYYCARTVPGYSTAPYFDLWGQGTLVTVSS (f) A26 Fab Light-(3xG4S)-645dsFv(gL4) (SEQ ID NO:16)

DIQMTQSPSSLSASVGDRVTITCRATQSIYNALAWYQQKPGKAPKLLIYNANTLHTGVPSRFSASGSGTDSTLTISS
LQPEDFATYYCQQYYDYPLTFGGGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGECGGGGSGGGGSGGGGSDI
QMTQSPSSVSASVGDRVTITCQSSPSVWSNFLSWYQQKPGKAPKLLIYEASKLTSGVPSRFSGSGSGTDFTLTISSL
QPEDFATYYCGGGYSSISDTTFGCGTKVEIKRT

Figure 15

(a) 645gH1 heavy chain variable domain (SEQ ID NO:17)

EVQLLESGGGLVQPGGSLRLSCAVSGIDLSNYAINWVRQAPGKCLEWIGIIWASGTTFYATWAKGRFTISRDSTTVY
LQMNSLRAEDTAVYYCARTVPGYSTAPYFDLWGQGTLVTVSS (b) 645gL1 light chain variable domain (SEQ ID NO:18)

DIVMTQSPSSVSASVGDRVTITCQSSPSVWSNFLSWYQQKPGKAPKLLIYEASKLTSGVPSRFKGSGSGTDFTLTIS
SLQPEDFATYYCGGGYSSISDTTFGCGTKVEIK (c) A26 Fab Heavy-( 3xG4S)-645dsFv(gH1) (SEQ ID NO:19)

EVQLVESGGGLVQPGGSLRLSCAASGFTFTNYGIHWIRQAPGKGLEWVASISPSGGLTYYRDSVKGRFTISRDDAKN
SPYLQMNSLRAEDTAVYYCATGGEGIFDYWGQGTLVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDKKVEPKSCSGGGGSGGGGS
GGGGSEVQLLESGGGLVQPGGSLRLSCAVSGIDLSNYAINWVRQAPGKCLEWIGIIWASGTTFYATWAKGRFTISRD
STTVYLQMNSLRAEDTAVYYCARTVPGYSTAPYFDLWGQGTLVTVSS (d) A26 Fab Light-(3xG4S)-645dsFv(gL1) (SEQ ID NO:20)

DIQMTQSPSSLSASVGDRVTITCRATQSIYNALAWYQQKPGKAPKLLIYNANTLHTGVPSRFSASGSGTDSTLTISS
LQPEDFATYYCQQYYDYPLTFGGGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGECSGGGGSGGGGSGGGGSD
IVMTQSPSSVSASVGDRVTITCQSSPSVWSNFLSWYQQKPGKAPKLLIYEASKLTSGVPSRFKGSGSGTDFTLTISS
LQPEDFATYYCGGGYSSISDTTFGCGTKVEIK

Figure 16 a) DNA encoding Heavy chain A26-645(gH5) including *E.coli* OmpA leader (SEQ ID NO:21)

ATGAAGAAGACTGCTATAGCGATCGCAGTGGCGCTAGCTGGTTTCGCCACCGTGGCGCAAGCTGAAGTTCAGCTGGT
CGAGTCTGGAGGCGGGCTTGTCCAGCCTGGAGGGAGCCTGCGTCTCTCTTGTGCAGCAAGCGGTTTCACGTTCACCA
ACTACGGTATCCACTGGATTCGTCAGGCACCAGGTAAAGGTCTGGAATGGGTAGCCTCTATCTCTCCGTCTGGTGGT
CTGACGTACTACCGTGACTCTGTCAAAGGTCGTTTCACCATCTCTCGTGATGACGCGAAAAACTCTCCGTACCTGCA
AATGAACTCTCTGCGTGCAGAAGATACCGCAGTGTACTACTGCGCTACTGGTGGTGAAGGTATCTTCGACTACTGGG
GTCAGGGTACCCTGGTAACTGTCTCGAGCGCTTCTACAAAGGGCCCAAGCGTTTTCCCACTGGCTCCGTCCTCTAAA
TCCACCTCTGGTGGTACGGCTGCACTGGGTTGCCTGGTGAAAGACTACTTCCCAGAACCAGTTACCGTGTCTTGGAA
CTCTGGTGCACTGACCTCTGGTGTTCACACCTTTCCAGCAGTTCTCCAGTCTTCTGGTCTGTACTCCCTGTCTAGCG
TGGTTACCGTTCCGTCTTCTTCTCTGGGTACTCAGACCTACATCTGCAACGTCAACCACAAACCGTCCAACACCAAG
GTCGACAAAAAAGTCGAGCCGAAATCCTGTAGTGGAGGTGGGGGCTCAGGTGGAGGCGGGACCGGTGGAGGTGGCAG
CGAGGTTCAACTGCTTGAGTCTGGAGGAGGCCTAGTCCAGCCTGGAGGGAGCCTGCGTCTCTCTTGTGCAGTAAGCG
GCATCGACCTGAGCAATTACGCCATCAACTGGGTGAGACAAGCTCCGGGGAAGTGTTTAGAATGGATCGGTATAATA
TGGGCCAGTGGGACGACCTTTTATGCTACATGGGCGAAAGGAAGGTTTACAATTAGCCGGGACAATAGCAAAAACAC
CGTGTATCTCCAAATGAACTCCTTGCGAGCAGAGGACACGGCGGTGTACTATTGTGCTCGCACTGTCCCAGGTTATA
GCACTGCACCCTACTTCGATCTGTGGGGACAAGGGACCCTGGTGACTGTTTCAAGTTAA b) DNA encoding Heavy chain A26-645(gH5) (SEQ ID NO:22)

GAAGTTCAGCTGGTCGAGTCTGGAGGCGGGCTTGTCCAGCCTGGAGGGAGCCTGCGTCTCTCTTGTGCAGCAAGCGG
TTTCACGTTCACCAACTACGGTATCCACTGGATTCGTCAGGCACCAGGTAAAGGTCTGGAATGGGTAGCCTCTATCT
CTCCGTCTGGTGGTCTGACGTACTACCGTGACTCTGTCAAAGGTCGTTTCACCATCTCTCGTGATGACGCGAAAAAC
TCTCCGTACCTGCAAATGAACTCTCTGCGTGCAGAAGATACCGCAGTGTACTACTGCGCTACTGGTGGTGAAGGTAT
CTTCGACTACTGGGGTCAGGGTACCCTGGTAACTGTCTCGAGCGCTTCTACAAAGGGCCCAAGCGTTTTCCCACTGG
CTCCGTCCTCTAAATCCACCTCTGGTGGTACGGCTGCACTGGGTTGCCTGGTGAAAGACTACTTCCCAGAACCAGTT
ACCGTGTCTTGGAACTCTGGTGCACTGACCTCTGGTGTTCACACCTTTCCAGCAGTTCTCCAGTCTTCTGGTCTGTA
CTCCCTGTCTAGCGTGGTTACCGTTCCGTCTTCTTCTCTGGGTACTCAGACCTACATCTGCAACGTCAACCACAAAC
CGTCCAACACCAAGGTCGACAAAAAAGTCGAGCCGAAATCCTGTAGTGGAGGTGGGGGCTCAGGTGGAGGCGGGACC
GGTGGAGGTGGCAGCGAGGTTCAACTGCTTGAGTCTGGAGGAGGCCTAGTCCAGCCTGGAGGGAGCCTGCGTCTCTC
TTGTGCAGTAAGCGGCATCGACCTGAGCAATTACGCCATCAACTGGGTGAGACAAGCTCCGGGGAAGTGTTTAGAAT
GGATCGGTATAATATGGGCCAGTGGGACGACCTTTTATGCTACATGGGCGAAAGGAAGGTTTACAATTAGCCGGGAC
AATAGCAAAAACACCGTGTATCTCCAAATGAACTCCTTGCGAGCAGAGGACACGGCGGTGTACTATTGTGCTCGCAC
TGTCCCAGGTTATAGCACTGCACCCTACTTCGATCTGTGGGGACAAGGGACCCTGGTGACTGTTTCAAGTTAA

Figure 17 a) DNA encoding Light chain A26-645(gL4) including E.coli OmpA leader (SEQ ID NO:23)

ATGAAAAAGACAGCTATCGCAATTGCAGTGGCGTTGGCTGGTTTCGCGACCGTTGCGCAAGCTGATATCCAGATGAC
CCAGAGCCCAAGCAGTCTCTCCGCCAGCGTAGGCGATCGTGTGACTATTACCTGTCGTGCAACCCAGAGCATCTACA
ACGCTCTGGCTTGGTATCAGCAGAAACCGGGTAAAGCGCCAAAACTCCTGATCTACAACGCGAACACTCTGCATACT
GGTGTTCCGTCTCGTTTCTCTGCGTCTGGTTCTGGTACGGACTCTACTCTGACCATCTCCTCTCTCCAGCCGGAAGA
TTTCGCGACCTACTACTGCCAGCAGTACTACGATTACCCACTGACGTTTGGTGGTGGTACCAAAGTTGAGATCAAAC
GTACGGTTGCAGCTCCATCCGTCTTCATCTTTCCACCGTCTGACGAACAGCTCAAATCTGGTACTGCTTCTGTCGTT
TGCCTCCTGAACAACTTCTATCCGCGTGAAGCGAAAGTCCAGTGGAAAGTCGACAACGCACTCCAGTCTGGTAACTC
TCAGGAATCTGTGACCGAACAGGACTCCAAAGACTCCACCTACTCTCTGTCTAGCACCCTGACTCTGTCCAAAGCAG
ACTACGAGAAACACAAAGTGTACGCTTGCGAAGTTACCCATCAGGGTCTGAGCTCTCCGGTTACCAAATCCTTTAAT
AGAGGGGAGTGTGGTGGCGGTGGCAGTGGTGGTGGAGGTTCCGGAGGTGGCGGTTCAGACATACAAATGACCCAGAG
TCCTTCATCGGTATCCGCGTCCGTTGGCGATAGGGTGACTATTACATGTCAAAGCTCTCCTAGCGTCTGGAGCAATT
TTCTATCCTGGTATCAACAGAAACCGGGGAAGGCTCCAAAACTTCTGATTTATGAAGCCTCGAAACTCACCAGTGGA
GTTCCGTCAAGATTCAGTGGCTCTGGATCAGGGACAGACTTCACGTTGACAATCAGTTCGCTGCAACCAGAGGACTT
TGCGACCTACTATTGTGGTGGAGGTTACAGTAGCATAAGTGATACGACATTTGGGTGCGGTACTAAGGTGGAAATCA
AACGTACCTAA b) DNA encoding Light chain A26-645(gL4) (SEQ ID NO:24)

GATATCCAGATGACCCAGAGCCCAAGCAGTCTCTCCGCCAGCGTAGGCGATCGTGTGACTATTACCTGTCGTGCAAC
CCAGAGCATCTACAACGCTCTGGCTTGGTATCAGCAGAAACCGGGTAAAGCGCCAAAACTCCTGATCTACAACGCGA
ACACTCTGCATACTGGTGTTCCGTCTCGTTTCTCTGCGTCTGGTTCTGGTACGGACTCTACTCTGACCATCTCCTCT
CTCCAGCCGGAAGATTTCGCGACCTACTACTGCCAGCAGTACTACGATTACCCACTGACGTTTGGTGGTGGTACCAA
AGTTGAGATCAAACGTACGGTTGCAGCTCCATCCGTCTTCATCTTTCCACCGTCTGACGAACAGCTCAAATCTGGTA
CTGCTTCTGTCGTTTGCCTCCTGAACAACTTCTATCCGCGTGAAGCGAAAGTCCAGTGGAAAGTCGACAACGCACTC
CAGTCTGGTAACTCTCAGGAATCTGTGACCGAACAGGACTCCAAAGACTCCACCTACTCTCTGTCTAGCACCCTGAC
TCTGTCCAAAGCAGACTACGAGAAACACAAAGTGTACGCTTGCGAAGTTACCCATCAGGGTCTGAGCTCTCCGGTTA
CCAAATCCTTTAATAGAGGGGAGTGTGGTGGCGGTGGCAGTGGTGGTGGAGGTTCCGGAGGTGGCGGTTCAGACATA
CAAATGACCCAGAGTCCTTCATCGGTATCCGCGTCCGTTGGCGATAGGGTGACTATTACATGTCAAAGCTCTCCTAG
CGTCTGGAGCAATTTTCTATCCTGGTATCAACAGAAACCGGGGAAGGCTCCAAAACTTCTGATTTATGAAGCCTCGA
AACTCACCAGTGGAGTTCCGTCAAGATTCAGTGGCTCTGGATCAGGGACAGACTTCACGTTGACAATCAGTTCGCTG
CAACCAGAGGACTTTGCGACCTACTATTGTGGTGGAGGTTACAGTAGCATAAGTGATACGACATTTGGGTGCGGTAC
TAAGGTGGAAATCAAACGTACCTAA

Figure 18 a) DNA encoding Heavy chain A26-645(gH5) including B72.3 leader sequence (SEQ ID NO:25)

ATGGAATGGTCCTGGGTCTTCCTGTTTTTCCTTTCTGTCACAACCGGGGTGCACAGCGAGGTGCAGCTCGTCGAGTC
TGGAGGCGGGCTTGTCCAGCCTGGAGGGAGCCTGCGTCTCTCTTGTGCAGCAAGCGGTTTCACGTTCACCAACTACG
GTATCCACTGGATTCGTCAGGCACCAGGTAAAGGTCTGGAATGGGTAGCCTCTATCTCTCCGTCTGGTGGTCTGACG
TACTACCGTGACTCTGTCAAAGGTCGTTTCACCATCTCTCGTGATGACGCGAAAAACTCTCCGTACCTGCAGATGAA
CTCTCTGCGTGCAGAAGATACCGCAGTGTACTACTGCGCTACTGGTGGTGAAGGTATCTTCGACTACTGGGGTCAGG
GTACCCTGGTAACTGTCTCAAGCGCTTCTACAAAGGGCCCATCGGTCTTCCCCCTGGCACCCTCCTCCAAGAGCACC
TCTGGGGGCACAGCGGCCCTGGGCTGCCTGGTCAAGGACTACTTCCCCGAACCGGTGACGGTGTCGTGGAACTCAGG
CGCCCTGACCAGCGGCGTGCACACCTTCCCGGCTGTCCTACAGTCCTCTGGACTCTACTCCCTCAGCAGCGTGGTGA
CCGTGCCCTCCAGCAGCTTGGGCACCCAGACCTACATCTGCAACGTGAATCACAAGCCCAGCAACACCAAGGTGGAC
AAGAAAGTTGAGCCCAAATCTTGTTCCGGAGGTGGCGGTTCCGGAGGTGGCGGTACCGGTGGCGGTGGATCCGAAGT
CCAGCTGCTTGAATCCGGAGGCGGACTCGTGCAGCCCGGAGGCAGTCTTCGCTTGTCCTGCGCTGTATCTGGAATCG
ACCTGAGCAATTACGCCATCAACTGGGTGAGACAGGCACCTGGGAAATGCCTCGAATGGATCGGCATTATATGGGCT
AGTGGGACGACCTTTTATGCTACATGGGCGAAGGGTAGATTCACAATCTCACGGGATAATAGTAAGAACACAGTGTA
CCTGCAGATGAACTCCCTGCGAGCAGAGGATACCGCCGTTTACTATTGTGCTCGCACTGTCCCAGGTTATAGCACTG
CACCCTACTTTGATCTGTGGGGGCAGGGCACTCTGGTCACCGTCTCGAGTTGA b) DNA encoding Heavy chain A26-645(gH5) (SEQ ID NO:26)

GAGGTGCAGCTCGTCGAGTCTGGAGGCGGGCTTGTCCAGCCTGGAGGGAGCCTGCGTCTCTCTTGTGCAGCAAGCGG
TTTCACGTTCACCAACTACGGTATCCACTGGATTCGTCAGGCACCAGGTAAAGGTCTGGAATGGGTAGCCTCTATCT
CTCCGTCTGGTGGTCTGACGTACTACCGTGACTCTGTCAAAGGTCGTTTCACCATCTCTCGTGATGACGCGAAAAAC
TCTCCGTACCTGCAGATGAACTCTCTGCGTGCAGAAGATACCGCAGTGTACTACTGCGCTACTGGTGGTGAAGGTAT
CTTCGACTACTGGGGTCAGGGTACCCTGGTAACTGTCTCAAGCGCTTCTACAAAGGGCCCATCGGTCTTCCCCCTGG
CACCCTCCTCCAAGAGCACCTCTGGGGGCACAGCGGCCCTGGGCTGCCTGGTCAAGGACTACTTCCCCGAACCGGTG
ACGGTGTCGTGGAACTCAGGCGCCCTGACCAGCGGCGTGCACACCTTCCCGGCTGTCCTACAGTCCTCTGGACTCTA
CTCCCTCAGCAGCGTGGTGACCGTGCCCTCCAGCAGCTTGGGCACCCAGACCTACATCTGCAACGTGAATCACAAGC
CCAGCAACACCAAGGTGGACAAGAAAGTTGAGCCCAAATCTTGTTCCGGAGGTGGCGGTTCCGGAGGTGGCGGTACC
GGTGGCGGTGGATCCGAAGTCCAGCTGCTTGAATCCGGAGGCGGACTCGTGCAGCCCGGAGGCAGTCTTCGCTTGTC
CTGCGCTGTATCTGGAATCGACCTGAGCAATTACGCCATCAACTGGGTGAGACAGGCACCTGGGAAATGCCTCGAAT
GGATCGGCATTATATGGGCTAGTGGGACGACCTTTTATGCTACATGGGCGAAGGGTAGATTCACAATCTCACGGGAT
AATAGTAAGAACACAGTGTACCTGCAGATGAACTCCCTGCGAGCAGAGGATACCGCCGTTTACTATTGTGCTCGCAC
TGTCCCAGGTTATAGCACTGCACCCTACTTTGATCTGTGGGGGCAGGGCACTCTGGTCACCGTCTCGAGTTGA

Figure 19 a) DNA encoding Light chain A26-645(gL4) including B72.3 leader sequence (SEQ ID NO:27)

ATGTCAGTTCCCACACAGGTGCTGGGCCTGCTTCTGTTGTGGCTCACCGATGCTAGGTGTGATATCCAGATGACCCA
GAGTCCAAGCAGTCTCTCCGCCAGCGTAGGCGATCGTGTGACTATTACCTGTCGTGCAACCCAGAGCATCTACAACG
CTCTGGCTTGGTATCAGCAGAAACCGGGTAAAGCGCCAAAACTCCTGATCTACAACGCGAACACTCTGCATACCGGT
GTTCCGTCTCGTTTCTCTGCGTCTGGTTCTGGTACGGACTCTACTCTGACCATCTCCTCTCTGCAGCCGGAAGATTT
CGCGACCTACTACTGCCAGCAGTACTACGATTACCCACTGACGTTTGGTGGTGGTACCAAAGTTGAGATCAAACGTA
CGGTGGCTGCACCATCTGTCTTCATCTTCCCCCCATCTGATGAGCAGTTGAAGTCTGGCACTGCCTCTGTTGTGTGC
CTGCTGAATAACTTCTACCCTAGAGAGGCCAAAGTCCAGTGGAAGGTGGATAACGCCCTTCAATCCGGAAACTCCCA
GGAGAGTGTCACTGAGCAGGACTCAAAGGACTCCACCTATAGCCTTAGCAGCACACTGACACTGAGCAAGGCTGACT
ACGAGAAACACAAGGTCTACGCCTGCGAAGTGACACATCAAGGCCTGAGCTCACCCGTGACAAAGAGCTTTAACAGG
GGAGAGTGTGGTGGAGGTGGCTCTGGCGGTGGTGGCTCCGGAGGCGGAGGAAGCGACATCCAGATGACCCAGAGCCC
TTCCTCTGTAAGCGCCAGTGTCGGAGACAGAGTGACTATTACCTGCCAAAGCTCCCCTTCAGTCTGGTCCAATTTTC
TATCCTGGTACCAGCAAAAGCCCGGAAAGGCTCCTAAATTGCTGATCTACGAAGCAAGCAAACTCACCAGCGGCGTG
CCCAGCAGGTTCAGCGGCAGTGGGTCTGGAACTGACTTTACCCTGACAATCTCCTCACTCCAGCCCGAGGACTTCGC
CACCTATTACTGCGGTGGAGGTTACAGTAGCATAAGTGATACGACATTTGGATGCGGCACTAAAGTGGAAATCAAGC
GTACCTGA b) DNA encoding Light chain A26-645(gL4) (SEQ ID NO:28)

GATATCCAGATGACCCAGAGTCCAAGCAGTCTCTCCGCCAGCGTAGGCGATCGTGTGACTATTACCTGTCGTGCAAC
CCAGAGCATCTACAACGCTCTGGCTTGGTATCAGCAGAAACCGGGTAAAGCGCCAAAACTCCTGATCTACAACGCGA
ACACTCTGCATACCGGTGTTCCGTCTCGTTTCTCTGCGTCTGGTTCTGGTACGGACTCTACTCTGACCATCTCCTCT
CTGCAGCCGGAAGATTTCGCGACCTACTACTGCCAGCAGTACTACGATTACCCACTGACGTTTGGTGGTGGTACCAA
AGTTGAGATCAAACGTACGGTGGCTGCACCATCTGTCTTCATCTTCCCCCCATCTGATGAGCAGTTGAAGTCTGGCA
CTGCCTCTGTTGTGTGCCTGCTGAATAACTTCTACCCTAGAGAGGCCAAAGTCCAGTGGAAGGTGGATAACGCCCTT
CAATCCGGAAACTCCCAGGAGAGTGTCACTGAGCAGGACTCAAAGGACTCCACCTATAGCCTTAGCAGCACACTGAC
ACTGAGCAAGGCTGACTACGAGAAACACAAGGTCTACGCCTGCGAAGTGACACATCAAGGCCTGAGCTCACCCGTGA
CAAAGAGCTTTAACAGGGGAGAGTGTGGTGGAGGTGGCTCTGGCGGTGGTGGCTCCGGAGGCGGAGGAAGCGACATC
CAGATGACCCAGAGCCCTTCCTCTGTAAGCGCCAGTGTCGGAGACAGAGTGACTATTACCTGCCAAAGCTCCCCTTC
AGTCTGGTCCAATTTTCTATCCTGGTACCAGCAAAAGCCCGGAAAGGCTCCTAAATTGCTGATCTACGAAGCAAGCA
AACTCACCAGCGGCGTGCCCAGCAGGTTCAGCGGCAGTGGGTCTGGAACTGACTTTACCCTGACAATCTCCTCACTC
CAGCCCGAGGACTTCGCCACCTATTACTGCGGTGGAGGTTACAGTAGCATAAGTGATACGACATTTGGATGCGGCAC
TAAAGTGGAAATCAAGCGTACCTGA

FIGURE 20 a

(a) Heavy chain variable domain of anti-albumin antibody (no ds) (SEQ ID NO:29)

EVQLLESGGGLVQPGGSLRLSCAVSGIDLSNYAINWVRQAPGKGLEWIGIIWASGTTFYATWAKGRFTISRDNSKNT
VYLQMNSLRAEDTAVYYCARTVPGYSTAPYFDLWGQGTLVTVSS (b) Heavy chain variable domain of anti-albumin antibody (ds) (SEQ ID NO:30)

EVQLLESGGGLVQPGGSLRLSCAVSGIDLSNYAINWVRQAPGKCLEWIGIIWASGTTFYATWAKGRFTISRDNSKNT
VYLQMNSLRAEDTAVYYCARTVPGYSTAPYFDLWGQGTLVTVSS (c) Light chain variable domain of anti-albumin antibody (no ds) (SEQ ID NO:31)

DIQMTQSPSSVSASVGDRVTITCQSSPSVWSNFLSWYQQKPGKAPKLLIYEASKLTSGVPSRFSGSGSGTDFTLTIS
SLQPEDFATYYCGGGYSSISDTTFGGGTKVEIKRT (d) Light chain variable domain of anti-albumin antibody (ds) (SEQ ID NO:32)

DIQMTQSPSSVSASVGDRVTITCQSSPSVWSNFLSWYQQKPGKAPKLLIYEASKLTSGVPSRFSGSGSGTDFTLTIS
SLQPEDFATYYCGGGYSSISDTTFGCGTKVEIKRT (e) Linker 1 (SEQ ID NO:33) SGGGGSGGGGTGGGGS
(f) Linker 2 (SEQ ID NO:34) GGGGSGGGGSGGGGS 645 gH5gL4 specific to albumin (SEQ ID NO: 35)

GAGGTTCAGCTGCTGGAGTCTGGAGGCGGGCTTGTCCAGCCTGGAGGGAGCCTGCGTCTCTCTTGTGCAGTAAGCGG
CATCGACCTGTCCAACTACGCGATTAACTGGGTACGTCAGGCACCGGGTAAAGGTCTGGAATGGATCGGCATCATCT
GGGCCTCTGGTACGACCTTCTACGCTACTTGGGCCAAAGGTCGTTTCACCATCTCCCGTGACAACTCTAAAAACACC
GTGTACCTGCAGATGAACTCTCTGCGTGCGGAAGACACTGCGGTTTACTATTGCGCGCGTACCGTTCCGGGCTATTC
TACTGCACCGTACTTCGACCTGTGGGGTCAGGGTACTCTGGTTACCGTCTCGAGTGGAGGTGGCGGTTCTGGCGGTG
GCGGTTCCGGTGGCGGTGGATCGGGAGGTGGCGGTTCTGATATCCAGATGACCCAGAGTCCAAGCAGTGTTTCCGCC
AGCGTAGGCGATCGTGTGACTATTACCTGTCAGTCCTCTCCGAGCGTTTGGTCCAACTTCCTGAGCTGGTACCAGCA
GAAACCGGGTAAAGCCCCGAAACTGCTGATCTACGAGGCGTCTAAACTGACCTCTGGTGTACCGTCCCGTTTCTCTG
GCTCTGGCTCTGGTACGGACTTCACTCTGACCATCTCCTCTCTGCAGCCGGAAGACTTTGCAACGTACTACTGCGGT
GGTGGTTACTCTTCCATCTCTGACACCACGTTCGGTGGAGGCACCAAAGTTGAAATCAAACGTACGCATCACCATCA
CCATCACCATCACCATCAC 645 gH5gL4 specific to albumin (SEQ ID NO: 36)

EVQLLESGGGLVQPGGSLRLSCAVSGIDLSNYAINWVRQAPGKGLEWIGIIWASGTTFYATWAKGRFTISRDNSKNT
VYLQMNSLRAEDTAVYYCARTVPGYSTAPYFDLWGQGTLVTVSSGGGGSGGGGSGGGGSGGGGSDIQMTQSPSSVSA
SVGDRVTITCQSSPSVWSNFLSWYQQKPGKAPKLLIYEASKLTSGVPSRFSGSGSGTDFTLTISSLQPEDFATYYCG
GGYSSISDTTFGGGTKVEIKRTHHHHHHHHHH

Figure 20 b

645 gH5gL4ds specific to albumin (SEQ ID NO: 37)

GAGGTTCAGCTGCTGGAGTCTGGAGGCGGGCTTGTCCAGCCTGGAGGGAGCCTGCGTCTCTCTTGTGCAGTAAGCGG
CATCGACCTGTCCAACTACGCGATTAACTGGGTACGTCAGGCACCGGGTAAATGCCTGGAATGGATCGGCATCATCT
GGGCCTCTGGTACGACCTTCTACGCTACTTGGGCCAAAGGTCGTTTCACCATCTCCCGTGACAACTCTAAAAACACC
GTGTACCTGCAGATGAACTCTCTGCGTGCGGAAGACACTGCGGTTTACTATTGCGCGCGTACCGTTCCGGGCTATTC
TACTGCACCGTACTTCGACCTGTGGGGTCAGGGTACTCTGGTTACCGTCTCGAGTGGAGGTGGCGGTTCTGGCGGTG
GCGGTTCCGGTGGCGGTGGATCGGGAGGTGGCGGTTCTGATATCCAGATGACCCAGAGTCCAAGCAGTGTTTCCGCC
AGCGTAGGCGATCGTGTGACTATTACCTGTCAGTCCTCTCCGAGCGTTTGGTCCAACTTCCTGAGCTGGTACCAGCA
GAAACCGGGTAAAGCCCCGAAACTGCTGATCTACGAGGCGTCTAAACTGACCTCTGGTGTACCGTCCCGTTTCTCTG
GCTCTGGCTCTGGTACGGACTTCACTCTGACCATCTCCTCTCTGCAGCCGGAAGACTTTGCAACGTACTACTGCGGT
GGTGGTTACTCTTCCATCTCTGACACCACGTTCGGTTGTGGCACCAAAGTTGAAATCAAACGTACGCATCACCATCA
CCATCACCATCACCATCAC 645 gH5gL4ds specific to albumin (SEQ ID NO: 38)

EVQLLESGGGLVQPGGSLRLSCAVSGIDLSNYAINWVRQAPGKCLEWIGIIWASGTTFYATWAKGRFTISRDNSKNT
VYLQMNSLRAEDTAVYYCARTVPGYSTAPYFDLWGQGTLVTVSSGGGGSGGGGSGGGGSGGGGSDIQMTQSPSSVSA
SVGDRVTITCQSSPSVWSNFLSWYQQKPGKAPKLLIYEASKLTSGVPSRFSGSGSGTDFTLTISSLQPEDFATYYCG
GGYSSISDTTFGCGTKVEIKRTHHHHHHHHHH

| Lane | Sample |
| --- | --- |
| 1 | Molecular Weight Markers (Novex Mk12 |
| 2 | Fraction 1 |
| 3 | Fraction 2 |
| 4 | Fraction 3 |

Figure 27

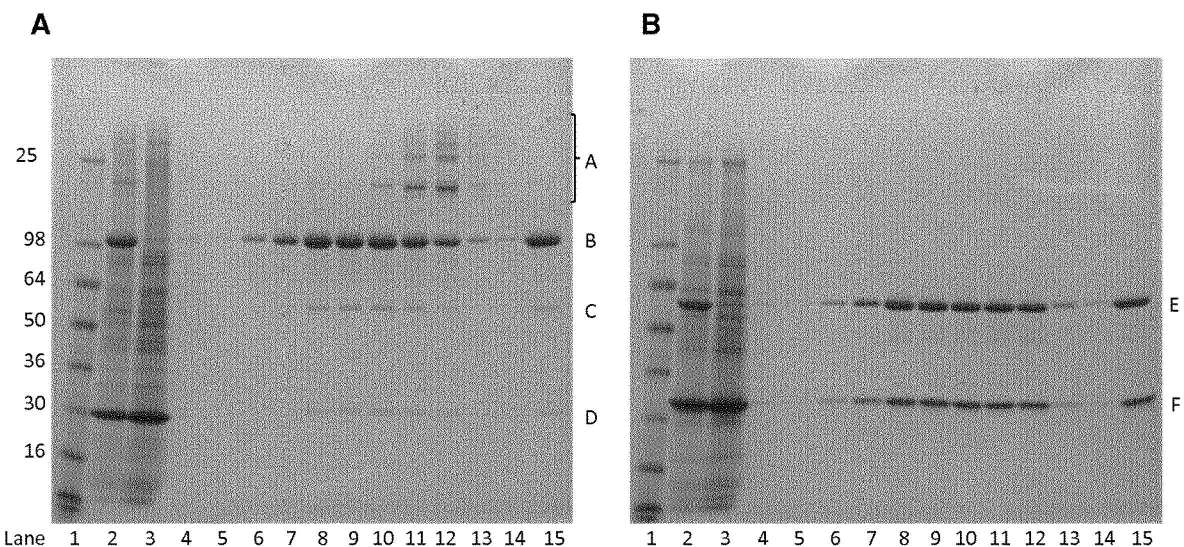

Key:

| | |
|---|---|
| A: | BYbe Multimer |
| B: | BYbe Monomer |
| C: | Non-disulphide bonded Heavy chain |
| D: | Non-disulphide bonded Light chain |
| E: | Reduced Heavy chain |
| F: | Reduced Light chain |

| Lane: | | |
|---|---|---|
| | 1 | Molecular Weight Marker (See Blue) |
| | 2 | MabSelect Load (clarified culture supernatant) |
| | 3 | MabSelect Flowthrough (F3) |
| | 4 | PBS Wash (F4) |
| | 5 | Phosphate/citrate Wash (F5) |
| | 6 | Fraction B9 |
| | 7 | Fraction B8 |
| | 8 | Fraction B7 |
| | 9 | Fraction B6 |
| | 10 | Fraction B5 |
| | 11 | Fraction B4 |
| | 12 | Fraction B3 |
| | 13 | Fraction B2 |
| | 14 | Fraction B1 |
| | 15 | Reference Standard (Protein G & S200 purified BYbe) |

Figure 30
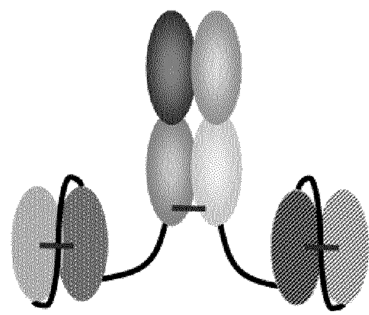
Fab#2-(HC)-dsscFv#3-(LC)-dsscFv#4
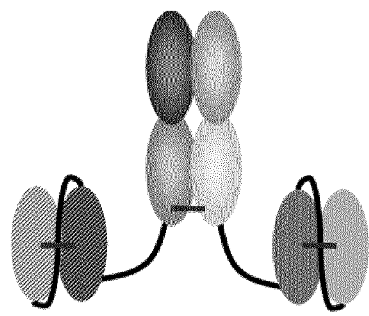
Fab#2-(LC)-dsscFv#3-(HC)-dsscFv#4
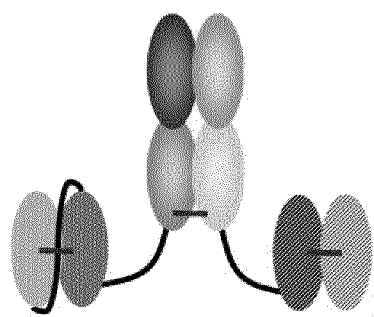
Fab-(HC)dsscFv-(LC)dsFv
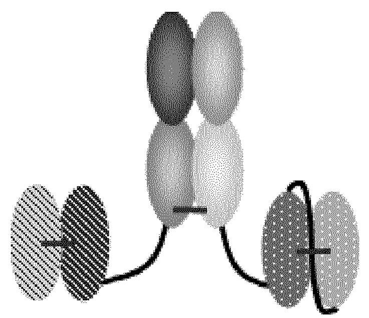
Fab-(HC)dsFv-(LC)dsscFv

METHOD FOR PROTEIN PURIFICATION

CROSS-REFERENCE TO RELATED APPLICATION

This application is the U.S. national stage application of International Patent Application No. PCT/EP2016/058774, filed Apr. 20, 2016.

The Sequence Listing for this application is labeled "Seq-List.txt" which was created on Oct. 2, 2017 and is 60 KB. The entire content of the sequence listing is incorporated herein by reference in its entirety.

FIELD OF THE INVENTION

The current invention is in the field of protein purification, more particularly in the field of antibody purification.

BACKGROUND OF THE INVENTION

In the field of therapeutics the use of proteins and antibodies and antibody-derived molecules in particular has been constantly gaining presence and importance, and, consequently, the need for controlled manufacturing processes has developed in parallel. The commercialization of therapeutic proteins, requires they be produced in large amounts. For this purpose the protein is frequently expressed in a host cell and must subsequently be recovered and purified, prior to its preparation into an administrable form.

The most common class of antibody molecule is immunoglobulin G (IgG), a heterotetramer composed of two heavy chains and two light chains. The IgG molecule can be subdivided into two functional subunits: (1) the fragment crystallizable (Fc), which constitutes the tail of the antibody and interacts with cell surface receptors to activate an immune response, and (2) the fragment antigen-binding (Fab), which mediates antigen recognition. The Fc region comprises two pairs of constant domains (CH2 and CH3) from two paired heavy chains, whereas the Fab region consists of a variable domain followed by a constant domain from the heavy chain (VH and CH1, respectively), which pair with a variable and constant domain from the light chain (VL and CL, respectively). The Fc and Fab regions are demarcated by a hinge region, which contains disulfide linkages holding the two chains together. Full-length antibodies of the IgG class have traditionally been purified using methods that include a capture step of affinity chromatography using protein A derived from *Staphylococcus aureus*. The high-specificity of binding between Protein A and the Fc-region of antibodies enables this mode of chromatography to remove more than 98% of the impurities in a single step starting directly from complex solutions such as cell culture harvest media. The large purification factor obtained from this process step helps to simplify the entire downstream purification process. In general, only trace contaminants (high molecular weight aggregates, residual host cell proteins, leached protein A) remain to be removed after this purification step and this can usually be achieved in one to two subsequent chromatographic steps.

Additionally an "alternate binding" site for binding protein A has been described in antibodies that contain the specific framework subgroup 3 of the human heavy chain variable region Sasso et al. J. Immunol 1991, 147:1877-1883, *Human IgA and IgG F(ab')2 that bind to staphylococcal protein A belong to the VHIII subgroup*), also referred to as the variable heavy chain domain VH3, and has often been classified as a secondary interaction. While all five domains of Protein A (A, B, C, D, E) bind IgG via their Fc-region, only domains D and E exhibit significant VH3 binding. In the context of IgG purification using protein A affinity chromatography, that is based on the interaction between the Fc domain of the IgG and the protein A, these VH3 domain interactions with Protein A have been considered undesirable given that they affect the elution profile of the antibody to be purified, and alternative resins have been developed and are available on the market that contain only domain B of Protein A such as SuRe® from GE Healthcare.

However, many of the antibodies and antibody-derived molecules currently available and/or in development don't contain Fc regions and require further tailoring of their purification methods. The above described binding of protein A by VH3 regions could enable the use of protein A in the manufacture of such antibodies.

A particular requirement of antibody purification is the recovery of the desired antibody or antibody-derived molecule in monomeric form, or essentially free from higher molecular weight species such as dimers and trimers.

Certain antibody molecules have a higher tendency to form multimers that result from variable domain promiscuous pairing with variable domains in adjacent molecules. This is particularly the case with more complex antibody derived molecules that use linker regions between different domains of interest.

Therefore there remains a need in the art for further methods of manufacturing and purifying antibodies and antibody-derived molecules in monomeric form, particularly where these molecules don't contain an Fc region.

BRIEF DESCRIPTION OF THE FIGURES

FIGS. 13 to 20 show various antibody molecule sequences and components thereof.

FIG. 27 shows a non-reducing (A) and reducing (B) SDS PAGE analysis of fractions recovered from the protein A chromatography of BYbe via a pH gradient elution depicted in FIG. 25.

FIG. 30 shows a schematic of alternative monomeric Fab-2x dsscFv (TrYbe®) and Fab-dsscFv-dsFv formats susceptible to purification according to the method of the invention.

DETAILED DESCRIPTION OF THE INVENTION

Figure 1:
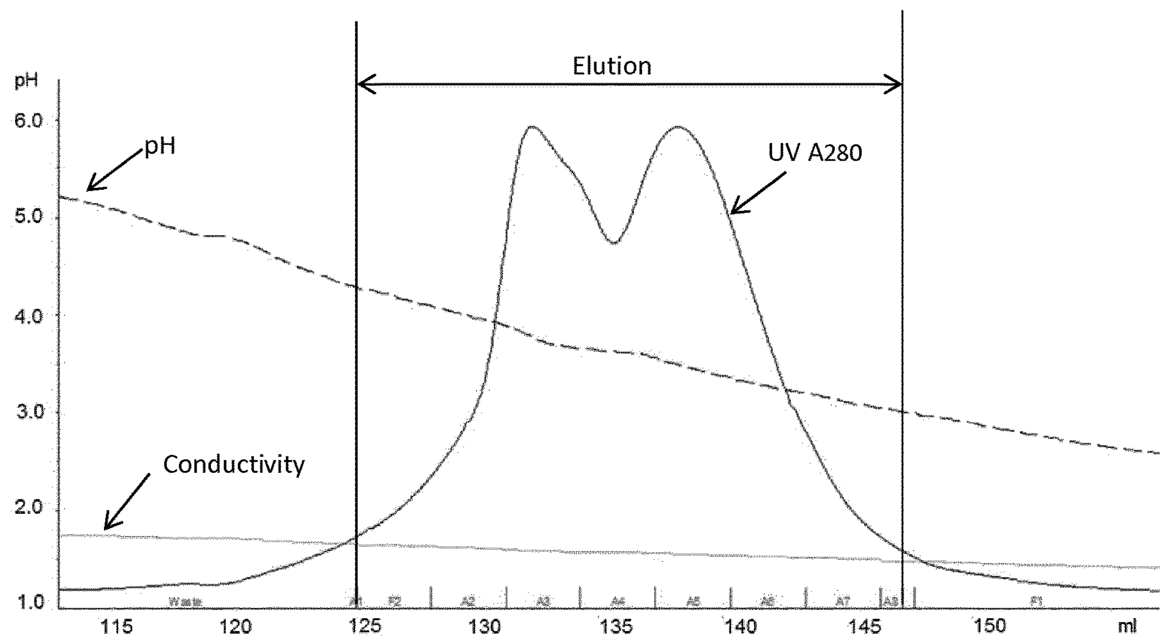
FIG. 1 is a chromatogram showing the elution profile of A26Fab-645dsFv from a Protein A resin via a pH gradient elution.

The present invention solves the above-identified need by providing a new method for recovering a human VH3 domain-containing antibody in monomeric form. An avidity effect has now been observed between the binding of human VH3 domains and protein A. This finding is surprising given that it has not been described for the interaction between Fc regions and protein A and has led to the development of a new method that allows recovery of monomeric human VH3 domain-containing antibodies from a mixture containing monomeric and multimeric forms of the antibody.

In a first embodiment, the present invention refers to a method for obtaining a human VH3 domain-containing antibody in monomeric form, comprising:

a) applying a mixture comprising a human VH3 domain-containing antibody in monomeric and multimeric form to a protein A chromatography material wherein said protein A comprises domain D and/or E, under conditions that allow binding of said antibody to protein A, and b) recovering the human VH3 domain containing-antibody in monomeric form, wherein the human VH3 domain containing antibody does not contain an Fc region.

In a second alternative embodiment, the present invention refers to a method for manufacturing a human VH3 domain-containing antibody comprising:

a) expressing the antibody in a host cell, b) recovering a mixture containing the antibody, host cells and other contaminants, c) purifying the antibody using at least a protein A chromatography step wherein said protein A comprises domain D and/or E, and d) recovering the human VH3 domain-containing antibody, wherein the human VH3 domain containing antibody does not contain an Fc region.

In a third alternative embodiment, the invention refers to a method of separating a human VH3 domain-containing antibody in monomeric form from the antibody in multimeric form comprising:

a) applying a mixture comprising a human VH3 domain-containing antibody in monomeric and multimeric form to a protein A chromatography material wherein said protein A comprises domain D and/or E, b) allowing binding of said antibody to protein A, c) applying an elution buffer that selectively disrupts binding of the antibody in monomeric form, d) recovering the resulting eluate, and optionally e) applying a second elution buffer that disrupts binding of the antibody in multimeric form and recovering this second eluate, wherein the human VH3 domain-containing antibody does not contain an Fc region.

In a fourth alternative embodiment, the invention refers to a method of separating a human VH3 domain-containing antibody in monomeric form from the antibody in multimeric form comprising:

a) applying a mixture comprising a human VH3 domain-containing antibody in monomeric and multimeric form to a protein A chromatography material wherein said protein A comprises domain D and/or E, b) allowing binding of the antibody in multimeric form, c) recovering the antibody in monomeric form in the flow-through, and optionally d) applying an elution buffer that selectively disrupts binding of the antibody in multimeric form, and e) recovering the eluate resulting from d);

wherein the human VH3 domain-containing antibody does not contain an Fc region.

In a further embodiment the method of the invention will additionally comprise another one or more chromatography steps to remove remaining impurities. Generally such steps will employ a non-affinity chromatography step using a solid phase with appropriate functionality for use in gel filtration chromatography, cation chromatography, anion chromatography, mixed mode chromatography, hydrophobic chromatography and hydrophobic charge induction chromatography. These may be operated in bind and elute mode or in flow through mode. In flow-through mode, the impurities bind or have reduced mobility in the solid phase whereas the target protein is recovered in the eluate or flow through fraction. Appropriate solid phases for use in chromatography such as beaded resins or membranes with the appropriate functionality are readily available to the skilled artisan. In a particular embodiment according to the method of the invention, the method additionally comprises a step of anion exchange chromatography operated in the flow through mode.

In a further particular embodiment the method of the invention comprises a protein A chromatography step followed by a first chromatography step that is an anion exchange chromatography producing a flow-through containing the protein and a second chromatography step that is a cation exchange chromatography from where an eluate containing the protein is recovered.

Alternatively, the method of the invention comprises a protein A chromatography followed by a first chromatography step that is a cation exchange chromatography from where an eluate containing the protein is recovered, and a second chromatography step that is an anion exchange chromatography to produce a flow-through containing the protein.

Typically, protein A chromatography is performed in bind and elute mode, wherein binding of the protein of interest to the solid phase allows the impurities such as contaminating proteins to flow through the chromatographic medium while the protein of interest remains bound to the solid phase. The bound protein of interest is then recovered from the solid phase with an elution buffer that disrupts the mechanism by which the protein of interest is bound to said solid phase.

In a further embodiment the method of the invention comprises a first solution is added to the protein A chromatography material after applying the mixture comprising the human VH3 domain-containing antibody in monomeric and multimeric form, such that unbound material is removed in the solution.

In a further embodiment of the method according to the invention an elution buffer is applied to the protein A chromatography material such that the bound antibody is released.

In a further embodiment of the method according to the invention the eluate recovered from the protein A chromatography is enriched in monomeric antibody over multimeric antibody with respect to the applied mixture.

As a skilled artisan would understand, in the present context the eluate recovered from the protein A chromatography has a protein content that contains a higher percentage of antibodies in monomeric form with respect to the mixture before the protein A chromatography step.

In a particular embodiment, the eluate recovered from the protein A chromatography comprises at least 50%, at least 60%, at least 70%, 75%, 80%, 85%, or at least 90% human VH3 domain-containing antibody in monomeric form.

In a further alternative embodiment, where the antibody in multimeric form is to be recovered, the eluate from the protein A chromatography has a protein content that contains a higher percentage of antibodies in multimeric form with respect to the mixture before the protein A chromatography step. In a particular embodiment the eluate recovered from the protein A chromatography comprises at least 50%, at least 60%, at least 70%, 75%, 80%, 85%, or at least 90% human VH3 domain-containing antibody in multimeric form.

In a further embodiment of the method according to the invention, said protein A is native recombinant protein A.

There are many chromatography materials available to the skilled artisan containing said native recombinant protein A, such as for example MabSelect® (GE Healthcare), Absolute® (Novasep), Captiv A® (Repligen), or Amsphere® (JSR).

In a particular embodiment of the method of the invention the bound antibody is released from the protein A chromatography material by applying an elution buffer with a pH suitable to disrupt antibody binding. Said pH is dependent on the specific molecule and generally determined empirically by the skilled artisan and adjusted to achieve the desired endpoint, i.e. it may be desired to recover the largest amount of monomer possible from the applied mixture, or it may be desirable to obtain the monomer at the highest possible purity. In a specific embodiment of the method of the invention the elution buffer has pH 3.0 to pH 4.5, preferably, pH 3.2 to pH 4.3, pH 3.5 to pH 4, preferably pH 3.6 to pH 3.9 or pH 3.8.

Buffers suitable for use as wash and elution buffers in protein A chromatography are readily available in the art, and may be chosen by way of non-limiting examples from among phosphate buffered saline (PBS), Tris, histidine, acetate, citrate buffers, or MES (2-(N-morpholino)ethanesulphonic acid Imidazole), BES (N,N-(bis-2-hydroxyethyl)-2-aminoethanesulphonic acid), MOPS (3-(N-morpholino)-propanesulphonic acid), or HEPES (N-2-hydroxyethylpiperazine-N'-2-ethanesulphonic acid) buffers.

In a particular embodiment, the method of the invention comprises applying a mixture comprising a human VH3 domain-containing antibody in monomeric and multimeric form to a protein A chromatography material wherein said protein A comprises domain D and/or E, under conditions that allow binding of said antibody to protein A, applying a first solution or wash buffer such that unbound material is removed in the solution, applying an elution buffer to the protein A chromatography material such that the bound antibody is released, and recovering the human VH3 domain containing-antibody in monomeric form, wherein the recovered solution is enriched in VH3 domain-containing antibody in monomeric form with respect to the applied mixture and wherein the human VH3 domain containing antibody does not contain an Fc region.

In a further particular embodiment, the method of the invention comprises applying a mixture comprising a human VH3 domain-containing antibody in monomeric and multimeric form to a protein A chromatography material wherein said protein A comprises domain D and/or E, under conditions that allow binding of said antibody to protein A, applying a first solution or wash buffer such that unbound material is removed in the solution, applying an elution buffer to the protein A chromatography material such that the bound antibody in monomeric form is released, and recovering the human VH3 domain containing-antibody in monomeric form, wherein the recovered solution is enriched in VH3 domain-containing antibody in monomeric form with respect to the applied mixture and wherein the human VH3 domain containing antibody does not contain an Fc region.

In a further embodiment according to the invention, the VH3 domain containing antibody is selected from Fab', $F(ab')_2$, scFv, Fab-Fv, Fab-scFv, Fab-$(scFv)_2$, Fab-$(Fv)_2$, diabodies, triabodies, and tetrabodies.

In a further embodiment of the method according to the invention, the VH3 domain-containing antibody comprises at least 2 human VH3 domains.

In a further embodiment of the method according to the invention the human VH3 domain-containing antibody specifically binds OX40.

In one embodiment of the method of the invention the antibody, is a FabFv or disulfide stabilised form thereof as disclosed in PCT/EP2014/074409, incorporated herein by reference.

In one embodiment the antibody comprises a binding domain specific to human serum albumin, in particular with CDRs or variable regions as disclosed in WO 2013/068563, incorporated herein by reference.

In a further embodiment of the method of the invention, said human VH3 domain containing antibody comprises:

heavy chain CDR1, CDR2 and CDR3 as defined in SEQ ID NO: 1, SEQ ID NO: 2 and SEQ ID NO: 3, respectively; and light chain CDR1, CDR2, and CDR3 as defined in SEQ ID NO: 4, SEQ ID NO: 5 and SEQ ID NO: 6, respectively.

In a further particular embodiment of the method according to the invention the antibody is A26Fab-645dsFv that comprises a Fab portion that specifically binds to OX40 and a Fv portion that specifically binds serum albumin, both portions being stabilized via a disulfide bond, as defined in WO 2013/068563, incorporated herein by reference.

In a further particular embodiment, the method of the invention comprises applying a mixture comprising A26Fab-645dsFv in monomeric and multimeric form to a protein A chromatography material wherein said protein A comprises domain D and/or E, under conditions that allow binding of said antibody to protein A, applying a first solution or wash buffer such that unbound material is removed in the solution, applying an elution buffer to the protein A chromatography material such that the bound antibody in monomeric form is released, and recovering the A26Fab-645dsFv in monomeric form, wherein the recovered solution is enriched in A26Fab-645dsFv in monomeric form with respect to the applied mixture and wherein the elution buffer has pH 3.5 to pH 4.2, preferably, pH 3.6 to pH 4.1, pH 3.7 to pH 4.0, preferably pH 3.8 to pH 3.9 or pH 3.8.

In a further particular embodiment, the method of the invention additionally comprises applying a second elution buffer to the protein A chromatography material to recover the bound A26Fab-645dsFv in multimeric form, wherein said second elution buffer has a pH below 3.5, preferably below pH 3.4, preferably pH 2.8 to pH 3.2, preferably pH 2.9 to pH 3.1, preferably pH 3.0.

Accordingly, the present disclosure provides a bispecific antibody fusion protein which binds human OX40 and human serum albumin comprising:

a heavy chain comprising, in sequence from the N-terminal, a first heavy chain variable domain (VH #1), a CH1 domain and a second heavy chain variable domain (VH #2), a light chain comprising, in sequence from the N-terminal, a first light chain variable domain (VL #1), a CL domain and a second light chain variable domain (VL #2), wherein said heavy and light chains are aligned such that VH #1 and VL #1 form a first antigen binding site and VH #2 and VL #2 form a second antigen binding site, wherein the antigen bound by the first antigen binding site is human OX40 and the antigen bound by the second antigen binding site is human serum albumin, in particular, wherein the first variable domain of the heavy chain (VH #1) comprises the sequence given in SEQ ID NO:1 for CDR-H1, the sequence given in SEQ ID NO:2 for CDR-H2 and the sequence given in SEQ ID NO:3 for CDR-H3 and the first variable domain of the light chain (VL #1) comprises the sequence given in SEQ ID NO:4 for CDR-L1, the sequence given in SEQ ID NO:5 for CDR-L2 and the sequence given in SEQ ID NO:6 for CDR-L3, wherein the second heavy chain variable domain (VH #2) has the sequence given in SEQ ID NO:11 and the second light chain variable domain (VL #2) has the sequence given in SEQ ID NO: 12 and the second heavy chain variable domain (VH #2) and second light chain variable domain (VL #2) are linked by a disulfide bond.

In one embodiment there is a peptide linker between the CH1 domain and the second heavy chain variable domain (VH #2). In one embodiment there is a peptide linker between the CL domain and the second light chain variable domain (VL #1). In one embodiment the first heavy chain variable domain (VH #1) comprises the sequence given in SEQ ID NO:8. In one embodiment the first light chain variable domain (VL #1) comprises the sequence given in SEQ ID NO:7. In one embodiment the heavy chain comprises or consists of the sequence given in SEQ ID NO:15. In one embodiment the light chain comprises or consists of the sequence given in SEQ ID NO:16.

Thus in one embodiment there is provided a bispecific antibody fusion protein which binds human OX40 and human serum albumin, having a heavy chain comprising the sequence given in SEQ ID NO:15 and a light chain comprising the sequence given in SEQ ID NO:16.

In one embodiment the antibody molecule, such as a Fab-dsFv format is one disclosed in PCT/EP2014/074409 or WO2014/019727, incorporated herein by reference.

In another embodiment the antibody molecule is a Fab-scFv fusion protein format disclosed in WO 2013/068571, incorporated herein by reference.

In another embodiment the antibody molecule is the multi-specific antibody molecule comprising or consisting of:

a) a polypeptide chain of formula (I):

VH—CH1-X—V1; and b) a polypeptide chain of formula (II):

VL-CL-Y—V2;

wherein:

VH represents a heavy chain variable domain;

CH1 represents a domain of a heavy chain constant region, for example domain 1 thereof;

X represents a bond or linker;

Y represents a bond or linker;

V1 represents a dsFv, a sdAb, a scFv or a dsscFv;

VL represents a light chain variable domain;

CL represents a domain from a light chain constant region, such as Ckappa;

V2 represents dsFv, a sdAb, a scFv or a dsscFv;

wherein at least one of V1 or V2 is a dsFv or dsscFv, described in WO 2015/197772 incorporated herein by reference.

In one particular embodiment, the antibody molecule is the multispecific antibody molecule of the format Fab-2x dsscFv described in WO 2015/197772, incorporated herein by reference.

In a further particular embodiment, the multispecific antibody molecule of the format Fab-2x dsscFv is a trivalent antibody, i.e. each Fv binds to a different epitope.

In a further particular embodiment the multispecific antibody molecule has a Fab-dsscFv-dsFv format as described in WO2015/197772, incorporated herein by reference.

An antibody that can be manufactured in accordance with the method of the present invention can be produced by culturing eukaryotic host cells transfected with one or more expression vectors encoding the recombinant antibody. The eukaryotic host cells are preferably mammalian cells, more preferably Chinese Hamster Ovary (CHO) cells.

Mammalian cells may be cultured in any medium that will support their growth and expression of the antibody, preferably the medium is a chemically defined medium that is free of animal-derived products such as animal serum and peptone. There are different cell culture mediums available to the person skilled in the art comprising different combinations of vitamins, amino acids, hormones, growth factors, ions, buffers, nucleosides, glucose or an equivalent energy source, present at appropriate concentrations to enable cell growth and protein production. Additional cell culture media components may be included in the cell culture medium at appropriate concentrations at different times during a cell culture cycle that would be known to those skilled in the art.

Mammalian cell culture can take place in any suitable container such as a shake flask or a bioreactor, which may or may not be operated in a fed-batch mode depending on the scale of production required. These bioreactors may be either stirred-tank or air-lift reactors. Various large scale bioreactors are available with a capacity of more than 1,000 L to 50,000 L, preferably between 5,000 L and 20,000 L, or to 10,000 L. Alternatively, bioreactors of a smaller scale such as between 2 L and 100 L may also be used to manufacture an antibody according to the method of the invention.

An antibody or antigen-binding fragment thereof that can be manufactured in accordance with the methods of the present invention is typically found in the supernatant of a mammalian host cell culture, typically a CHO cell culture. For CHO culture processes wherein the protein of interest such as an antibody or antigen-binding fragment thereof is secreted in the supernatant, said supernatant is collected by methods known in the art, typically by centrifugation.

Therefore in a particular embodiment of the invention, the method comprises a step of centrifugation and supernatant recovery prior to protein purification. In a further particular embodiment said centrifugation is continuous centrifugation. For avoidance of doubt, supernatant denotes the liquid lying above the sedimented cells resulting from the centrifugation of the cell culture.

Alternatively said supernatant may be recovered using clarification techniques known to the skilled artisan such as for example depth filtration. Therefore in a particular embodiment for the invention, the method comprises a step of depth filtration and supernatant recovery prior to protein purification.

Alternatively, host cells are prokaryotic cells, preferably gram-negative bacteria. More preferably, the host cells are *E. coli* cells. Prokaryotic host cells for protein expression are well known in the art (Terpe, K. (2006). Overview of bacterial expression systems for heterologous protein production: from molecular and biochemical fundamentals to commercial systems. Appl Microbiol Biotechnol 72, 211-222.). The host cells are recombinant cells which have been genetically engineered to produce the protein of interest such as an antibody fragment. The recombinant *E. coli* host cells may be derived from any suitable *E. coli* strain including from MC4100, TG1, TG2, DHB4, DH5α, DH1, BL21, K12, XL1Blue and JM109. One example is *E. coli* strain W3110 (ATCC 27,325__________) a commonly used host strain for recombinant protein fermentations. Antibody fragments can also be produced by culturing modified *E. coli* strains, for example metabolic mutants or protease deficient *E. coli* strains, such as those described in WO 2011/086136, WO 2011/086138 or WI 2011/086139, incorporated herein by reference.

An antibody that can be purified in accordance with the methods of the present invention is typically found in either the periplasm of the *E. coli* host cell or in the host cell culture supernatant, depending on the nature of the protein, the scale of production and the *E. coli* strain used. The methods for targeting proteins to these compartments are well known in the art (Makrides, S. C. (1996). Strategies for achieving high-level expression of genes in *Escherichia coli*. Microbiol Rev 60, 512-538.). Examples of suitable signal sequences to direct proteins to the periplasm of *E. coli* include the *E. coli* PhoA, OmpA, OmpT, LamB and OmpF signal sequences. Proteins may be targeted to the supernatant by relying on the natural secretory pathways or by the induction of limited leakage of the outer membrane to cause protein secretion examples of which are the use of the pelB leader, the protein A leader, the co-expression of bacteriocin release protein, the mitomycin-induced bacteriocin release protein along with the addition of glycine to the culture medium and the co-expression of the kil gene for membrane permeabilization. Most preferably, in the methods of the invention, the recombinant protein is expressed in the periplasm of the host *E. coli*.

Expression of the recombinant protein in the *E. coli* host cells may also be under the control of an inducible system, whereby the expression of the recombinant antibody in *E. coli* is under the control of an inducible promoter. Many inducible promoters suitable for use in *E. coli* are well known in the art and depending on the promoter expression of the recombinant protein can be induced by varying factors such as temperature or the concentration of a particular substance in the growth medium. Examples of inducible promoters include the *E.coli* lac, tac, and trc promoters which are inducible with lactose or the non-hydrolyzable lactose analog, isopropyl-b-D-1-thiogalactopyranoside (IPTG) and the phoA, trp and araBAD promoters which are induced by phosphate, tryptophan and L-arabinose respectively. Expression may be induced by, for example, the addition of an inducer or a change in temperature where induction is temperature dependent. Where induction of recombinant protein expression is achieved by the addition of an inducer to the culture the inducer may be added by any suitable method depending on the fermentation system and the inducer, for example, by single or multiple shot additions or by a gradual addition of inducer through a feed. It will be appreciated that there may be a delay between the addition of the inducer and the actual induction of protein expression for example where the inducer is lactose there may be a delay before induction of protein expression occurs while any pre-existing carbon source is utilized before lactose.

*E. coli* host cell cultures (fermentations) may be cultured in any medium that will support the growth of *E. coli* and expression of the recombinant protein. The medium may be any chemically defined medium such as e.g. described in Durany O, et al. (2004). Studies on the expression of recombinant fuculose-1-phosphate aldolase in *Escherichia coli*. Process Biochem 39, 1677-1684.

Culturing of the *E. coli* host cells can take place in any suitable container such as a shake flask or a fermenter depending on the scale of production required. Various large scale fermenters are available with a capacity of more than 1,000 liters up to about 100,000 liters. Preferably, fermenters of 1,000 to 50,000 liters are used, more preferably 1,000 to 25,000, 20,000, 15,000, 12,000 or 10,000 liters. Smaller scale fermenters may also be used with a capacity of between 0.5 and 1,000 liters.

Fermentation of *E. coli* may be performed in any suitable system, for example continuous, batch or fed-batch mode depending on the protein and the yields required. Batch mode may be used with shot additions of nutrients or inducers where required. Alternatively, a fed-batch culture may be used and the cultures grown in batch mode pre-induction at the maximum specific growth rate that can be sustained using the nutrients initially present in the fermenter and one or more nutrient feed regimes used to control the growth rate until fermentation is complete. Fed-batch mode may also be used pre-induction to control the metabolism of the *E. coli* host cells and to allow higher cell densities to be reached.

If desired, the host cells may be subject to collection from the fermentation medium, e.g. host cells may be collected from the sample by centrifugation, filtration or by concentration.

In one embodiment the process according to the present invention comprises a step of centrifugation and cell recovery prior to extracting the protein.

For *E. coli* fermentation processes wherein the protein of interest such as an antibody fragment is found in the periplasmic space of the host cell it is required to release the protein from the host cell. The release may be achieved by any suitable method such as cell lysis by mechanical or pressure treatment, freeze-thaw treatment, osmotic shock, extraction agents or heat treatment. Such extraction methods for protein release are well known in the art. Therefore in a particular embodiment, the method of the invention comprises an additional protein extraction step prior to protein purification.

In a further embodiment the method according to the invention further comprises recovering the host cells from the cell culture medium, harvesting the protein using a protein extraction step, recovering the protein containing mixture resulting from the protein extraction step and purifying said protein from the mixture wherein said purification comprises at least one protein A chromatography step.

In a specific embodiment the extraction step comprises adding an extraction buffer to the sample and recovering the resulting protein. Preferably the extraction step is performed during a suitable time and at a suitable temperature to allow recovery of the protein in its native conformation and is optimized empirically for each particular protein. In a particular embodiment of the present invention said extraction step is performed at 25° C. to 35° C., 27° C. to 33° C., preferably 29° C. to 31° C. The protein extraction step is performed over a period of time that is also optimized empirically depending on the particular protein and temperature to be used. In a particular embodiment said extraction step is performed for 4 to 20 hours, for 6 to18 hours, preferably from 8 to 12 hours. In a particular embodiment the protein extraction step is performed from 8 to 12 hours at 29° C. to 31° C., preferably for 11 hours at 30° C.

In an alternative embodiment an extraction buffer is added to the sample and the sample is then subjected to a heat treatment step. The heat treatment step is preferably as described in detail in U.S. Pat. No. 5,665,866, incorporated herein by reference.

Following the step of extraction the mixture containing the protein of interest such as an antibody may be subjected to a step of centrifugation and/or filtration.

In a further particular embodiment, the method of the invention may comprise a step of adjusting the pH of the mixture containing the protein of interest following the extraction step and prior to purification of the protein from said mixture.

The term "antibody" or "antibodies" as used herein refers to monoclonal or polyclonal antibodies. The term "antibody" or "antibodies" as used herein includes but is not limited to recombinant antibodies that are generated by recombinant technologies as known in the art. "Antibody" or "antibodies" include antibodies' of any species, in particular of mammalian species, including antibodies having two essentially complete heavy and two essentially complete light chains, human antibodies of any isotype, including IgD, $IgG_1$, $IgG_{2a}$, $IgG_{2b}$, $IgG_3$, $IgG_4$, IgE and antibodies that are produced as dimers of this basic structure including $IgA_1$, $IgA_2$, or pentamers such as IgM and modified variants thereof, non-human primate antibodies, e.g. from chimpanzee, baboon, rhesus or cynomolgus monkey, rodent antibodies, e.g. from mouse, or rat; rabbit antibodies, goat or horse antibodies, and camelid antibodies (e.g. from camels or llamas such as Nanobodies™) and derivatives thereof, or of bird species such as chicken antibodies or of fish species such as shark antibodies. The term "antibody" or "antibodies" also refers to "chimeric" antibodies in which a first portion of at least one heavy and/or light chain antibody sequence is from a first species and a second portion of the heavy and/or light chain antibody sequence is from a second species. Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences. "Humanized" antibodies are chimeric antibodies that contain a sequence derived from non-human antibodies. For the most part, humanized antibodies are human antibodies (recipient antibody) in which residues from a hypervariable region of the recipient are replaced by residues from a hypervariable region [or complementarity determining region (CDR)] of a non-human species (donor antibody) such as mouse, rat, rabbit, chicken or non-human primate, having the desired specificity, affinity, and activity. In most instances residues of the human (recipient) antibody outside of the CDR; i.e. in the framework region (FR), are additionally replaced by corresponding non-human residues. Furthermore, humanized antibodies may comprise residues that are not found in the recipient antibody or in the donor antibody. These modifications are made to further refine antibody performance. Humanization reduces the immunogenicity of non-human antibodies in humans, thus facilitating the application of antibodies to the treatment of human disease. Humanized antibodies and several different technologies to generate them are well known in the art. The term "antibody" or "antibodies" also refers to human antibodies, which can be generated as an alternative to humanization. For example, it is possible to produce transgenic animals (e.g., mice) that are capable, upon immunization, of producing a full repertoire of human antibodies in the absence of production of endogenous murine antibodies. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies with specificity against a particular antigen upon immunization of the transgenic animal carrying the human germ-line immunoglobulin genes with said antigen. Technologies for producing such transgenic animals and technologies for isolating and producing the human antibodies from such transgenic animals are known in the art. Alternatively, in the transgenic animal; e.g. mouse, only the immunoglobulin genes coding for the variable regions of the mouse antibody are replaced with corresponding human variable immunoglobulin gene sequences. The mouse germline immunoglobulin genes coding for the antibody constant regions remain unchanged. In this way, the antibody effector functions in the immune system of the transgenic mouse and consequently the B cell development are essentially unchanged, which may lead to an improved antibody response upon antigenic challenge in vivo. Once the genes coding for a particular antibody of interest have been isolated from such transgenic animals the genes coding for the constant regions can be replaced with human constant region genes in order to obtain a fully human antibody. Other methods for obtaining human antibodies in vitro are based on display technologies such as phage display or ribosome display technology, wherein recombinant DNA libraries are used that are either generated at least in part artificially or from immunoglobulin variable (V) domain gene repertoires of donors. Phage and ribosome display technologies for generating human antibodies are well known in the art. Human antibodies may also be generated from isolated human B cells that are ex vivo immunized with an antigen of interest and subsequently fused to generate hybridomas which can then be screened for the optimal human antibody. The term “antibody” or “antibodies” as used herein, also refers to an aglycosylated antibody.

Antibody molecules to be used in any of the embodiments of the invention include antibody fragments such as Fab, Fab', F(ab')2, and Fv and scFv fragments; as well as diabodies, including formats such as BiTEs® (Bi-specific T-cell Engagers) and DARTs™ (Dual Affinity Re-Targeting technology), triabodies, tetrabodies, minibodies, domain antibodies(dAbs), such as sdAbs, VHH and VNAR fragments, single-chain antibodies, bispecific, trispecific, tetraspecific or multispecific antibodies formed from antibody fragments or antibodies, including but not limited to Fab-Fv, Fab-scFv, $Fab(Fv)_2$ or $Fab-(scFv)_2$ constructs. Antibody fragments as defined above are known in the art. For the purpose of clarity Fab-Fv should be understood to refer to a construct containing one Fv region and one Fab region joined in any order, i.e. Fab-Fv, or Fv-Fab, wherein the last amino acids in one region are followed by the first amino acids in the next region or vice versa. Similarly Fab-scFv should be understood to refer to a construct containing one scFv region and one Fab region joined in any order and in the case of the Fab to either polypeptide chain, i.e. Fab-scFv, or scFv-Fab, wherein the last amino acid in one region is followed by the first amino acid in the next region or vice versa. In the same manner $Fab-(Fv)_2$ should be understood to refer to a construct containing two Fv regions and one Fab region joined in any order, i.e. Fab-Fv-Fv, Fv-Fab-Fv, or Fv-Fv-Fab, wherein the last amino acids in one region are followed by the first amino acids in the next region or vice versa. Similarly $Fab-(scFv)_2$ should be understood to refer to a construct containing two scFv regions and one Fab region joined in any order and in the case of the Fab to either polypeptide chain, resulting in 20 possible permutations.

Typically these constructs include a peptide linker between the first region (e.g. Fab) and the second region (e.g. Fv). Such linkers are well known in the art, and can be one or more amino acids, typically optimized in length and composition by a skilled artisan. Alternatively said regions may be linked directly, i.e. without a peptide linker.

Examples of suitable linker regions for linking a variable domain to a Fab or Fab' are described in WO 2013/068571 and WO 2014/096390 incorporated herein by reference, and include, but are not limited to, flexible linker sequences and rigid linker sequences. Flexible linker sequences include those disclosed in Huston et al., 1988, 10 PNAS 85:5879-5883; Wright & Deonarain, Mol. Immunol., 2007, 44(11): 2860-2869; Alfthan et al., Prot. Eng., 1995, 8(7):725-731; Luo et al., J. Biochem., 1995, 118(4):825-831; Tang et al., 1996, J. Biol. Chern. 271(26): 15682-15686; and Turner et al., 1997, JIMM 205, 42-54.

The term “VH3 domain” as used herein refers to the framework subgroup 3 of the human heavy chain variable region of an immunoglobulin. The heavy chain variable domains of antibodies are classified into distinct subfamilies (VH1 to VH6) on the basis of DNA sequence and protein homologies (Walter et al. Am. J. Hum. Genet. 42:446-451, 1988, *Analysis for genetic variation reveals human immunoglobulin VH-region gene organization;* Schroeder et al. Int Immunol. 1990; 2(1):41-50, *Structure and evolution of mammalian VH families.*

The term “Fc region” as used herein refers to the Fc region of a native antibody, this is a constant region dimer lacking constant heavy domain 1 (CH1). As is known in the art the Fc region of an antibody is the Fragment crystallizable (Fc) recovered after digestion of the native antibody with either pepsin or papain.

An antibody that “does not contain an Fc region” as used herein refers to an antibody that does not contain a native constant heavy domain 2 (CH2), a native constant heavy domain 3 (CH3) nor a native constant heavy domain 4 (CH4) region.

The residues within the Fc region responsible for binding to protein A have been previously described in the art (Nagaoka et al. *Single amino acid substitution in the mouse IgG1 Fc region induces drastic enhancement of the affinity to protein A,* PEDS Vol. 16, Issue 4, pages 243-245). Consequently it is possible for a skilled artisan to develop an antibody having an Fc region that has lost the ability to bind to protein A, and such antibody would be suitable for use in the method according to the present invention.

Figure 12:
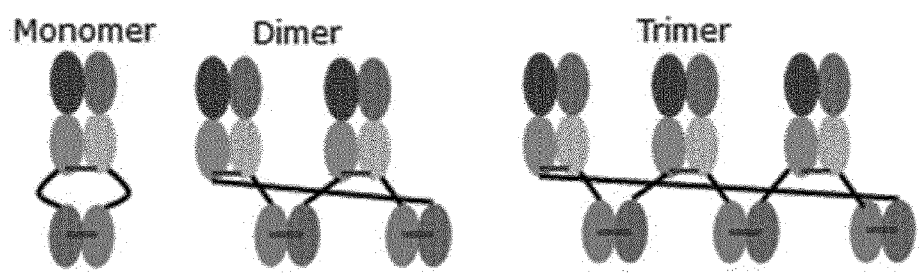
FIG. 12 shows a schematic of monomeric Fab-dsFv and multimeric versions of Fab-dsFv, and also of its basic components: Fab and dsFv. This diagram illustrates possible monomers, dimers and trimers. However, all the linkers would be the same length in reality where dimers, and trimers form cyclic structures.

The term “multimer” or “multimeric form” as used herein refers to antibody forms consisting of the domains from two or more monomers in which all of the domains are correctly folded and paired. Examples of multimers are provided in FIG. 12, where the different antibody molecules are correctly folded and each VH domain is paired with a complementary VL domain. For the purposes of clarity, it should be understood that a complementary VH-VL pair binds the same antigen cooperatively.

The term “Protein A” or “Staphylococcal Protein A” as used herein, is a type I membrane protein covalently linked to the cell wall of most strains of the Gram-positive bacterium *Staphylococcus aureus.* It has high affinity to IgG from various species, for instance human, rabbit and guinea pig but only weak interaction with bovine and mouse. Protein A interacts with antibodies through two distinct binding events: the “classical” binding site on the Fc portion of human $IgG_1$, $IgG_2$, and $IgG_4$, and the “alternate” binding site found on the Fab portion of human IgG, IgM, IgA, and IgE that contain heavy chains of the VH3 subfamily. The most reported molecular weight of protein A from *Staphylococcus aureus* is about 42,000 Da. The recombinant Streptococci protein A consists of 299 amino acids and has a predicted molecular mass of 33.8 kDa as estimated by SDS-PAGE.

Protein A consists of three regions: S, being the signal sequence that is processed during secretion; five homologous IgG binding domains E, D, A, B and C and a cell-wall anchoring region XM. The truncated protein lacking region X has a molecular weight of about 31 kD. The domains are independently capable to bind to the Fc-part of $IgG_1$, $IgG_2$ and $IgG_4$, but show only weak interaction with $IgG_3$. In addition, all native protein A domains show comparable Fab binding, that has been described to be mediated by regions D and E.

The term "OX40" as used herein refers to a molecule also known as CD134, TNFRSF4, ACT35 or TXGP1L, is a member of the TNF receptor superfamily, that acts as a costimulatory receptor with sequential engagement of CD28 and OX40 being required for optimal T cell proliferation and survival.

The term "specifically binds to", "specifically binding to" a given molecule, and equivalents as used herein when referring to an antibody means the antibody will bind to said given molecule with sufficient affinity and specificity to achieve a biologically meaningful effect. The antibody selected will normally have a binding affinity for the given molecule, for example, the antibody may bind the given molecule with a Kd value of between 100 nM and 1 pM. Antibody affinities may be determined by a surface plasmon resonance bases assay, such as the BIAcore assay; enzyme-linked immunoabsorbent assay (ELISA); and competition assays (e.g. RIA's), for example. Within the meaning of the present invention an antibody specifically binding to said given molecule, may also bind to another molecule; such as by way of a non-limiting example in the case of a bispecific antibody.

EXAMPLES

Example 1

Protein-A Purification of A26Fab-645dsFv via a pH Gradient Elution

*E.coli* Expression, Extraction and Clarification of A26Fab-645dsFv

A26Fab-645dsFv (an antibody fragment that binds human OX40 and serum albumin) was expressed as a heterologous protein in *E. coli* W3110 host cells upon induction by IPTG (isopropyl-b-D-1-thiogalactopyranoside) and the heterologous protein was released from the periplasmic space of the host cells by the addition of 100 mM Tris/10 mM EDTA buffer adjusted to pH 7.4 and protein extraction step at 30° C. Cellular material was removed through centrifugation and the cell extract containing the heterologous protein was then clarified using a combination of centrifugation and 0.22 μm filtration.

Protein-A Purification of A26Fab-645dsFv via a pH Gradient Elution

The clarified *E. coli* extract was applied to a native protein A chromatography column, 5 ml HiTrap MabSelect (GE Healthcare), equilibrated in Delbeccos Phosphate Buffered Saline (PBS) pH 7.4. The column was first washed with PBS to remove unbound material, and bound material was subsequently eluted with a pH gradient, pH 7.4 to pH 2.1. Eluted material was fractionated and analysed via SEC-HPLC (size exclusion chromatography—high performance liquid chromatography) using TSK gel G3000SWXL SEC-HPLC (Tosoh Corporation). SEC-HPLC analysis was used to determine the % monomer and multimer present in each fraction. A26Fab-645dsFv monomer had a retention time around 9 minutes. Dimer, trimer, tetramer, and higher order structures all showed retention times below 9 minutes and were collectively termed multimeric species or higher molecular weight species (HMWS).

Figure 2:
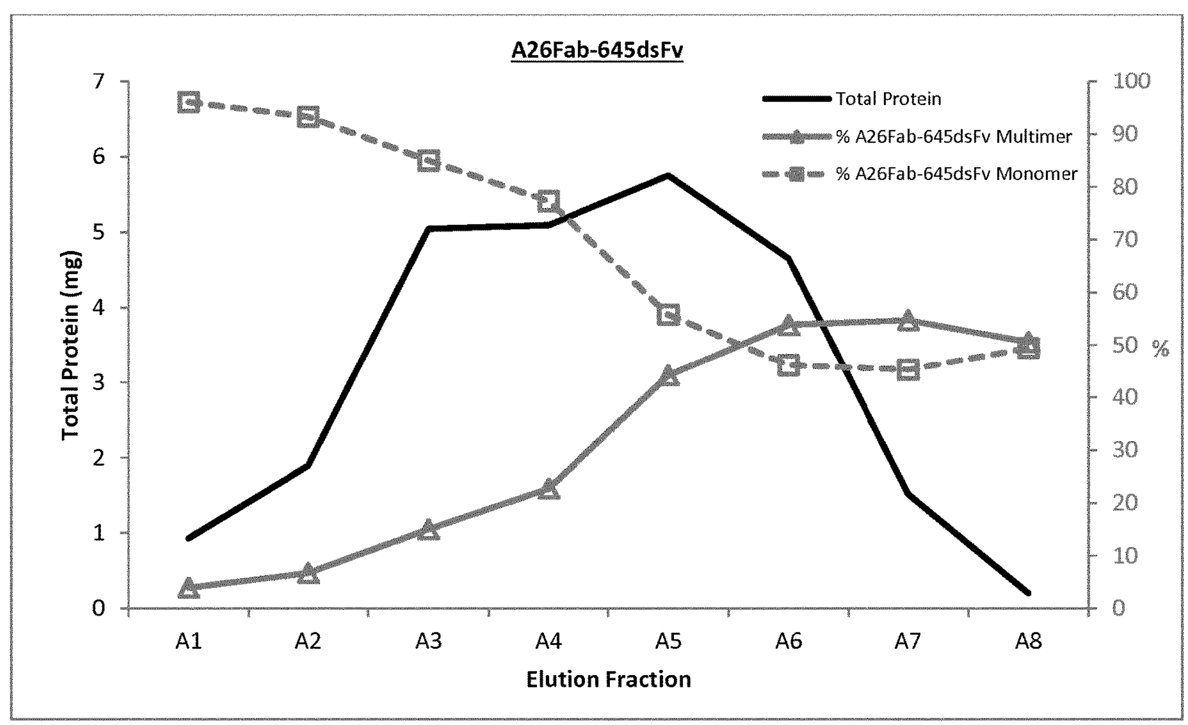
FIG. 2 shows the amount of total protein, monomeric and multimeric A26Fab-645dsFv present in each of the fractions resulting from the chromatography depicted in FIG. 1, as analysed by SEC-HPLC.

During elution from the protein A chromatography column, two peaks were observed across the pH gradient, see FIG. 1. Elevated levels of monomer were observed in the first peak compared to elevated levels of multimeric species in the second peak, see table 1 and FIG. 2.

A26Fab-645dsFv lacks an Fc therefore binding to Protein-A was due to the human VH3 variable framework subclass of the V-regions. It is proposed that the increased binding of the multimeric species was due to the increased avidity of these molecules for protein-A. Multimeric species have more VH3 regions and therefore bind stronger to the Protein-A resin requiring a lower pH for elution.

TABLE 1

SEC G3000 Analysis of fractions from Protein-A Purification of A26Fab-645dsFv via a pH gradient elution

| Fraction | Volume (ml) | Conc (mg/ml) | Protein (mg) | HMWS (%) | Monomer (%) |
|---|---|---|---|---|---|
| A1 | 3.3 | 0.3 | 0.9 | 4.0 | 96.1 |
| A2 | 3.1 | 0.6 | 1.9 | 6.7 | 93.3 |
| A3 | 3.2 | 1.6 | 5.0 | 15.0 | 85.0 |
| A4 | 3.2 | 1.6 | 5.1 | 22.7 | 77.3 |
| A5 | 3.2 | 1.8 | 5.8 | 44.2 | 55.8 |
| A6 | 3.3 | 1.4 | 4.6 | 53.8 | 46.2 |
| A7 | 3.3 | 0.5 | 1.5 | 54.7 | 45.3 |
| A8 | 1.0 | 0.2 | 0.2 | 50.6 | 49.4 |

Example 2

Protein-A Purification of an Fc Construct via a pH Gradient Elution

CHO Expression and Clarification of Multimeric Fc

An Fc construct containing an Fc domain from human IgG1 fused to the human IgM tail piece that caused the Fc to assemble into multimers, was expressed in a stable dihydrofolate reductase (DHFR) deficient Chinese Hamster Ovary cell line (CHO DG44). Cells were transfected using a Nuclefector (Lonza) following the manufacturer's instructions with a plasmid vector containing both the gene for DHFR as a selectable marker and the genes encoding the product. Transfected cells were selected in medium lacking hypoxanthine and thymidine, and in the presence of the DHFR inhibitor methotrexate. Cultures were maintained in shaken flasks culture in batch mode and harvested after 14 days.

Clarification of the cell culture supernatant was carried out via centrifugation (4000×g for 60 minutes at room temperature) followed by depth and sterile filtration.

Clarified cell culture supernatant was concentrated and all Fc containing constructs were purified using a protein A chromatography column, a 5 ml HiTrap MabSelect SuRe (GE Healthcare), equilibrated in PBS pH 7.4. The column was washed with PBS and bound material was eluted with 0.1M Citrate pH 3.4. Eluted material was buffer exchanged into PBS pH 7.4.

Figure 3:
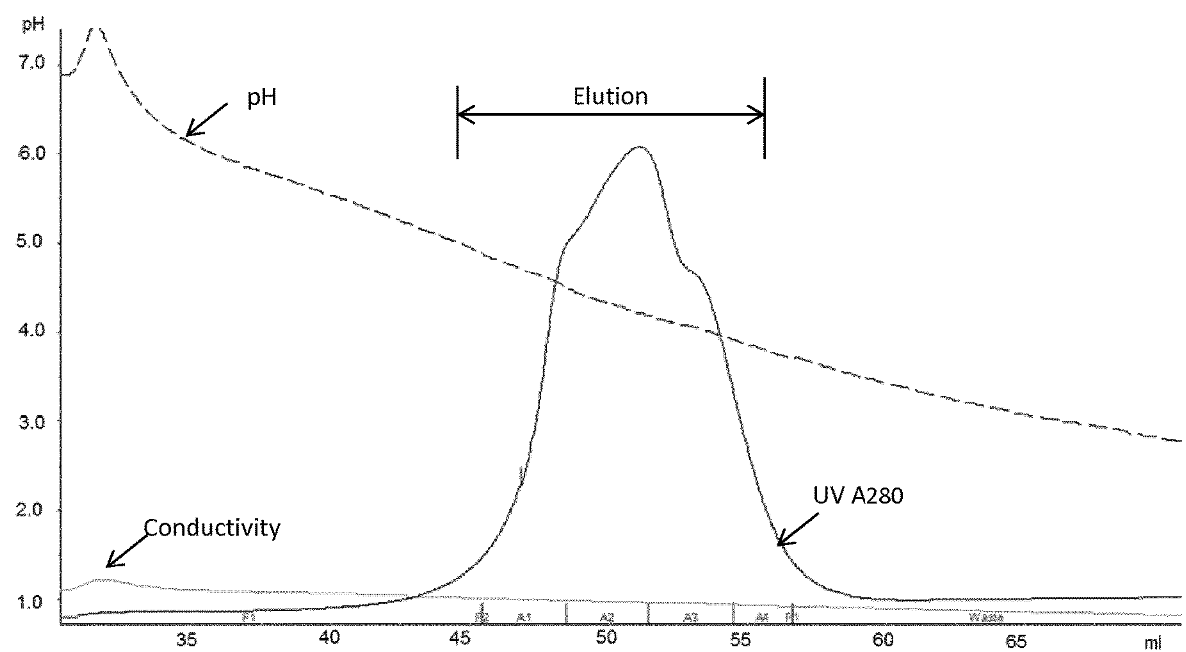
FIG. 3 is a chromatogram showing the elution profile of an Fc construct from a Protein A resin via a pH gradient elution.
Figure 4:
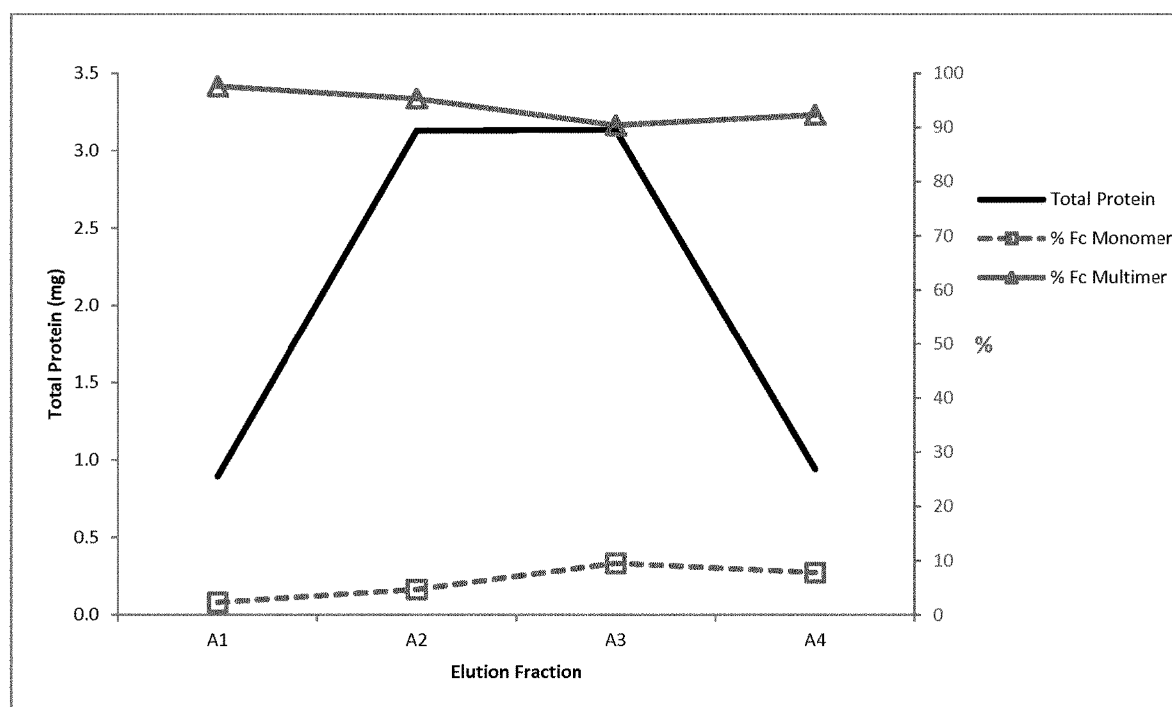
FIG. 4 shows the amount of total protein, monomeric and multimeric forms present in each of the fractions resulting from the chromatography depicted in FIG. 3, as analysed by SEC-HPLC.

The purified Fc constructs was applied to a native protein A chromatography column, 5 ml HiTrap MabSelect (GE Healthcare), equilibrated in PBS pH 7.4. The column was first washed with PBS to remove unbound material, and bound material was subsequently eluted with a pH gradient, pH7.4 to pH 2.1, see FIG. 3. Eluted material was fractionated and analysed via SEC-HPLC (G3000 SEC-HPLC, Tosoh Corporation). SEC-HPLC analysis was used to determine the % monomeric and multimeric Fc present in each fraction. Fc monomer has a retention time around 9.3 minutes. Trimer, hexamer, and higher order structures all have retention times below 9.4 minutes and were collectively termed multimeric species or higher molecular weight species (HMWS), see table 2 and FIG. 4.

TABLE 2

G3000 SEC Analysis of fractions from Protein-A Purification of Multimeric Fc via a pH gradient elution

| Fraction | Total Protein (mg) | % Fc Monomer | % Fc Multimer |
|---|---|---|---|
| A1 | 0.89 | 2.3 | 97.6 |
| A2 | 3.13 | 4.7 | 95.3 |
| A3 | 3.14 | 9.5 | 90.4 |
| A4 | 0.94 | 7.8 | 92.3 |

The Fc construct eluted as a single peak with a slight shoulder on the upward and downward inflection. However analysis of the fractions by SEC-HPLC revealed that monomeric and multimeric forms of the molecule elute in parallel, see table 2 and FIG. 4. No separation between the different species was observed across the gradient elution.

The multimers of Fc construct contain multiple Fc regions but lack variable regions and so lack the possibility of binding Protein-A through the human VH3 domain. The monomeric and multimeric Fc constructs co-elute from the Protein-A column in a gradient elution, demonstrating that Fc region avidity for the resin was not a factor for elution. Therefore monomeric and multimeric Fc region containing molecules cannot be efficiently separated by this technique. This is in contrast to examples 1 and 2 where the elution from Protein-A of VH3-domain containing antibodies that do not have an Fc region using a pH gradient was able to separate monomers from multimers.

Example 3

Protein-A Purification of A26Fab-645dsFv via pH Step Elution

CHO Expression and Clarification of A26Fab-645dsFv

The construct which binds human OX40 and serum albumin was expressed in a stable dihyrofolate reductase (DHFR) deficient Chinese Hamster Ovary cell line (CHO DG44). Cells were transfected by electroporation using a Nuclefector (Lonza) following the manufacturer's instructions with a plasmid vector containing both the gene for DHFR as a selectable marker and the genes encoding the product. Transfected cells were selected in medium lacking hypoxanthine and thymidine, and in the presence of the DHFR inhibitor methotrexate. Cultures were maintained in shaken flasks culture in batch mode and harvested after 14 days.

Clarification of the cell culture supernatant was carried out via centrifugation (4000×g for 60 minutes at room temperature) followed by depth and sterile filtration.

Protein-A Purification of A26Fab-645dsFv via pH Step Elution

Figure 5:
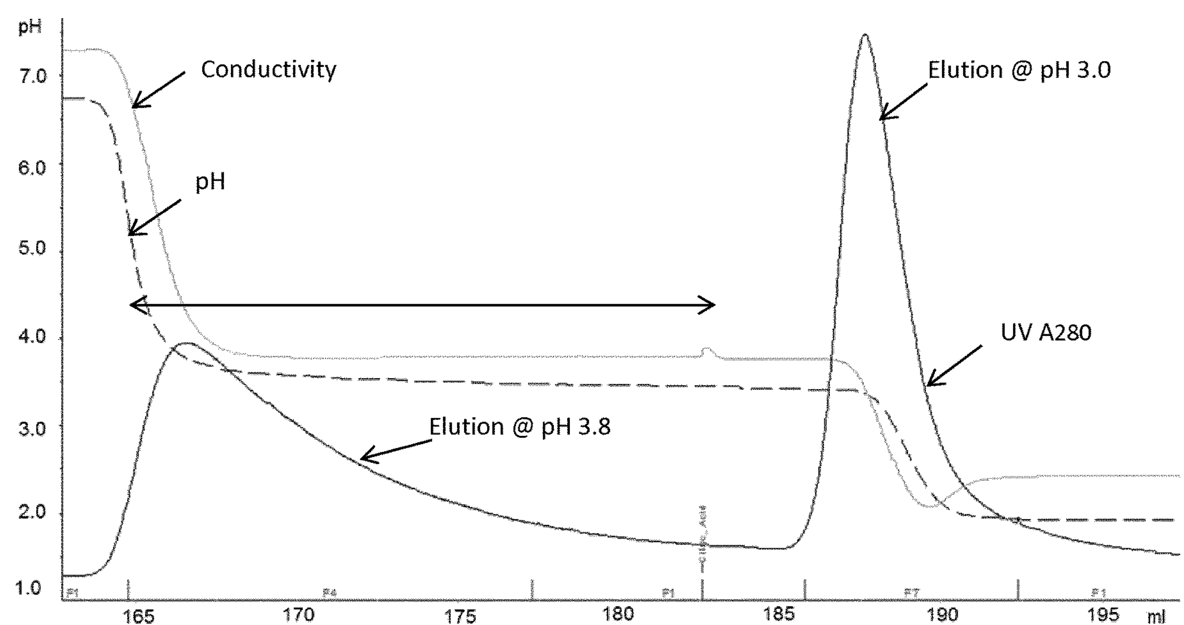
FIG. 5 is a chromatogram showing the elution profile of A26Fab-645dsFv from a Protein A resin via pH step elution.

Clarified cell culture supernatant was applied to a native protein A chromatography column, 5 ml HiTrap MabSelect (GE Healthcare), equilibrated in Delbeccos Phosphate Buffered Saline (PBS) pH 7.4. The column was first washed with PBS to remove unbound material and bound material was subsequently eluted first at pH3.8 and then a second elution step was carried out at pH 3.0, see FIG. 5. Eluted material was fractionated and analysed via SEC-HPLC (G3000 SEC-HPLC, Tosoh Corporation) and 4-20% Tris/Glycine SDS-PAGE performed under both reducing and non-reducing conditions.

Figure 6:
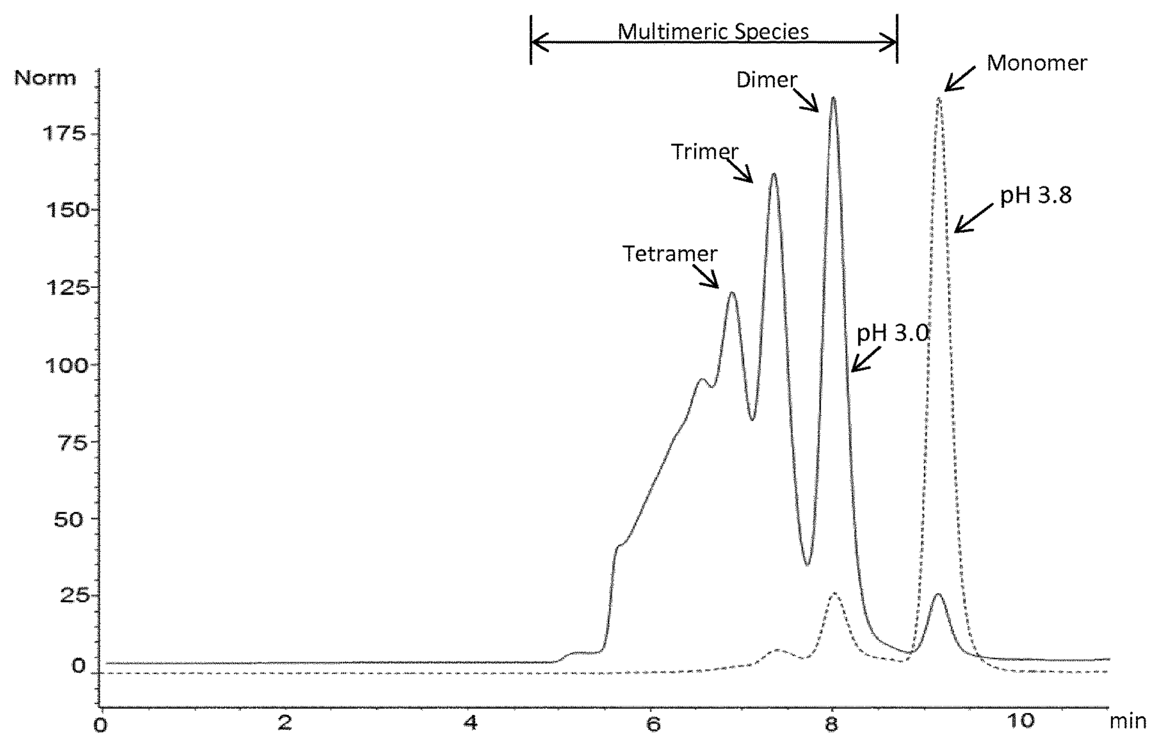
FIG. 6 shows a SEC-HPLC analysis of the fractions resulting from the protein A chromatography depicted in FIG. 5. The dotted line represents the analysis of the fraction eluted at pH 3.8, whereas the uninterrupted line represents the analysis of the fraction eluted at pH 3.0.

SEC-HPLC analysis was used to determine the % monomer and multimer present in each fraction. A26Fab-645dsFv monomer has a retention time around 9 minutes. Dimer, trimer, tetramer, and higher order structures all have retention times below 9 minutes and were collectively termed multimeric species or higher molecular weight species (HMWS), see FIG. 6 and table 3.

TABLE 3

G3000 SEC Analysis of Fractions from Protein-A Purification of A26Fab-645dsFv via pH Step Elution

| | Volume (ml) | Conc (mg/ml) | Total Protein (mg) | HMWS (%) | Monomer (%) |
|---|---|---|---|---|---|
| pH 3.8 | 13.8 | 0.67 | 9.2 | 21.3 | 78.7 |
| pH 3.0 | 7.5 | 1.04 | 7.8 | 96.8 | 3.2 |

Figure 7:
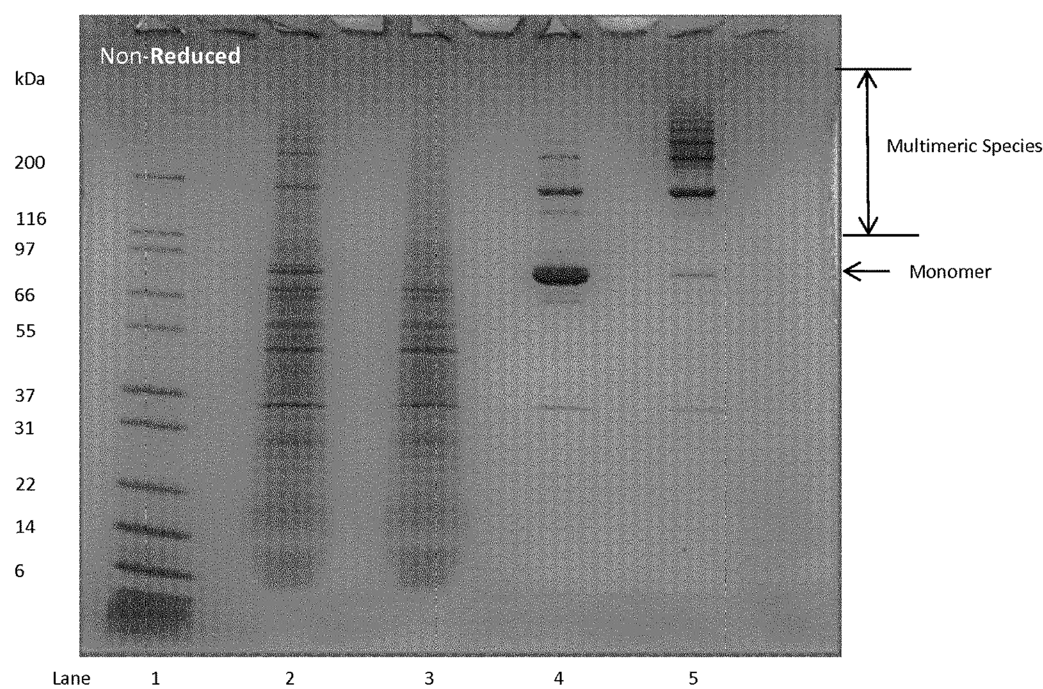
FIG. 7 shows a non-reducing SDS-PAGE analysis of fractions recovered from the protein A chromatography of A26Fab-645dsFv via pH step elution depicted in FIG. 5. Lane 1 shows molecular weight markers, lane 2 shows a sample of clarified cell culture supernatant as loaded on to the protein A chromatography, lane 3 shows the flow-through fraction recovered from the protein A chromatography, lane 4 the fraction recovered after elution at pH 3.8, and lane 5 the fraction recovered after elution at pH 3.0.

Non-reducing SDS-PAGE confirmed the above monomer and multimer levels in the elution peaks. A26Fab-645dsFv monomer migrates between the 97-66 kDa and is the major band in lane 4, corresponding to elution at pH 3.8, A26Fab-645dsFv multimers migrate as multiple bands above 120 kDa and are the majority of bands in lane 5, corresponding to the fraction recovered from elution at pH 3.0, see FIG. 7.

Figure 8:
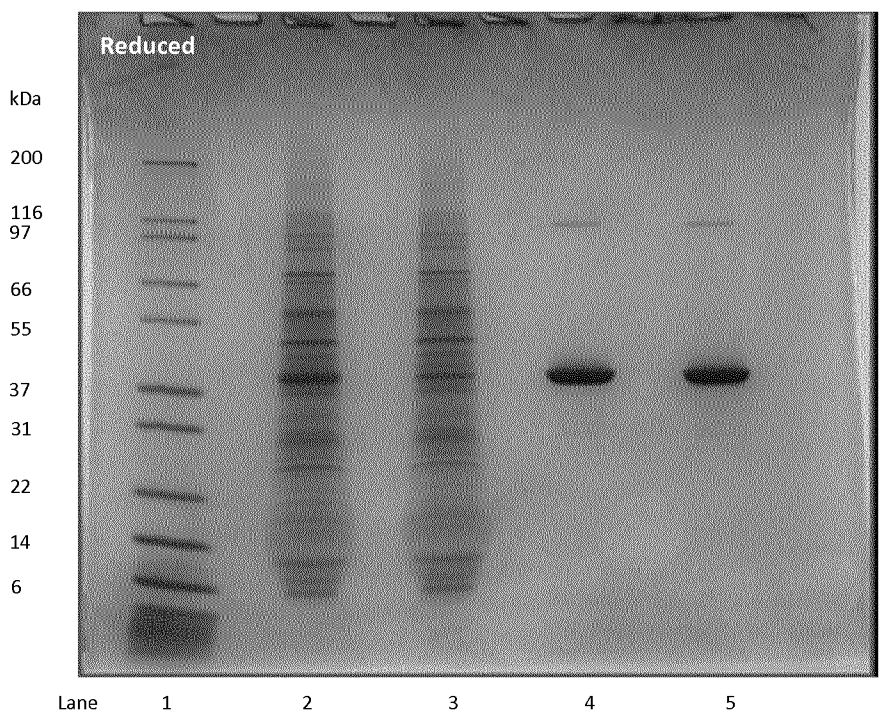
FIG. 8 shows a reducing SDS-PAGE analysis of fractions recovered from the protein A chromatography of A26Fab-645dsFv via pH step elution depicted in FIG. 5. Lane 1 shows molecular weight markers, lane 2 shows a sample of clarified cell culture supernatant as loaded on to the protein A chromatography, lane 3 shows the flow-through fraction recovered from the protein A chromatography, lane 4 the fraction recovered after elution at pH 3.8, and lane 5 the fraction recovered after elution at pH 3.0.

Reducing SDS-PAGE confirmed that all bands on the non-reduced SDS-PAGE were related to A26Fab-645dsFv, see FIG. 8.

The elution at pH 3.8 eluted a single peak in 2.8 column volumes with a slight tail on the downward inflection. SEC-HPLC analysis demonstrated that this peak contained 79% A26Fab-645dsFv in monomeric form, the high amount of monomer was also confirmed by non-reducing SDS-PAGE analysis. The elution at pH 3.0 eluted a single peak. HPLC-SEC analysis demonstrated that this peak was 97% A26Fab-645dsFv in multimeric form, the high amount of multimer was also confirmed by non-reducing SDS-PAGE analysis.

The above results demonstrate that efficient separation of monomer from multimer species via VH3 binding to protein A is possible. This is in contrast to Fc binding to Protein-A as shown in the previous example.

Example 4

Protein-A (Amsphere) Purification of A26Fab-645dsFv via a Gradient Elution

CHO Expression and Clarification of A26Fab-645dsFv

The construct which binds human OX40 and serum albumin was expressed in a stable dihyrofolate reductase (DHFR) deficient Chinese Hamster Ovary cell line (CHO DG44). Cells were transfected by electroporation using a Nuclefector (Lonza) following the manufactures instructions with a plasmid vector containing both the gene for DHFR as a selectable marker and the genes encoding the product. Transfected cells were selected in medium lacking hypoxanthine and thymidine, and in the presence of the DHFR inhibitor methotrexate. Cultures were maintained in shaken flasks culture in batch mode and harvested after 14 days.

Clarification of the cell culture supernatant was carried out via centrifugation (4000×g for 60 minutes at room temperature) followed by depth and sterile filtration.

Protein-A Purification (Amsphere) of A26Fab-645dsFv via a pH Gradient Elution

The clarified supernatant was applied to the Amsphere protein A chromatography column, (5 ml column volume with 10 cm bed height) and was equilibrated in Delbeccos Phosphate Buffered Saline (PBS) pH 7.4. The column was then washed with PBS to remove unbound material, and bound material was subsequently eluted with a pH gradient, pH 6.0 to pH 2.1. Eluted material was fractionated and analysed via SEC-UPLC (size exclusion chromatography—ultra performance liquid chromatography) using Acquity UPLC BEH450 SEC 2.5 μm column. SEC-UPLC analysis was used to determine the % monomer and multimer present in each fraction. A26Fab-645dsFv monomer had a retention time around 2.2 minutes. Dimer, trimer, tetramer, and higher order structures all showed retention times below 2.2 minutes and were collectively termed multimeric species or higher molecular weight species (HMWS).

Figure 9:
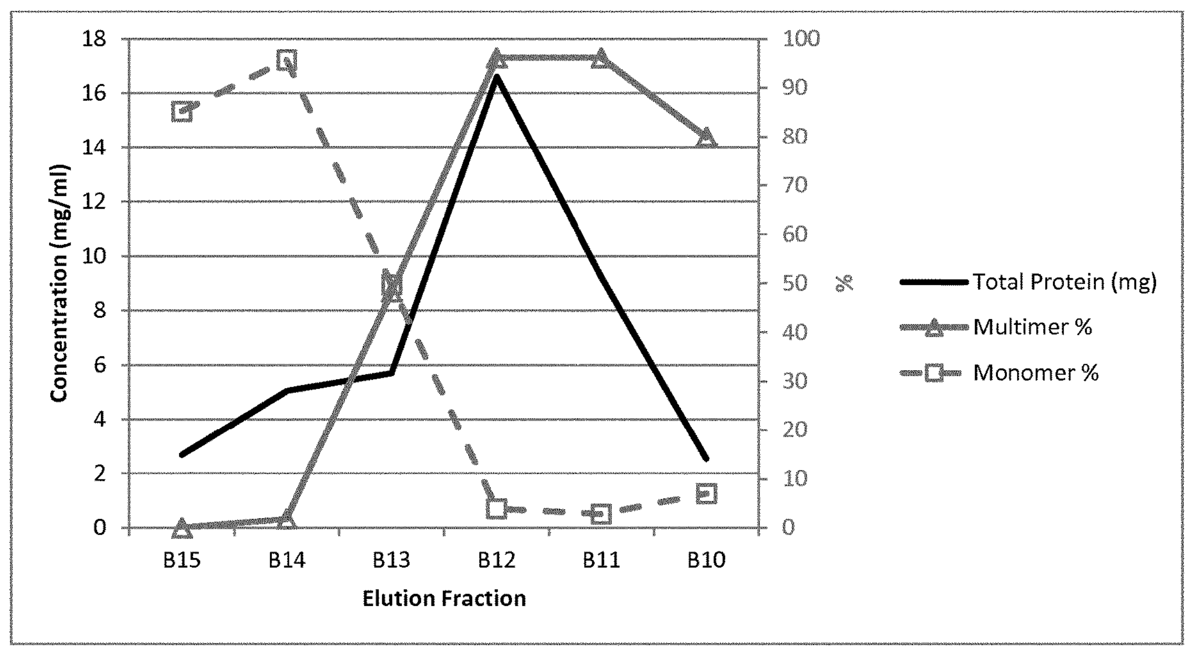
FIG. 9 shows a SEC-UPLC analysis of the fractions recovered from the protein A chromatography of A26Fab-645dsFv via gradient elution as described in Example 4, showing the amount of total protein, monomeric and multimeric A26Fab-645dsFv.

During elution from the Amsphere protein A chromatography column, two peaks were observed across the pH gradient, see FIG. 9. Elevated levels of monomer were observed in the first peak compared to elevated levels of multimeric species in the second peak, see table 5 and FIG. 9.

A26Fab-645dsFv lacks an Fc therefore binding to Amsphere Protein-A was due to the human VH3 variable framework subclass of the V-regions. It is proposed that the increased binding of the multimeric species was due to the increased avidity of these molecules for protein-A. Multimeric species have more VH3 regions and therefore bind stronger to the Protein-A resin requiring a lower pH for elution.

TABLE 5

SEC Analysis of fractions from Amsphere Protein-A Purification of A26Fab-645dsFv via a pH gradient elution

| Fraction | Volume (ml) | Conc (mg/ml) | Protein (mg) | HMWS (%) | Monomer (%) |
|---|---|---|---|---|---|
| B15 | 5 | 0.54 | 2.68 | 0.0 | 85.2 |
| B14 | 5 | 1.01 | 5.05 | 1.8 | 95.7 |
| B13 | 5 | 1.14 | 5.7 | 48.2 | 49.7 |
| B12 | 5 | 3.32 | 16.61 | 96.1 | 3.9 |
| B11 | 5 | 1.85 | 9.235 | 96.1 | 2.8 |
| B10 | 5 | 0.51 | 2.535 | 79.9 | 7.0 |

Example 5

Protein-A (NovaSep Absolute) Purification of A26Fab-645dsFv via a Gradient Elution CHO Expression and Clarification of A26Fab-645dsFv The construct which binds human OX40 and serum albumin was expressed in a stable dihydrofolate reductase (DHFR) deficient Chinese Hamster Ovary cell line (CHO DG44). Cells were transfected by electroporation using a Nuclefector (Lonza) following the manufactures instructions with a plasmid vector containing both the gene for DHFR as a selectable marker and the genes encoding the product. Transfected cells were selected in medium lacking hypoxanthine and thymidine, and in the presence of the DHFR inhibitor methotrexate. Cultures were maintained in shaken flasks culture in batch mode and harvested after 14 days.

Clarification of the cell culture supernatant was carried out via centrifugation (4000×g for 60 minutes at room temperature) followed by depth and sterile filtration.

Protein-A Purification (NovaSep Absolute) of A26Fab-645dsFv via a pH Gradient Elution The clarified supernatant was applied to the NovaSep Absolute protein A chromatography column, (5 ml column volume with 10 cm bed height) and was equilibrated in Delbeccos Phosphate Buffered Saline (PBS) pH 7.4. The column was first washed with PBS to remove unbound material, and bound material was subsequently eluted with a pH gradient, pH 6.0 to pH 3.0. Eluted material was fractionated and analysed via SEC-UPLC using Acquity UPLC BEH450 SEC 2.5 μm column. SEC-UPLC analysis was used to determine the % monomer and multimer present in each fraction. A26Fab-645dsFv monomer had a retention time around 2.2 minutes. Dimer, trimer, tetramer, and higher order structures all showed retention times below 2.2 minutes and were collectively termed multimeric species or higher molecular weight species (HMWS).

Figure 10:
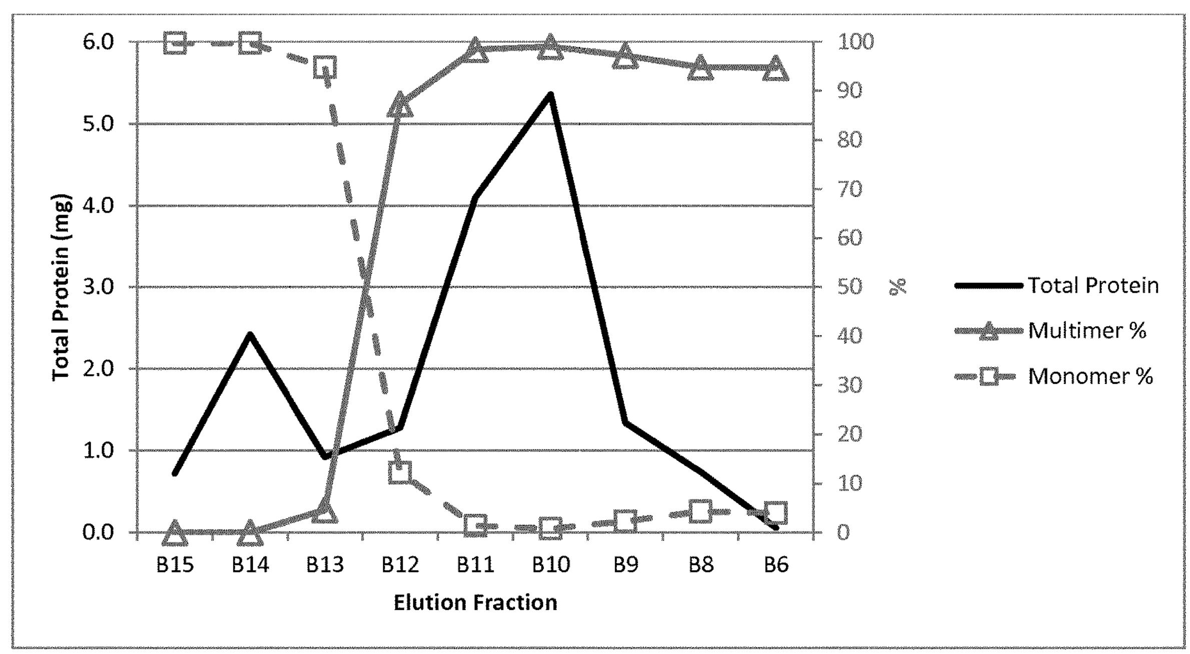
FIG. 10 shows a SEC-UPLC analysis of the fractions recovered from the protein A chromatography of A26Fab-645dsFv via gradient elution as described in Example 5, showing the amount of total protein, monomeric and multimeric A26Fab-645dsFv.

During elution from the NovaSep Absolute protein A chromatography column, two peaks were observed across the pH gradient, see FIG. 10. Elevated levels of monomer were observed in the first peak compared to elevated levels of multimeric species in the second peak, see table 6 and FIG. 10.

A26Fab-645dsFv lacks an Fc therefore binding to NovaSep Absolute Protein-A was due to the human VH3 variable framework subclass of the V-regions. It is proposed that the increased binding of the multimeric species was due to the increased avidity of these molecules for protein-A. Multimeric species have more VH3 regions and therefore bind stronger to the Protein-A resin requiring a lower pH for elution.

TABLE 6

SEC Analysis of fractions from NovaSep Absolute Protein-A Purification of A26Fab-645dsFv via a pH gradient elution

| Fraction | Volume (ml) | Conc (mg/ml) | Protein (mg) | HMWS (%) | Monomer (%) |
|---|---|---|---|---|---|
| B15 | 2 | 0.36 | 0.72 | 0 | 99.7 |
| B14 | 2 | 1.21 | 2.42 | 0 | 99.7 |
| B13 | 2 | 0.46 | 0.92 | 4.6 | 94.8 |
| B12 | 2 | 0.64 | 1.28 | 87.3 | 12.2 |
| B11 | 2 | 2.05 | 4.1 | 98.4 | 1.4 |
| B10 | 2 | 2.68 | 5.36 | 99 | 0.8 |
| B9 | 2 | 0.67 | 1.34 | 97.2 | 2.3 |
| B8 | 2 | 0.37 | 0.74 | 94.8 | 4.3 |
| B6 | 2 | 0.03 | 0.06 | 94.7 | 4 |

Example 6

Protein-A (AcroSep) Purification of A26Fab-645dsFv via a Gradient Elution

CHO Expression and Clarification of A26Fab-645dsFv

The construct which binds human OX40 and serum albumin was expressed in a stable dihyrofolate reductase (DHFR) deficient Chinese Hamster Ovary cell line (CHO DG44). Cells were transfected by electroporation using a Nuclefector (Lonza) following the manufactures instructions with a plasmid vector containing both the gene for DHFR as a selectable marker and the genes encoding the product. Transfected cells were selected in medium lacking hypoxanthine and thymidine, and in the presence of the DHFR inhibitor methotrexate. Cultures were maintained in shaken flasks culture in batch mode and harvested after 14 days.

Clarification of the cell culture supernatant was carried out via centrifugation (4000×g for 60 minutes at room temperature) followed by depth and sterile filtration.

Protein-A Purification (AcroSep) of A26Fab-645dsFv via a pH Gradient Elution

The clarified supernatant was applied to the AcroSep Protein A chromatography column, (1 ml column volume with 1.5 cm bed height) was equilibrated in Delbeccos Phosphate Buffered Saline (PBS) pH 7.4. The column was first washed with PBS to remove unbound material, and bound material was subsequently eluted with a pH gradient, pH 6.0 to pH 3.0. Eluted material was fractionated and analysed via SEC-UPLC using Acquity UPLC BEH450 SEC 2.5 μm column. SEC-HPLC analysis was used to determine the % monomer and multimer present in each fraction. A26Fab-645dsFv monomer had a retention time around 2.2 minutes. Dimer, trimer, tetramer, and higher order structures all showed retention times below 2.2 minutes and were collectively termed multimeric species or higher molecular weight species (HMWS).

Figure 11:
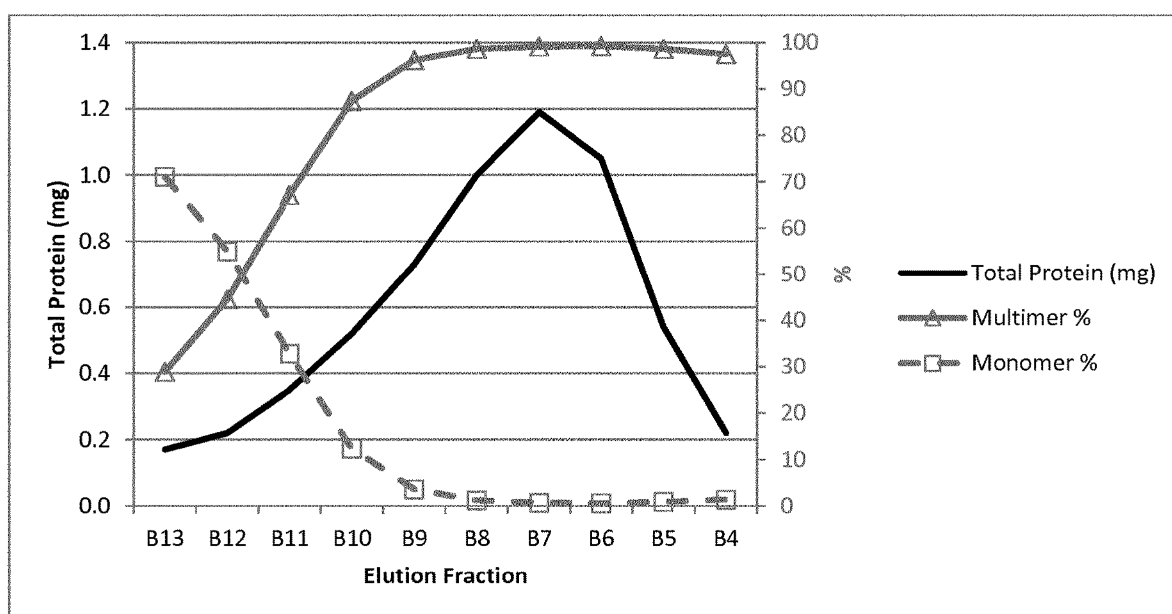
FIG. 11 shows a SEC-UPLC analysis of the fractions recovered from the protein A chromatography of A26Fab-645dsFv via gradient elution as described in Example 6, showing the amount of total protein, monomeric and multimeric A26Fab-645dsFv.

During elution from the AcroSep Protein A chromatography column, a single broad elution peak was observed across the pH gradient, see FIG. 11. The reduced resolution maybe due to the reduced bed height however elevated levels of monomer were still observed during the upward inflection of the peak compared to elevated levels of multimeric species during the downward inflection of the elution peak, see table 7 and FIG. 11.

A26Fab-645dsFv lacks an Fc therefore binding to AcroSep Absolute Protein-A was due to the human VH3 variable framework subclass of the V-regions. It is proposed that the increased binding of the multimeric species was due to the increased avidity of these molecules for protein-A. Multimeric species have more VH3 regions and therefore bind stronger to the Protein-A resin requiring a lower pH for elution.

TABLE 7

SEC Analysis of fractions from AcroSep Absolute Protein-A Purification of A26Fab-645dsFv via a pH gradient elution

| Fraction | Volume (ml) | Conc (mg/ml) | Protein (mg) | HMWS (%) | Monomer (%) |
|---|---|---|---|---|---|
| B13 | 1 | 0.17 | 0.17 | 28.9 | 71.1 |
| B12 | 1 | 0.22 | 0.22 | 44.6 | 55 |
| B11 | 1 | 0.35 | 0.35 | 67.1 | 32.8 |
| B10 | 1 | 0.52 | 0.52 | 87.4 | 12.4 |
| B9 | 1 | 0.73 | 0.73 | 96.2 | 3.6 |
| B8 | 1 | 1.00 | 1.00 | 98.6 | 1.2 |
| B7 | 1 | 1.19 | 1.19 | 99.1 | 0.7 |
| B6 | 1 | 1.05 | 1.05 | 99.2 | 0.6 |
| B5 | 1 | 0.54 | 0.54 | 98.6 | 0.9 |
| B4 | 1 | 0.22 | 0.22 | 97.5 | 1.4 |

Example 7

Protein-A Purification of TrYbe® via a pH Gradient Elution

Protein-A Purification of TrYbe® via a pH Gradient Elution

CHO Expression and Clarification of TrYbe®

A multispecific trivalent antibody molecule of the format Fab-2x dsscFv as described in WO 2015/197772 (TrYbe®) was expressed in a stable dihyrofolate reductase (DHFR) deficient Chinese Hamster Ovary cell line (CHO DG44). Cells were transfected using a Nuclefector (Lonza) following the manufactures instructions with a plasmid vector containing both the gene for DHFR as a selectable marker and the genes encoding the product. Transfected cells were selected in medium lacking hypoxanthine and thymidine, and in the presence of the DHFR inhibitor methotrexate. An expression was carried out in an in house proprietary fed batch process yielding a high cell number.

Clarification of the cell culture supernatant was carried out via centrifugation (4000×g for 60 minutes at room temperature) followed by depth and sterile filtration. Clarified cell culture supernatant was applied to a 5 ml HiTrap MabSelect (GE Healthcare) equilibrated in Delbeccos Phosphate Buffered Saline (PBS) pH7.4. The column was washed with PBS and bound material was eluted with a pH gradient, pH7.4 to pH 2.1, see FIG. 21. Eluted material was fractionated and analysed via G3000 SEC-HPLC and 4-20% Tris/Glycine SDS-PAGE (reduced & non-reduced). SEC-HPLC analysis was used to determine the % monomer and multimer. TrYbe® monomer has a retention time around 9.4 minutes. Dimer, trimer, tetramer, and higher order structures all have retention times <9.4 minutes and were collectively termed multimeric species or HMWS. For SEC-HPLC analysis chromatograms of fractions see FIG. 22.

Figure 21:
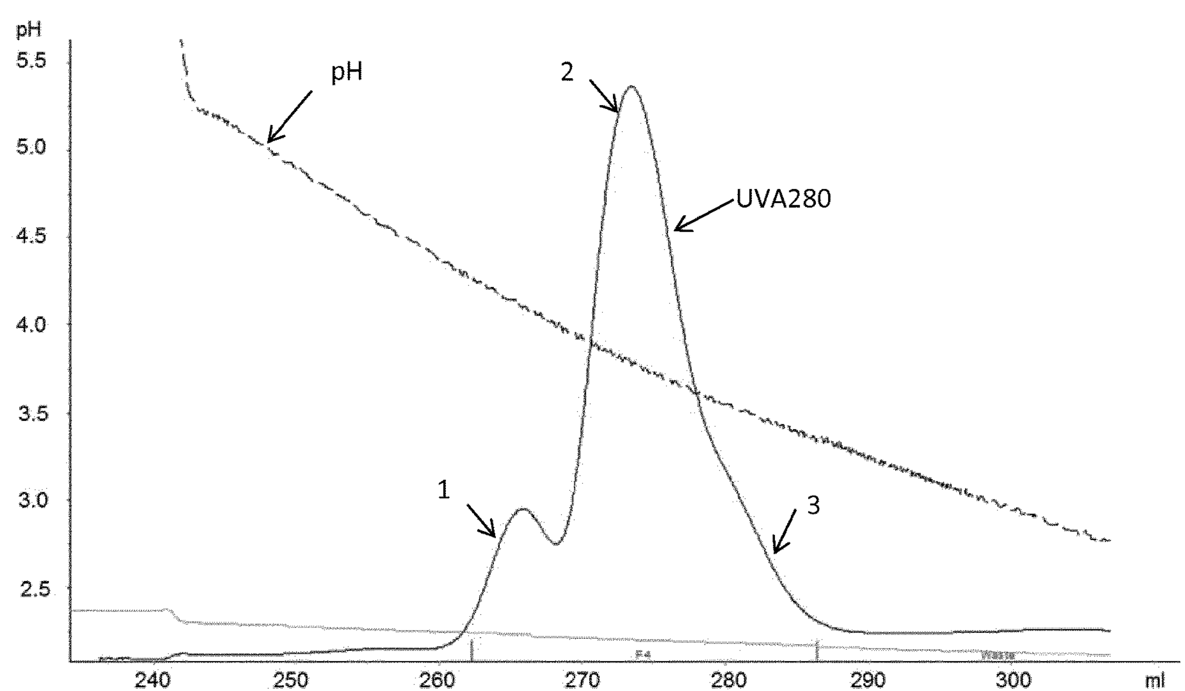
FIG. 21 shows a chromatogram showing the elution profile of TrYbe from a Protein A resin via a pH gradient elution.
Figure 22:
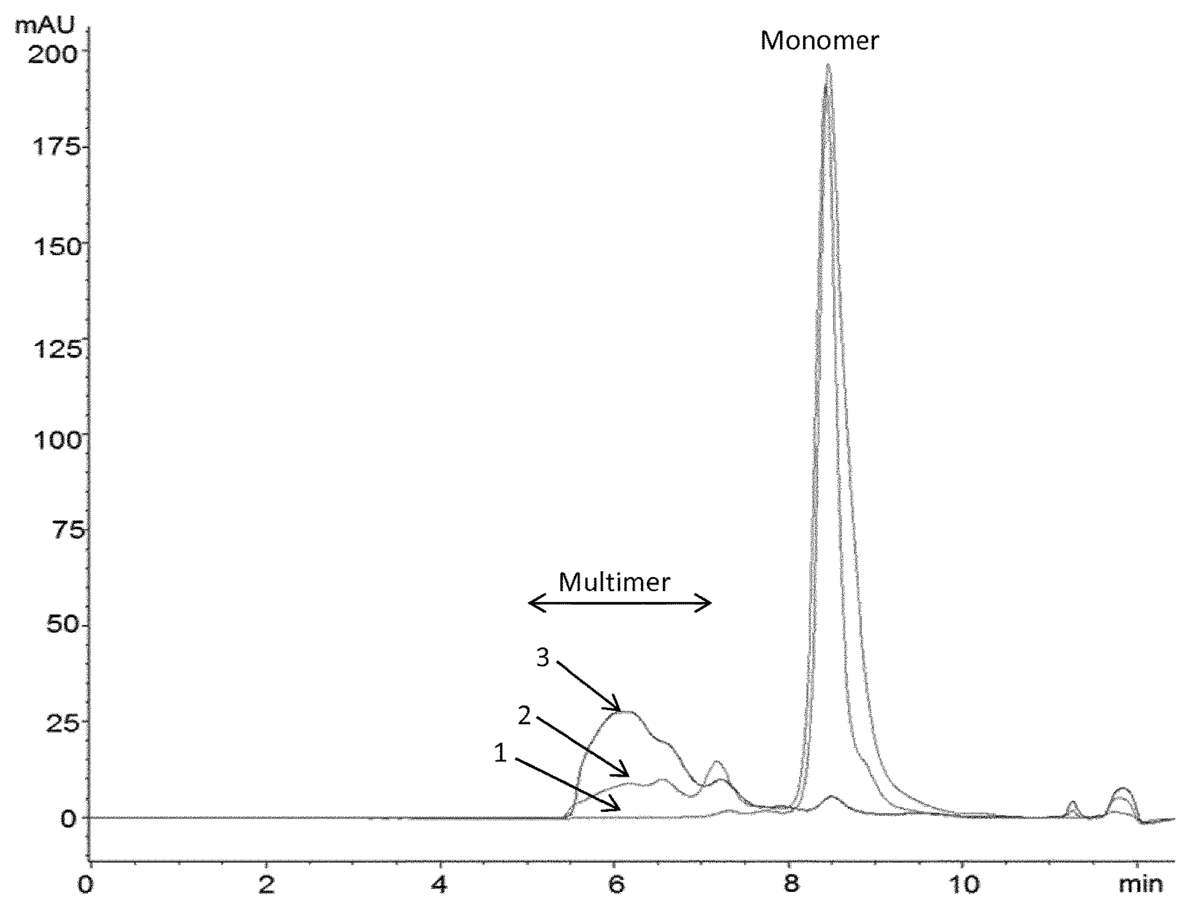
FIG. 22 shows a SEC-HPLC analysis of the fractions resulting from the protein A chromatography depicted in FIG. 21.
Figure 23:
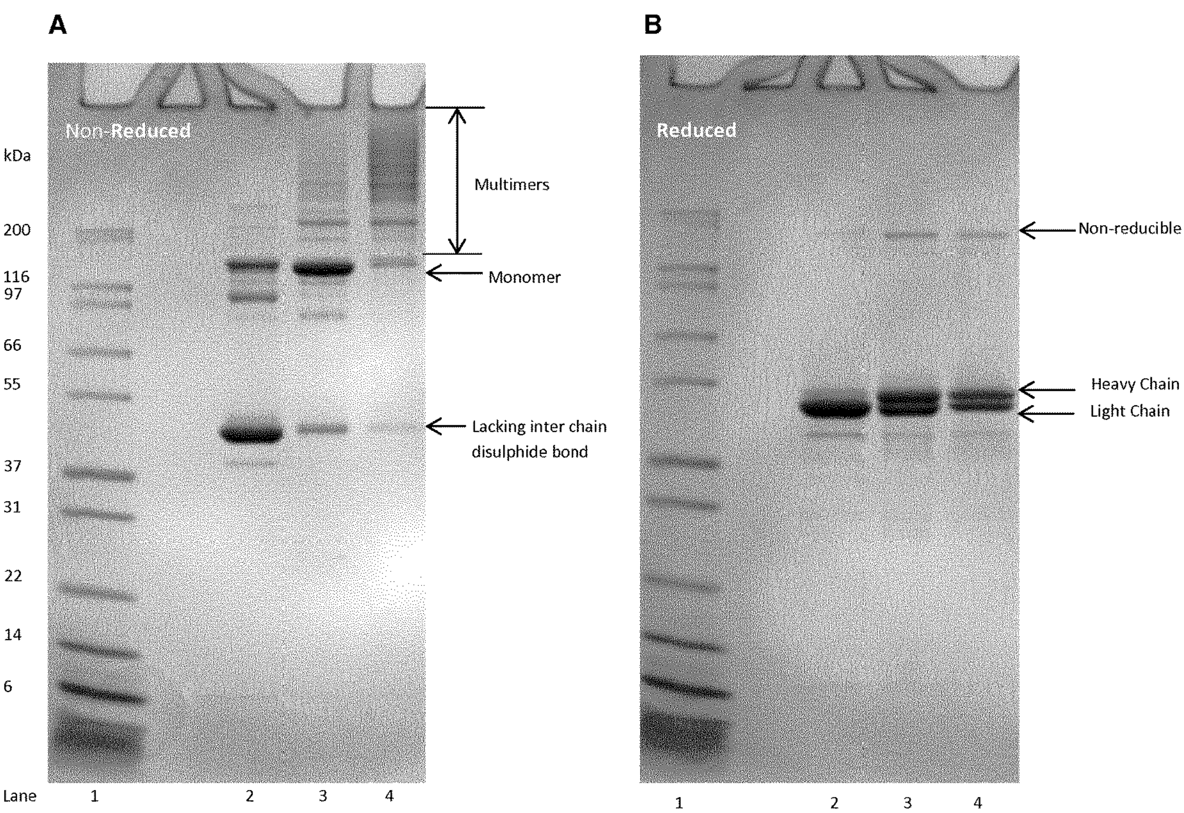
FIG. 23 shows a non-reducing (A) and reducing (B) SDS PAGE analysis of fractions recovered from the protein A chromatography of TrYbe via a pH gradient elution depicted in FIG. 21.

Across the pH gradient elution two peaks were observed along with a shoulder on the downward inflection, see FIG. 21. These 3 fractions were analysed by SDS-PAGE, see FIG. 23. Across the elution profile several bands were observed via non reducing SDS-PAGE. Monomer migrates between the 116-200 kDa molecular weight bands. All the bands which migrate above the monomer have been collectively termed multimeric or HMWS. A light chain related impurity lacking the inter chain disulphide species and non-disulphide bonded heavy and light chain migrate between the 37-55 kDa molecular weight markers. Fraction 1 (lane 2) was predominantly made up of monomer and light chain related species with little or no HMWS visible. The monomer is the main band in fraction 2 (lane 3). Although HMWS bands are visible the levels are significantly reduced to that seen in fraction 3 (lane 4). In the reduced gel all product related species are reduced down to heavy and light chain with a minor band of non-reducible material visible in lanes 3 and 4. Lane 2 confirms that fraction 1 was heavily enriched for the light chain related species.

Figure 24:
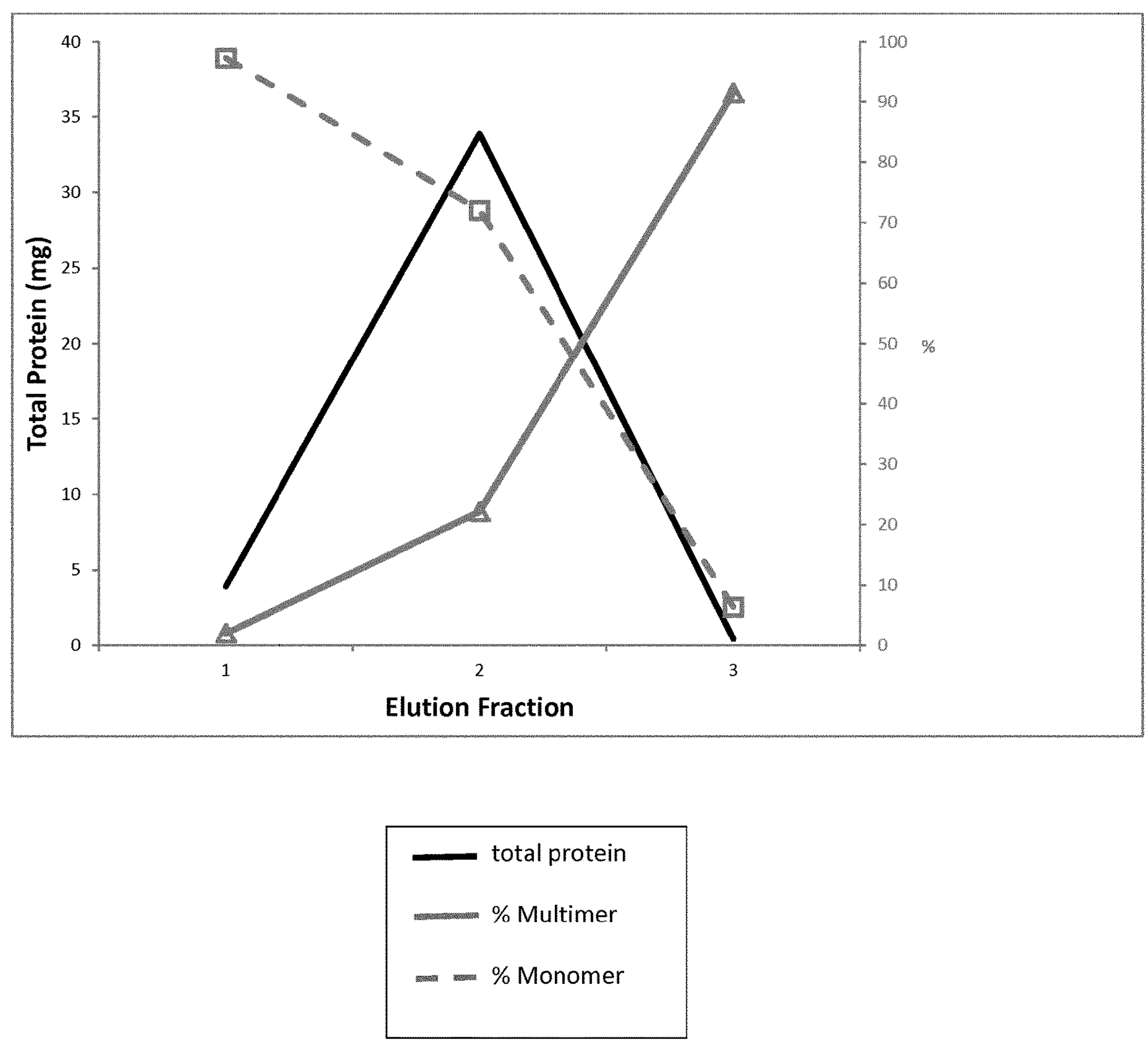
FIG. 24 the amount of total protein, monomeric and multimeric TrYbe present in each of the fractions resulting from the chromatography depicted in FIG. 21, as analysed by SEC-HPLC.

The first peak (1) was identified as a light chain related impurity by reducing SDS-PAGE and when analysed by SEC-HPLC contained 2% HMWS. The second peak (2) was identified as TrYbe® and contained 72% monomer and 22% HMWS, see table 8 and FIG. 24. The downward inflection on peak 2, fraction 3, was identified as TrYbe® and contained 6% monomer and 92% HMWS.

TrYbe® lacks an Fc therefore binding to Protein-A was due to the human VH3 variable framework subclass of the v-regions. It is proposed that the increased binding of the multimeric species was due to the increased avidity of these molecules for protein-A. Multimeric species have more VH3 regions and therefore bind stronger to the Protein-A resin requiring a lower pH for elution.

TABLE 8

G3000 SEC Analysis of Fractions from Protein-A Purification of TrYbe ® via a pH gradient elution

| Fraction | Protein (mg) | HMWS (%) | Monomer (%) |
|---|---|---|---|
| 1 | 3.9 | 2.0 | 97.3 |
| 2 | 33.9 | 22.1 | 72.0 |
| 3 | 0.4 | 91.5 | 6.4 |

Example 8

Protein-A Purification of BYbe via a pH Gradient Elution

CHO Expression and Clarification of BYbe

A Fab-scFv fusion protein (Bybe) was constructed essentially as described in Example 4 of WO2013/068571, using different variable region sequences. The construct was expressed in a stable dihyrofolate reductase (DHFR) deficient Chinese Hamster Ovary cell line (CHO DG44). Cells were transfected using a Nuclefector (Lonza) following the manufacturer instructions with a plasmid vector containing both the gene for DHFR as a selectable marker and the genes encoding the product. Transfected cells were selected in medium lacking hypoxanthine and thymidine, and in the presence of the DHFR inhibitor methotrexate. After culture up to shaker flask stage, growth and productivity were assessed and the 24 highest expressing clones were chosen for evaluation in a fed-batch shake flask process. A 3 L shake flask was inoculated with 1 L of culture at a starting density of $0.3\times10^6$ viable cells/mL and controlled at 36.8° C., in a 5% $CO_2$ atmosphere. Nutrient feeds were added from day 3 to 12 and glucose was added as a bolus addition when the concentration dropped below 5.8 g/L. The culture was harvested on day 14, via centrifugation at 4000×g for 60 min followed by 0.2 μm filtration.

Protein-A Purification of BYbe via a pH Gradient Elution

Clarified cell culture supernatant was applied to a 4.7 ml HiScreen MabSelect (GE Healthcare) column equilibrated in Sigma Phosphate Buffered Saline (PBS) pH7.4. The column was washed with PBS followed by 90% 0.2M Sodium Phosphate/10% citric acid, pH7.4 and bound material was eluted with a pH gradient of pH7.4 to pH 2.1, see FIG. 25. Eluted material was fractionated and analysed via G3000 SEC-HPLC and 4-20% Tris/Glycine SDS-PAGE (reduced & non-reduced). SEC-HPLC analysis was used to determine the % monomer and multimer. BYbe monomer has a retention time of around 9.6 minutes. Dimer, trimer, tetramer, and higher order structures all have retention times <9.6 minutes and were collectively termed multimeric species or HMWS. For SEC-HPLC analysis chromatograms of fractions see FIG. 26.

Figure 25:
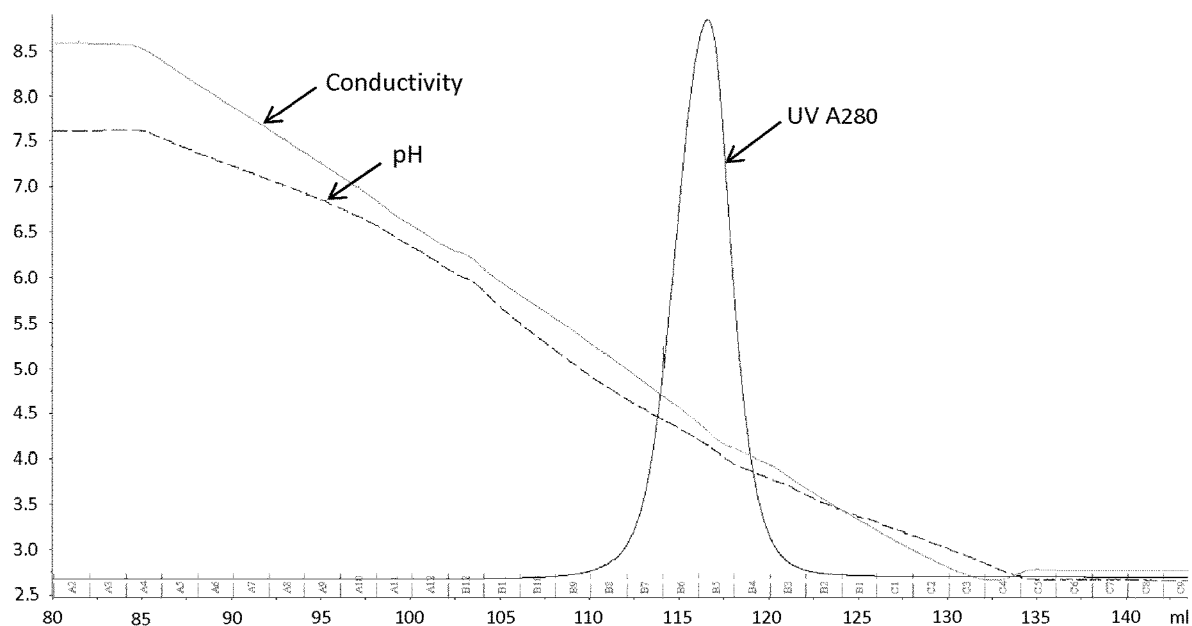
FIG. 25 shows a chromatogram showing the elution profile of BYbe from a Protein A resin via a pH gradient elution.
Figure 26:
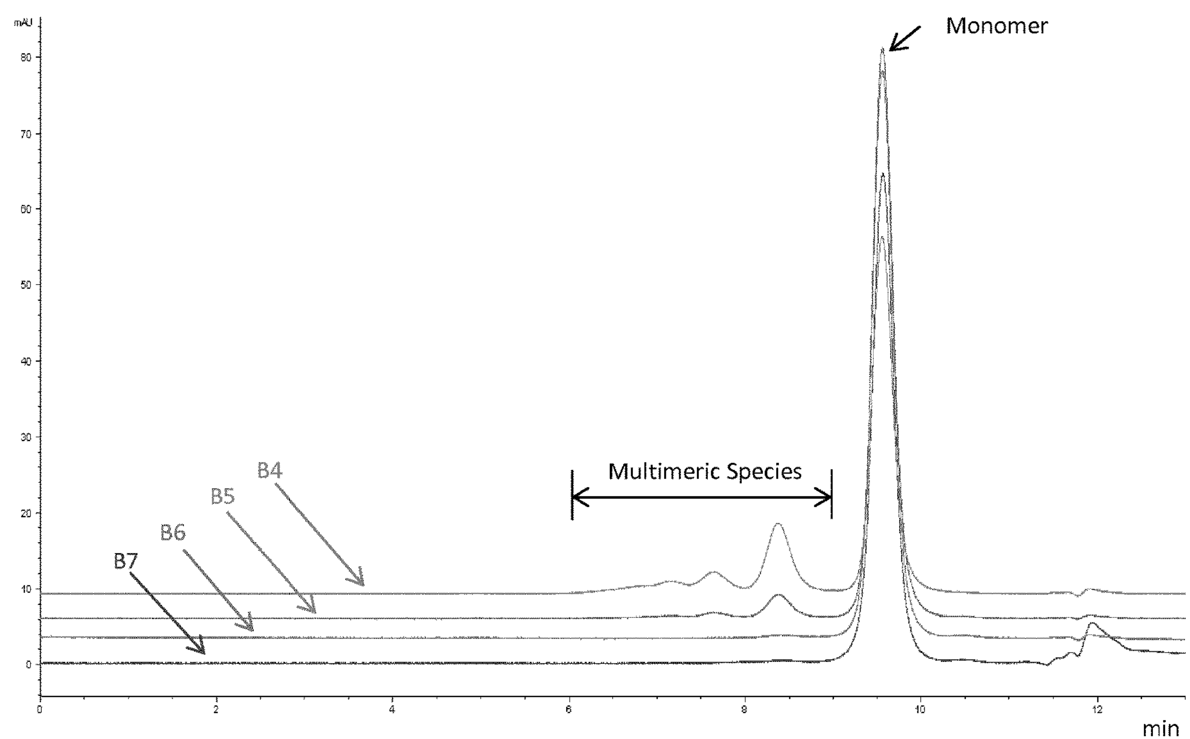
FIG. 26 shows a SEC-HPLC analysis of the fractions resulting from the protein A chromatography depicted in FIG. 25.

Across the pH gradient elution a single peak was observed, see FIG. 25. Elution peak fractions were analysed by SDS-PAGE, see FIG. 27. Across the elution profile several bands were observed via non reducing SDS-PAGE. Monomer migrates close to the 98 kDa molecular weight marker. All the bands which migrate above the monomer (between the 250 kDa and 98 kDa molecular weight markers) have been collectively termed multimeric or HMWS. Non-disulphide bonded heavy and light chain migrate between the 50-64 kDa and at the 30 kDa molecular weight markers respectively. Fractions B9-B6 (lanes 6-9) were predominantly made up of monomer with little or no HMWS visible. HMWS bands increase/become more intense in fractions B5-B3 (lanes 10-12) as the pH gradient becomes more acidic. In the reduced gel all product related species are reduced down to heavy and light chain.

Figure 28:
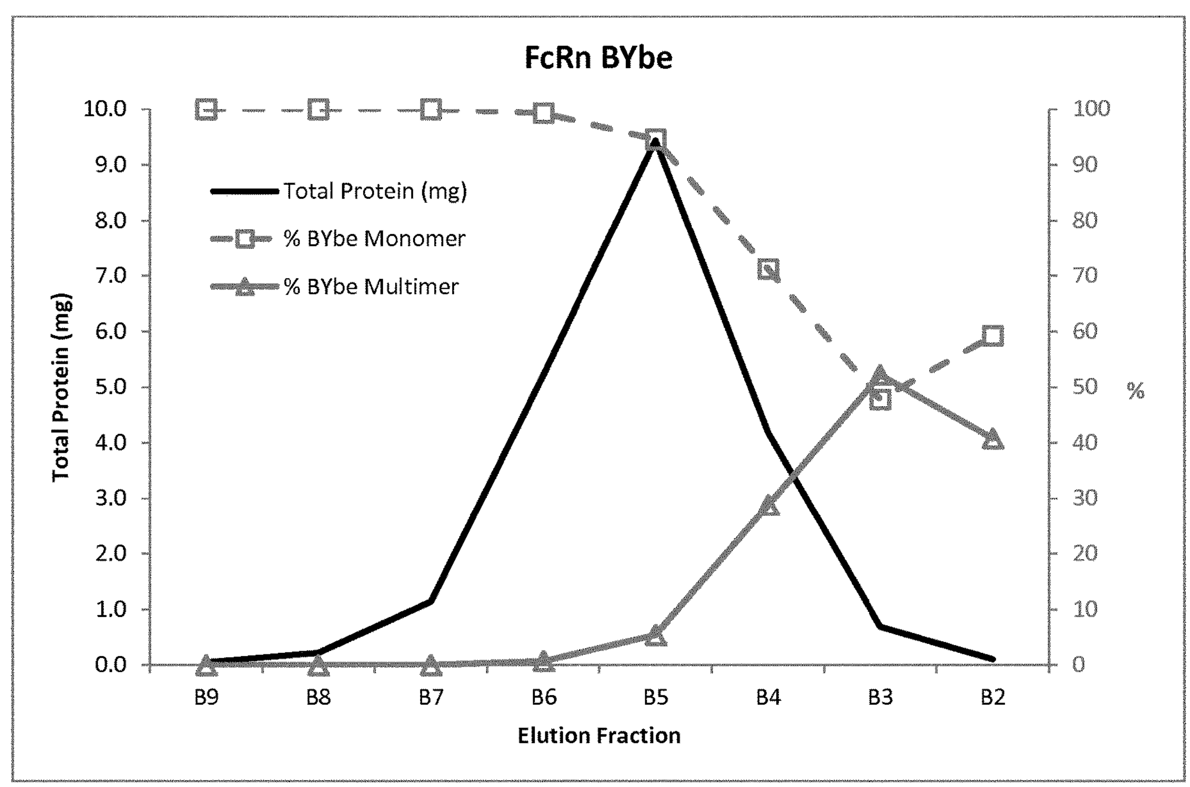
FIG. 28 the amount of total protein, monomeric and multimeric BYbe present in each of the fractions resulting from the chromatography depicted in FIG. 25, as analysed by SEC-HPLC.
Figure 29:
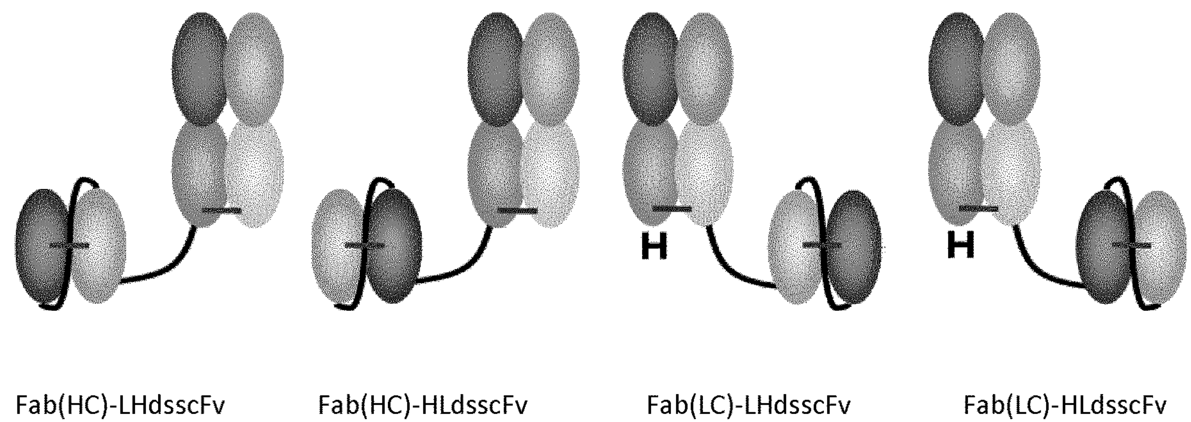
FIG. 29 shows a schematic of alternative monomeric Fab-scFv formats susceptible to purification according to the method of the invention.

The elution peak was identified as BYbe and overall contained 84% monomer and 16% HMWS, see table 9 and FIG. 28.

BYbe lacks an Fc therefore binding to Protein-A was due to the human VH3 variable framework subclass of the v-regions. It is proposed that the increased binding of the multimeric species was due to the increased avidity of these molecules for Protein-A. Multimeric species have more VH3 regions and therefore bind more strongly to the Protein-A resin requiring a lower pH for elution.

TABLE 9

G3000 SEC Analysis of Fractions from Protein-A Purification of BYbe via a pH gradient elution

| Fraction | Volume (ml) | Concentration (mg/ml) | Protein (mg) | HMWS (%) | Monomer (%) |
|---|---|---|---|---|---|
| B9 | 2.12 | 0.026 | 0.055 | 0.0 | 100.0 |
| B8 | 2.14 | 0.103 | 0.220 | 0.0 | 100.0 |
| B7 | 2.16 | 0.527 | 1.138 | 0.0 | 100.0 |
| B6 | 2.18 | 2.395 | 5.221 | 0.7 | 99.3 |
| B5 | 2.20 | 4.290 | 9.438 | 5.4 | 94.6 |
| B4 | 2.22 | 1.886 | 4.187 | 28.8 | 71.2 |
| B3 | 2.24 | 0.308 | 0.690 | 52.2 | 47.8 |
| B2 | 2.26 | 0.047 | 0.106 | 40.8 | 59.2 |
| | | Average: | | 16.0 | 84.0 |

The invention claimed is:

1. A method of separating a human VH3 domain-containing antibody in monomeric form from the antibody in multimeric form comprising:

a) applying a mixture comprising monomeric and multimeric forms of a human VH3 domain-containing antibody that comprises at least two human VH3 domains and does not contain an Fc region to a protein A chromatography material wherein said protein A comprises domain D and/or E, b) allowing binding of said antibody to protein A, c) applying an elution buffer that selectively disrupts binding of the antibody in monomeric form, d) recovering the resulting eluate (first eluate), said eluate comprising at least 80% human VH3 domain-containing antibody in monomeric form, and optionally e) applying a second elution buffer that disrupts binding of the antibody in multimeric form and recovering this second eluate.

2. A method of separating a human VH3 domain-containing antibody in monomeric form from the antibody in multimeric form comprising:

a) applying a mixture comprising monomeric and multimeric forms of a human VH3 domain-containing antibody that comprises at least two human VH3 domains and does not contain an Fc region to a protein A chromatography material wherein said protein A comprises domain D and/or E, b) allowing binding of the antibody in multimeric form, c) recovering the antibody in monomeric form in the flow-through said flow-through comprising at least 80% human VH3 domain-containing antibody in monomeric form, and optionally d) applying an elution buffer that selectively disrupts binding of the antibody in multimeric form, and e) recovering the eluate resulting from d).

3. The method according to claim 1, wherein the eluate recovered from the protein A chromatography is enriched in monomeric antibody over multimeric antibody with respect to the applied mixture by at least 90%.

4. The method according to claim 1, wherein said protein A is native recombinant protein A.

5. The method according to claim 1, wherein the VH3 domain containing antibody is selected from $F(ab')_2$, Fab-Fv, Fab-scFv, Fab-$(scFv)_2$, Fab-$(Fv)_2$, Fab-dsFv, diabodies, triabodies, and tetrabodies.

6. The method according to claim 1, wherein the VH3 domain-containing antibody specifically binds OX40.

7. The method according to claim 6, wherein said VH3 domain-containing antibody comprises:

heavy chain CDR1, CDR2 and CDR3 as defined in SEQ ID NO: 1, SEQ ID NO: 2 and SEQ ID NO: 3, respectively; and light chain CDR1, CDR2, and CDR3 as defined in SEQ ID NO: 4, SEQ ID NO: 5 and SEQ ID NO: 6, respectively.

8. The method according to claim 1, wherein the mixture comprising a human VH3 domain-containing antibody is produced by a prokaryotic host cell.

9. The method according to claim 2, wherein the mixture comprising a human VH3 domain-containing antibody is produced by a prokaryotic host cell.

10. The method according to claim 1, wherein the first eluate comprising recovered human VH3 domain containing antibody in monomeric form is applied to an anion exchange chromatography material and recovered in the flow through or an eluate.

11. The method according to claim 1, wherein the first eluate comprising recovered human VH3 domain containing antibody in monomeric form is applied to a cation exchange chromatography material and recovered in the flow through or an eluate.

12. The method according to claim 1, wherein the first eluate comprising recovered human VH3 domain containing antibody in monomeric form is applied to an anion exchange chromatography material and recovered in the flow through and the recovered flow through is applied to cation exchange chromatography material.

13. The method according to claim 12, wherein human VH3 domain containing antibody in monomeric form is bound to the cation exchange chromatography medium and eluted from the cation exchange chromatography material.

14. The method according to claim 1, wherein the first eluate comprising recovered human VH3 domain containing antibody in monomeric form is applied to a cation exchange chromatography material and recovered in an eluate and the eluate containing the recovered monomeric human VH3 domain is applied to an anion exchange chromatography material.

15. The method according to claim 12, wherein human VH3 domain containing antibody in monomeric form applied to the anion exchange chromatography material is recovered in flow-through from said anion exchange chromatography material.

* * * * *

SEQUENCE LISTING

```
<160> NUMBER OF SEQ ID NOS: 38

<210> SEQ ID NO 1
<211> LENGTH: 5
<212> TYPE: PRT
<213> ORGANISM: Artificial Sequence
```

<220> FEATURE:
<223> OTHER INFORMATION: CDR-H1

<400> SEQUENCE: 1

```
Asn Tyr Gly Ile His
1               5
```

<210> SEQ ID NO 2
<211> LENGTH: 17
<212> TYPE: PRT
<213> ORGANISM: Artificial Sequence
<220> FEATURE:
<223> OTHER INFORMATION: CDR-H2

<400> SEQUENCE: 2

```
Ser Ile Ser Pro Ser Gly Gly Leu Thr Tyr Tyr Arg Asp Ser Val Lys
1               5                   10                  15

Gly
```

<210> SEQ ID NO 3
<211> LENGTH: 8
<212> TYPE: PRT
<213> ORGANISM: Artificial Sequence
<220> FEATURE:
<223> OTHER INFORMATION: CDR-H3

<400> SEQUENCE: 3

```
Gly Gly Glu Gly Ile Phe Asp Tyr
1               5
```

<210> SEQ ID NO 4
<211> LENGTH: 11
<212> TYPE: PRT
<213> ORGANISM: Artificial Sequence
<220> FEATURE:
<223> OTHER INFORMATION: CDR-L1

<400> SEQUENCE: 4

```
Arg Ala Thr Gln Ser Ile Tyr Asn Ala Leu Ala
1               5                   10
```

<210> SEQ ID NO 5
<211> LENGTH: 7
<212> TYPE: PRT
<213> ORGANISM: Artificial Sequence
<220> FEATURE:
<223> OTHER INFORMATION: CDR-L2

<400> SEQUENCE: 5

```
Asn Ala Asn Thr Leu His Thr
1               5
```

<210> SEQ ID NO 6
<211> LENGTH: 9
<212> TYPE: PRT
<213> ORGANISM: Artificial Sequence
<220> FEATURE:
<223> OTHER INFORMATION: CDR-L3

<400> SEQUENCE: 6

```
Gln Gln Tyr Tyr Asp Tyr Pro Leu Thr
1               5
```

<210> SEQ ID NO 7
<211> LENGTH: 108
<212> TYPE: PRT

```
<213> ORGANISM: Artificial Sequence
<220> FEATURE:
<223> OTHER INFORMATION: LV region of Ab A26

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
    50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys Arg
            100                 105


<210> SEQ ID NO 8
<211> LENGTH: 117
<212> TYPE: PRT
<213> ORGANISM: Artificial Sequence
<220> FEATURE:
<223> OTHER INFORMATION: HV of Ab A26

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser
        115


<210> SEQ ID NO 9
<211> LENGTH: 214
<212> TYPE: PRT
<213> ORGANISM: Artificial Sequence
<220> FEATURE:
<223> OTHER INFORMATION: LC of Fab component

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45
```

```
Tyr Asn Ala Asn Thr Leu His Thr Gly Val Pro Ser Arg Phe Ser Ala
    50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 10
<211> LENGTH: 220
<212> TYPE: PRT
<213> ORGANISM: Artificial Sequence
<220> FEATURE:
<223> OTHER INFORMATION: HC of Fab component

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

```
Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220


<210> SEQ ID NO 11
<211> LENGTH: 121
<212> TYPE: PRT
<213> ORGANISM: Artificial Sequence
<220> FEATURE:
<223> OTHER INFORMATION: HC of anti-albumin Fv component

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120


<210> SEQ ID NO 12
<211> LENGTH: 112
<212> TYPE: PRT
<213> ORGANISM: Artificial Sequence
<220> FEATURE:
<223> OTHER INFORMATION: LC of anti-albumin Fv component

<400> SEQUENCE: 12

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Cys Gly Thr Lys Val Glu Ile Lys Arg Thr
            100                 105                 110


<210> SEQ ID NO 13
<211> LENGTH: 16
<212> TYPE: PRT
<213> ORGANISM: Artificial Sequence
<220> FEATURE:
<223> OTHER INFORMATION: LINKER 1
```

<400> SEQUENCE: 13

Ser Gly Gly Gly Gly Ser Gly Gly Gly Gly Thr Gly Gly Gly Gly Ser
1 5 10 15

<210> SEQ ID NO 14
<211> LENGTH: 15
<212> TYPE: PRT
<213> ORGANISM: Artificial Sequence
<220> FEATURE:
<223> OTHER INFORMATION: LINKER 2

<400> SEQUENCE: 14

Gly Gly Gly Gly Ser Gly Gly Gly Gly Ser Gly Gly Gly Gly Ser
1 5 10 15

<210> SEQ ID NO 15
<211> LENGTH: 357
<212> TYPE: PRT
<213> ORGANISM: Artificial Sequence
<220> FEATURE:
<223> OTHER INFORMATION: A26 H(g4s, g4t, g4s)-645ds Fv(Gh5)

<400> SEQUENCE: 15

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Asn Tyr
20 25 30

Gly Ile His Trp Ile Arg Gln Ala Pro Gly Lys Gly Leu Glu Trp Val
35 40 45

Ala Ser Ile Ser Pro Ser Gly Gly Leu Thr Tyr Tyr Arg Asp Ser Val
50 55 60

Lys Gly Arg Phe Thr Ile Ser Arg Asp Asp Ala Lys Asn Ser Pro Tyr
65 70 75 80

Leu Gln Met Asn Ser Leu Arg Ala Glu Asp Thr Ala Val Tyr Tyr Cys
85 90 95

Ala Thr Gly Gly Glu Gly Ile Phe Asp Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Lys Val Glu Pro Lys Ser Cys Ser Gly Gly Gly
210 215 220

Gly Ser Gly Gly Gly Gly Thr Gly Gly Gly Gly Ser Glu Val Gln Leu
225 230 235 240

Leu Glu Ser Gly Gly Gly Leu Val Gln Pro Gly Gly Ser Leu Arg Leu
245 250 255

Ser Cys Ala Val Ser Gly Ile Asp Leu Ser Asn Tyr Ala Ile Asn Trp
260 265 270

```
Val Arg Gln Ala Pro Gly Lys Cys Leu Glu Trp Ile Gly Ile Ile Trp
        275                 280                 285

Ala Ser Gly Thr Thr Phe Tyr Ala Thr Trp Ala Lys Gly Arg Phe Thr
    290                 295                 300

Ile Ser Arg Asp Asn Ser Lys Asn Thr Val Tyr Leu Gln Met Asn Ser
305                 310                 315                 320

Leu Arg Ala Glu Asp Thr Ala Val Tyr Tyr Cys Ala Arg Thr Val Pro
                325                 330                 335

Gly Tyr Ser Thr Ala Pro Tyr Phe Asp Leu Trp Gly Gln Gly Thr Leu
            340                 345                 350

Val Thr Val Ser Ser
        355


<210> SEQ ID NO 16
<211> LENGTH: 341
<212> TYPE: PRT
<213> ORGANISM: Artificial Sequence
<220> FEATURE:
<223> OTHER INFORMATION: A26 Fab Light-(3xG4S)-645dsFv(gL4)

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
    50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Gly Gly Gly Gly Ser Asp Ile Gln Met Thr Gln Ser Pro Ser Ser Val
225                 230                 235                 240

Ser Ala Ser Val Gly Asp Arg Val Thr Ile Thr Cys Gln Ser Ser Pro
                245                 250                 255

Ser Val Trp Ser Asn Phe Leu Ser Trp Tyr Gln Gln Lys Pro Gly Lys
            260                 265                 270
```

```
Ala Pro Lys Leu Leu Ile Tyr Glu Ala Ser Lys Leu Thr Ser Gly Val
        275                 280                 285

Pro Ser Arg Phe Ser Gly Ser Gly Ser Gly Thr Asp Phe Thr Leu Thr
    290                 295                 300

Ile Ser Ser Leu Gln Pro Glu Asp Phe Ala Thr Tyr Tyr Cys Gly Gly
305                 310                 315                 320

Gly Tyr Ser Ser Ile Ser Asp Thr Thr Phe Gly Cys Gly Thr Lys Val
                325                 330                 335

Glu Ile Lys Arg Thr
            340


<210> SEQ ID NO 17
<211> LENGTH: 119
<212> TYPE: PRT
<213> ORGANISM: Artificial Sequence
<220> FEATURE:
<223> OTHER INFORMATION: 645gH1 heavy chain variable domain

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Ser Thr Thr Val Tyr Leu Gln Met
65                  70                  75                  80

Asn Ser Leu Arg Ala Glu Asp Thr Ala Val Tyr Tyr Cys Ala Arg Thr
                85                  90                  95

Val Pro Gly Tyr Ser Thr Ala Pro Tyr Phe Asp Leu Trp Gly Gln Gly
            100                 105                 110

Thr Leu Val Thr Val Ser Ser
        115


<210> SEQ ID NO 18
<211> LENGTH: 110
<212> TYPE: PRT
<213> ORGANISM: Artificial Sequence
<220> FEATURE:
<223> OTHER INFORMATION: 645gL1 light chain variable domain

<400> SEQUENCE: 18

Asp Ile Val Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Lys
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Cys Gly Thr Lys Val Glu Ile Lys
```

100 105 110

<210> SEQ ID NO 19
<211> LENGTH: 355
<212> TYPE: PRT
<213> ORGANISM: Artificial Sequence
<220> FEATURE:
<223> OTHER INFORMATION: A26 Fab Heavy-( 3xG4S)-645dsFv(gH1)

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Ser Gly Gly Gly
    210                 215                 220

Gly Ser Gly Gly Gly Gly Ser Gly Gly Gly Gly Ser Glu Val Gln Leu
225                 230                 235                 240

Leu Glu Ser Gly Gly Gly Leu Val Gln Pro Gly Gly Ser Leu Arg Leu
                245                 250                 255

Ser Cys Ala Val Ser Gly Ile Asp Leu Ser Asn Tyr Ala Ile Asn Trp
            260                 265                 270

Val Arg Gln Ala Pro Gly Lys Cys Leu Glu Trp Ile Gly Ile Ile Trp
        275                 280                 285

Ala Ser Gly Thr Thr Phe Tyr Ala Thr Trp Ala Lys Gly Arg Phe Thr
    290                 295                 300

Ile Ser Arg Asp Ser Thr Thr Val Tyr Leu Gln Met Asn Ser Leu Arg
305                 310                 315                 320

Ala Glu Asp Thr Ala Val Tyr Tyr Cys Ala Arg Thr Val Pro Gly Tyr
                325                 330                 335

Ser Thr Ala Pro Tyr Phe Asp Leu Trp Gly Gln Gly Thr Leu Val Thr
            340                 345                 350

Val Ser Ser
```

355

<210> SEQ ID NO 20
<211> LENGTH: 340
<212> TYPE: PRT
<213> ORGANISM: Artificial Sequence
<220> FEATURE:
<223> OTHER INFORMATION: A26 Fab Light-(3xG4S)-645dsFv(gL1)

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
    50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ser Gly Gly Gly Gly Ser Gly Gly Gly Gly
    210                 215                 220

Ser Gly Gly Gly Gly Ser Asp Ile Val Met Thr Gln Ser Pro Ser Ser
225                 230                 235                 240

Val Ser Ala Ser Val Gly Asp Arg Val Thr Ile Thr Cys Gln Ser Ser
                245                 250                 255

Pro Ser Val Trp Ser Asn Phe Leu Ser Trp Tyr Gln Gln Lys Pro Gly
            260                 265                 270

Lys Ala Pro Lys Leu Leu Ile Tyr Glu Ala Ser Lys Leu Thr Ser Gly
        275                 280                 285

Val Pro Ser Arg Phe Lys Gly Ser Gly Ser Gly Thr Asp Phe Thr Leu
    290                 295                 300

Thr Ile Ser Ser Leu Gln Pro Glu Asp Phe Ala Thr Tyr Tyr Cys Gly
305                 310                 315                 320

Gly Gly Tyr Ser Ser Ile Ser Asp Thr Thr Phe Gly Cys Gly Thr Lys
                325                 330                 335

Val Glu Ile Lys
            340
```

```
<210> SEQ ID NO 21
<211> LENGTH: 1137
<212> TYPE: DNA
<213> ORGANISM: Artificial Sequence
<220> FEATURE:
<223> OTHER INFORMATION: Heavy chain A26-645(gH5) including E.coli OmpA
      leader

<400> SEQUENCE: 21

atgaagaaga ctgctatagc gatcgcagtg gcgctagctg gtttcgccac cgtggcgcaa     60

gctgaagttc agctggtcga gtctggaggc gggcttgtcc agcctggagg gagcctgcgt    120

ctctcttgtg cagcaagcgg tttcacgttc accaactacg gtatccactg gattcgtcag    180

gcaccaggta aaggtctgga atgggtagcc tctatctctc cgtctggtgg tctgacgtac    240

taccgtgact ctgtcaaagg tcgtttcacc atctctcgtg atgacgcgaa aaactctccg    300

tacctgcaaa tgaactctct gcgtgcagaa gataccgcag tgtactactg cgctactggt    360

ggtgaaggta tcttcgacta ctggggtcag ggtaccctgg taactgtctc gagcgcttct    420

acaaagggcc caagcgtttt cccactggct ccgtcctcta aatccacctc tggtggtacg    480

gctgcactgg gttgcctggt gaaagactac ttcccagaac cagttaccgt gtcttggaac    540

tctggtgcac tgacctctgg tgttcacacc tttccagcag ttctccagtc ttctggtctg    600

tactccctgt ctagcgtggt taccgttccg tcttcttctc tgggtactca gacctacatc    660

tgcaacgtca accacaaacc gtccaacacc aaggtcgaca aaaaagtcga gccgaaatcc    720

tgtagtggag gtgggggctc aggtggaggc gggaccggtg gaggtggcag cgaggttcaa    780

ctgcttgagt ctggaggagg cctagtccag cctggaggga gcctgcgtct ctcttgtgca    840

gtaagcggca tcgacctgag caattacgcc atcaactggg tgagacaagc tccggggaag    900

tgtttagaat ggatcggtat aatatgggcc agtgggacga ccttttatgc tacatgggcg    960

aaaggaaggt ttacaattag ccgggacaat agcaaaaaca ccgtgtatct ccaaatgaac   1020

tccttgcgag cagaggacac ggcggtgtac tattgtgctc gcactgtccc aggttatagc   1080

actgcaccct acttcgatct gtggggacaa gggaccctgg tgactgtttc aagttaa      1137


<210> SEQ ID NO 22
<211> LENGTH: 1074
<212> TYPE: DNA
<213> ORGANISM: Artificial Sequence
<220> FEATURE:
<223> OTHER INFORMATION: Heavy chain A26-645(gH5)

<400> SEQUENCE: 22

gaagttcagc tggtcgagtc tggaggcggg cttgtccagc ctggagggag cctgcgtctc     60

tcttgtgcag caagcggttt cacgttcacc aactacggta tccactggat tcgtcaggca    120

ccaggtaaag gtctggaatg ggtagcctct atctctccgt ctggtggtct gacgtactac    180

cgtgactctg tcaaaggtcg tttcaccatc tctcgtgatg acgcgaaaaa ctctccgtac    240

ctgcaaatga actctctgcg tgcagaagat accgcagtgt actactgcgc tactggtggt    300

gaaggtatct tcgactactg gggtcagggt accctggtaa ctgtctcgag cgcttctaca    360

aagggcccaa gcgttttccc actggctccg tcctctaaat ccacctctgg tggtacggct    420

gcactgggtt gcctggtgaa agactacttc ccagaaccag ttaccgtgtc ttggaactct    480

ggtgcactga cctctggtgt tcacaccttt ccagcagttc tccagtcttc tggtctgtac    540

tccctgtcta gcgtggttac cgttccgtct tcttctctgg gtactcagac ctacatctgc    600

aacgtcaacc acaaaccgtc caacaccaag gtcgacaaaa aagtcgagcc gaaatcctgt    660
```

```
agtggaggtg gggctcagg tggaggcggg accggtggag gtggcagcga ggttcaactg    720

cttgagtctg gaggaggcct agtccagcct ggagggagcc tgcgtctctc ttgtgcagta    780

agcggcatcg acctgagcaa ttacgccatc aactgggtga gacaagctcc ggggaagtgt    840

ttagaatgga tcggtataat atgggccagt gggacgacct tttatgctac atgggcgaaa    900

ggaaggttta caattagccg ggacaatagc aaaaacaccg tgtatctcca aatgaactcc    960

ttgcgagcag aggacacggc ggtgtactat tgtgctcgca ctgtcccagg ttatagcact   1020

gcaccctact tcgatctgtg gggacaaggg accctggtga ctgtttcaag ttaa         1074
```

<210> SEQ ID NO 23
<211> LENGTH: 1089
<212> TYPE: DNA
<213> ORGANISM: Artificial Sequence
<220> FEATURE:
<223> OTHER INFORMATION: Light chain A26-645(gL4) including E.coli OmpA leader

<400> SEQUENCE: 23

```
atgaaaaaga cagctatcgc aattgcagtg gcgttggctg gtttcgcgac cgttgcgcaa     60

gctgatatcc agatgaccca gagcccaagc agtctctccg ccagcgtagg cgatcgtgtg    120

actattacct gtcgtgcaac ccagagcatc tacaacgctc tggcttggta tcagcagaaa    180

ccgggtaaag cgccaaaact cctgatctac aacgcgaaca ctctgcatac tggtgttccg    240

tctcgtttct ctgcgtctgg ttctggtacg gactctactc tgaccatctc ctctctccag    300

ccggaagatt tcgcgaccta ctactgccag cagtactacg attacccact gacgtttggt    360

ggtggtacca aagttgagat caaacgtacg gttgcagctc catccgtctt catctttcca    420

ccgtctgacg aacagctcaa atctggtact gcttctgtcg tttgcctcct gaacaacttc    480

tatccgcgtg aagcgaaagt ccagtggaaa gtcgacaacg cactccagtc tggtaactct    540

caggaatctg tgaccgaaca ggactccaaa gactccacct actctctgtc tagcaccctg    600

actctgtcca aagcagacta cgagaaacac aaagtgtacg cttgcgaagt tacccatcag    660

ggtctgagct ctccggttac caaatccttt aatagagggg agtgtggtgg cggtggcagt    720

ggtggtggag gttccggagg tggcggttca gacatacaaa tgacccagag tccttcatcg    780

gtatccgcgt ccgttggcga tagggtgact attacatgtc aaagctctcc tagcgtctgg    840

agcaattttc tatcctggta tcaacagaaa ccggggaagg ctccaaaact tctgatttat    900

gaagcctcga aactcaccag tggagttccg tcaagattca gtggctctgg atcagggaca    960

gacttcacgt tgacaatcag ttcgctgcaa ccagaggact ttgcgaccta ctattgtggt   1020

ggaggttaca gtagcataag tgatacgaca tttgggtgcg gtactaaggt ggaaatcaaa   1080

cgtacctaa                                                           1089
```

<210> SEQ ID NO 24
<211> LENGTH: 1026
<212> TYPE: DNA
<213> ORGANISM: Artificial Sequence
<220> FEATURE:
<223> OTHER INFORMATION: Light chain A26-645(gL4)

<400> SEQUENCE: 24

```
gatatccaga tgacccagag cccaagcagt ctctccgcca gcgtaggcga tcgtgtgact     60

attacctgtc gtgcaaccca gagcatctac aacgctctgg cttggtatca gcagaaaccg    120

ggtaaagcgc caaaactcct gatctacaac gcgaacactc tgcatactgg tgttccgtct    180
```

```
cgtttctctg cgtctggttc tggtacggac tctactctga ccatctcctc tctccagccg    240

gaagatttcg cgacctacta ctgccagcag tactacgatt acccactgac gtttggtggt    300

ggtaccaaag ttgagatcaa acgtacggtt gcagctccat ccgtcttcat ctttccaccg    360

tctgacgaac agctcaaatc tggtactgct tctgtcgttt gcctcctgaa caacttctat    420

ccgcgtgaag cgaaagtcca gtggaaagtc gacaacgcac tccagtctgg taactctcag    480

gaatctgtga ccgaacagga ctccaaagac tccacctact ctctgtctag caccctgact    540

ctgtccaaag cagactacga gaaacacaaa gtgtacgctt gcgaagttac ccatcagggt    600

ctgagctctc cggttaccaa atcctttaat agaggggagt gtggtggcgg tggcagtggt    660

ggtggaggtt ccggaggtgg cggttcagac atacaaatga cccagagtcc ttcatcggta    720

tccgcgtccg ttggcgatag ggtgactatt acatgtcaaa gctctcctag cgtctggagc    780

aattttctat cctggtatca acagaaaccg ggaaaggctc caaaacttct gatttatgaa    840

gcctcgaaac tcaccagtgg agttccgtca agattcagtg gctctggatc agggacagac    900

ttcacgttga caatcagttc gctgcaacca gaggactttg cgacctacta ttgtggtgga    960

ggttacagta gcataagtga tacgacattt gggtgcggta ctaaggtgga aatcaaacgt   1020

acctaa                                                              1026
```

<210> SEQ ID NO 25
<211> LENGTH: 1131
<212> TYPE: DNA
<213> ORGANISM: Artificial Sequence
<220> FEATURE:
<223> OTHER INFORMATION: Heavy chain A26-645(gH5) including B72.3 leader sequence

<400> SEQUENCE: 25

```
atggaatggt cctgggtctt cctgtttttc ctttctgtca caaccggggt gcacagcgag     60

gtgcagctcg tcgagtctgg aggcgggctt gtccagcctg gagggagcct gcgtctctct    120

tgtgcagcaa gcggtttcac gttcaccaac tacggtatcc actggattcg tcaggcacca    180

ggtaaaggtc tggaatgggt agcctctatc tctccgtctg gtggtctgac gtactaccgt    240

gactctgtca aaggtcgttt caccatctct cgtgatgacg cgaaaaactc tccgtacctg    300

cagatgaact ctctgcgtgc agaagatacc gcagtgtact actgcgctac tggtggtgaa    360

ggtatcttcg actactgggg tcagggtacc ctggtaactg tctcaagcgc ttctacaaag    420

ggcccatcgg tcttcccct ggcaccctcc tccaagagca cctctggggg cacagcggcc    480

ctgggctgcc tggtcaagga ctacttcccc gaaccggtga cggtgtcgtg gaactcaggc    540

gccctgacca gcggcgtgca caccttcccg gctgtcctac agtcctctgg actctactcc    600

ctcagcagcg tggtgaccgt gccctccagc agcttgggca cccagaccta catctgcaac    660

gtgaatcaca agcccagcaa caccaaggtg gacaagaaag ttgagcccaa atcttgttcc    720

ggaggtggcg gttccggagg tggcggtacc ggtggcggtg gatccgaagt ccagctgctt    780

gaatccggag gcggactcgt gcagcccgga ggcagtcttc gcttgtcctg cgctgtatct    840

ggaatcgacc tgagcaatta cgccatcaac tgggtgagac aggcacctgg gaaatgcctc    900

gaatggatcg gcattatatg ggctagtggg acgacctttt atgctacatg ggcgaagggt    960

agattcacaa tctcacggga taatagtaag aacacagtgt acctgcagat gaactccctg   1020

cgagcagagg ataccgccgt ttactattgt gctcgcactg tcccaggtta tagcactgca   1080

ccctactttg atctgtgggg gcagggcact ctggtcaccg tctcgagttg a            1131
```

<210> SEQ ID NO 26
<211> LENGTH: 1074
<212> TYPE: DNA
<213> ORGANISM: Artificial Sequence
<220> FEATURE:
<223> OTHER INFORMATION: Heavy chain A26-645(gH5)

<400> SEQUENCE: 26

```
gaggtgcagc tcgtcgagtc tggaggcggg cttgtccagc ctggagggag cctgcgtctc     60

tcttgtgcag caagcggttt cacgttcacc aactacggta tccactggat tcgtcaggca    120

ccaggtaaag gtctggaatg ggtagcctct atctctccgt ctggtggtct gacgtactac    180

cgtgactctg tcaaaggtcg tttcaccatc tctcgtgatg acgcgaaaaa ctctccgtac    240

ctgcagatga actctctgcg tgcagaagat accgcagtgt actactgcgc tactggtggt    300

gaaggtatct tcgactactg gggtcagggt accctggtaa ctgtctcaag cgcttctaca    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc tggactctac    540

tccctcagca gcgtggtgac cgtgccctcc agcagcttgg gcacccagac ctacatctgc    600

aacgtgaatc acaagcccag caacaccaag gtggacaaga aagttgagcc caaatcttgt    660

tccggaggtg gcggttccgg aggtggcggt accggtggcg gtggatccga agtccagctg    720

cttgaatccg gaggcggact cgtgcagccc ggaggcagtc ttcgcttgtc ctgcgctgta    780

tctggaatcg acctgagcaa ttacgccatc aactgggtga gacaggcacc tgggaaatgc    840

ctcgaatgga tcggcattat atgggctagt gggacgacct tttatgctac atgggcgaag    900

ggtagattca caatctcacg ggataatagt aagaacacag tgtacctgca gatgaactcc    960

ctgcgagcag aggataccgc cgtttactat tgtgctcgca ctgtcccagg ttatagcact   1020

gcaccctact ttgatctgtg gggcagggc actctggtca ccgtctcgag ttga          1074
```

<210> SEQ ID NO 27
<211> LENGTH: 1086
<212> TYPE: DNA
<213> ORGANISM: Artificial Sequence
<220> FEATURE:
<223> OTHER INFORMATION: Light chain A26-645(gL4) including B72.3 leader sequence

<400> SEQUENCE: 27

```
atgtcagttc ccacacaggt gctgggcctg cttctgttgt ggctcaccga tgctaggtgt     60

gatatccaga tgacccagag tccaagcagt ctctccgcca gcgtaggcga tcgtgtgact    120

attacctgtc gtgcaaccca gagcatctac aacgctctgg cttggtatca gcagaaaccg    180

ggtaaagcgc caaaactcct gatctacaac gcgaacactc tgcataccgg tgttccgtct    240

cgtttctctg cgtctggttc tggtacggac tctactctga ccatctcctc tctgcagccg    300

gaagatttcg cgacctacta ctgccagcag tactacgatt acccactgac gtttggtggt    360

ggtaccaaag ttgagatcaa acgtacggtg gctgcaccat ctgtcttcat cttccccca    420

tctgatgagc agttgaagtc tggcactgcc tctgttgtgt gcctgctgaa taacttctac    480

cctagagagg ccaaagtcca gtggaaggtg gataacgccc ttcaatccgg aaactcccag    540

gagagtgtca ctgagcagga ctcaaaggac tccacctata gccttagcag cacactgaca    600

ctgagcaagg ctgactacga gaaacacaag gtctacgcct gcgaagtgac acatcaaggc    660
```

```
ctgagctcac ccgtgacaaa gagctttaac aggggagagt gtggtggagg tggctctggc    720

ggtggtggct ccggaggcgg aggaagcgac atccagatga cccagagccc ttcctctgta    780

agcgccagtg tcggagacag agtgactatt acctgccaaa gctccccttc agtctggtcc    840

aattttctat cctggtacca gcaaaagccc ggaaaggctc ctaaattgct gatctacgaa    900

gcaagcaaac tcaccagcgg cgtgcccagc aggttcagcg gcagtgggtc tggaactgac    960

tttaccctga caatctcctc actccagccc gaggacttcg ccacctatta ctgcggtgga   1020

ggttacagta gcataagtga tacgacattt ggatgcggca ctaaagtgga aatcaagcgt   1080

acctga                                                              1086
```

```
<210> SEQ ID NO 28
<211> LENGTH: 1026
<212> TYPE: DNA
<213> ORGANISM: Artificial Sequence
<220> FEATURE:
<223> OTHER INFORMATION: Light chain A26-645(gL4)

<400> SEQUENCE: 28

gatatccaga tgacccagag tccaagcagt ctctccgcca gcgtaggcga tcgtgtgact     60

attacctgtc gtgcaaccca gagcatctac aacgctctgg cttggtatca gcagaaaccg    120

ggtaaagcgc caaaactcct gatctacaac gcgaacactc tgcataccgg tgttccgtct    180

cgtttctctg cgtctggttc tggtacggac tctactctga ccatctcctc tctgcagccg    240

gaagatttcg cgacctacta ctgccagcag tactacgatt acccactgac gtttggtggt    300

ggtaccaaag ttgagatcaa acgtacggtg gctgcaccat ctgtcttcat cttcccccca    360

tctgatgagc agttgaagtc tggcactgcc tctgttgtgt gcctgctgaa taacttctac    420

cctagagagg ccaaagtcca gtggaaggtg gataacgccc ttcaatccgg aaactcccag    480

gagagtgtca ctgagcagga ctcaaaggac tccacctata gccttagcag cacactgaca    540

ctgagcaagg ctgactacga gaaacacaag gtctacgcct gcgaagtgac acatcaaggc    600

ctgagctcac ccgtgacaaa gagctttaac aggggagagt gtggtggagg tggctctggc    660

ggtggtggct ccggaggcgg aggaagcgac atccagatga cccagagccc ttcctctgta    720

agcgccagtg tcggagacag agtgactatt acctgccaaa gctccccttc agtctggtcc    780

aattttctat cctggtacca gcaaaagccc ggaaaggctc ctaaattgct gatctacgaa    840

gcaagcaaac tcaccagcgg cgtgcccagc aggttcagcg gcagtgggtc tggaactgac    900

tttaccctga caatctcctc actccagccc gaggacttcg ccacctatta ctgcggtgga    960

ggttacagta gcataagtga tacgacattt ggatgcggca ctaaagtgga aatcaagcgt   1020

acctga                                                              1026
```

```
<210> SEQ ID NO 29
<211> LENGTH: 121
<212> TYPE: PRT
<213> ORGANISM: Artificial Sequence
<220> FEATURE:
<223> OTHER INFORMATION: Heavy chain variable domain of anti-albumin
      antibody (no ds)

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30
```

```
Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120


<210> SEQ ID NO 30
<211> LENGTH: 121
<212> TYPE: PRT
<213> ORGANISM: Artificial Sequence
<220> FEATURE:
<223> OTHER INFORMATION: Heavy chain variable domain of anti-albumin
      antibody (ds)

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120


<210> SEQ ID NO 31
<211> LENGTH: 112
<212> TYPE: PRT
<213> ORGANISM: Artificial Sequence
<220> FEATURE:
<223> OTHER INFORMATION: Light chain variable domain of anti-albumin
      antibody (no ds)

<400> SEQUENCE: 31

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80
```

```
Pro Glu Asp Phe Ala Thr Tyr Tyr Cys Gly Gly Gly Tyr Ser Ser Ile
                85                  90                  95

Ser Asp Thr Thr Phe Gly Gly Gly Thr Lys Val Glu Ile Lys Arg Thr
            100                 105                 110


<210> SEQ ID NO 32
<211> LENGTH: 112
<212> TYPE: PRT
<213> ORGANISM: Artificial Sequence
<220> FEATURE:
<223> OTHER INFORMATION: Light chain variable domain of anti-albumin
      antibody (ds)

<400> SEQUENCE: 32

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Cys Gly Thr Lys Val Glu Ile Lys Arg Thr
            100                 105                 110


<210> SEQ ID NO 33
<211> LENGTH: 16
<212> TYPE: PRT
<213> ORGANISM: Artificial Sequence
<220> FEATURE:
<223> OTHER INFORMATION: LINKER 1

<400> SEQUENCE: 33

Ser Gly Gly Gly Gly Ser Gly Gly Gly Gly Thr Gly Gly Gly Gly Ser
1               5                   10                  15


<210> SEQ ID NO 34
<211> LENGTH: 15
<212> TYPE: PRT
<213> ORGANISM: Artificial Sequence
<220> FEATURE:
<223> OTHER INFORMATION: LINKER 2

<400> SEQUENCE: 34

Gly Gly Gly Gly Ser Gly Gly Gly Gly Ser Gly Gly Gly Gly Ser
1               5                   10                  15


<210> SEQ ID NO 35
<211> LENGTH: 789
<212> TYPE: PRT
<213> ORGANISM: Artificial Sequence
<220> FEATURE:
<223> OTHER INFORMATION: 645 gH5gL4 specific to albumin

<400> SEQUENCE: 35

Gly Ala Gly Gly Thr Thr Cys Ala Gly Cys Thr Gly Cys Thr Gly Gly
1               5                   10                  15

Ala Gly Thr Cys Thr Gly Gly Ala Gly Gly Cys Gly Gly Gly Cys Thr
```

```
            20                  25                  30

Thr Gly Thr Cys Cys Ala Gly Cys Cys Thr Gly Gly Ala Gly Gly Gly
        35                  40                  45

Ala Gly Cys Cys Thr Gly Cys Gly Thr Cys Thr Cys Thr Cys Thr Thr
    50                  55                  60

Gly Thr Gly Cys Ala Gly Thr Ala Ala Gly Cys Gly Gly Cys Ala Thr
65                  70                  75                  80

Cys Gly Ala Cys Cys Thr Gly Thr Cys Cys Ala Ala Cys Thr Ala Cys
                85                  90                  95

Gly Cys Gly Ala Thr Thr Ala Ala Cys Thr Gly Gly Gly Thr Ala Cys
            100                 105                 110

Gly Thr Cys Ala Gly Gly Cys Ala Cys Cys Gly Gly Gly Thr Ala Ala
        115                 120                 125

Ala Gly Gly Thr Cys Thr Gly Gly Ala Ala Thr Gly Gly Ala Thr Cys
    130                 135                 140

Gly Gly Cys Ala Thr Cys Ala Thr Cys Thr Gly Gly Gly Cys Cys Thr
145                 150                 155                 160

Cys Thr Gly Gly Thr Ala Cys Gly Ala Cys Cys Thr Thr Cys Thr Ala
                165                 170                 175

Cys Gly Cys Thr Ala Cys Thr Thr Gly Gly Gly Cys Cys Ala Ala Ala
            180                 185                 190

Gly Gly Thr Cys Gly Thr Thr Thr Cys Ala Cys Cys Ala Thr Cys Thr
        195                 200                 205

Cys Cys Cys Gly Thr Gly Ala Cys Ala Ala Cys Thr Cys Thr Ala Ala
    210                 215                 220

Ala Ala Ala Cys Ala Cys Cys Gly Thr Gly Thr Ala Cys Cys Thr Gly
225                 230                 235                 240

Cys Ala Gly Ala Thr Gly Ala Ala Cys Thr Cys Thr Cys Thr Gly Cys
                245                 250                 255

Gly Thr Gly Cys Gly Gly Ala Ala Gly Ala Cys Ala Cys Thr Gly Cys
            260                 265                 270

Gly Gly Thr Thr Thr Ala Cys Thr Ala Thr Thr Gly Cys Gly Cys Gly
        275                 280                 285

Cys Gly Thr Ala Cys Cys Gly Thr Thr Cys Cys Gly Gly Gly Cys Thr
    290                 295                 300

Ala Thr Thr Cys Thr Ala Cys Thr Gly Cys Ala Cys Cys Gly Thr Ala
305                 310                 315                 320

Cys Thr Thr Cys Gly Ala Cys Cys Thr Gly Thr Gly Gly Gly Gly Thr
                325                 330                 335

Cys Ala Gly Gly Gly Thr Ala Cys Thr Cys Thr Gly Gly Thr Thr Ala
            340                 345                 350

Cys Cys Gly Thr Cys Thr Cys Gly Ala Gly Thr Gly Gly Ala Gly Gly
        355                 360                 365

Thr Gly Gly Cys Gly Gly Thr Thr Cys Thr Gly Gly Cys Gly Gly Thr
    370                 375                 380

Gly Gly Cys Gly Gly Thr Thr Cys Cys Gly Gly Thr Gly Gly Cys Gly
385                 390                 395                 400

Gly Thr Gly Gly Ala Thr Cys Gly Gly Gly Ala Gly Gly Thr Gly Gly
                405                 410                 415

Cys Gly Gly Thr Thr Cys Thr Gly Ala Thr Ala Thr Cys Cys Ala Gly
            420                 425                 430

Ala Thr Gly Ala Cys Cys Cys Ala Gly Ala Gly Thr Cys Cys Ala Ala
        435                 440                 445
```

Gly Cys Ala Gly Thr Gly Thr Thr Thr Cys Cys Gly Cys Cys Ala Gly
450 455 460

Cys Gly Thr Ala Gly Gly Cys Gly Ala Thr Cys Gly Thr Gly Thr Gly
465 470 475 480

Ala Cys Thr Ala Thr Thr Ala Cys Cys Thr Gly Thr Cys Ala Gly Thr
485 490 495

Cys Cys Thr Cys Thr Cys Cys Gly Ala Gly Cys Gly Thr Thr Thr Gly
500 505 510

Gly Thr Cys Cys Ala Ala Cys Thr Thr Cys Cys Thr Gly Ala Gly Cys
515 520 525

Thr Gly Gly Thr Ala Cys Cys Ala Gly Cys Ala Gly Ala Ala Ala Cys
530 535 540

Cys Gly Gly Gly Thr Ala Ala Ala Gly Cys Cys Cys Cys Gly Ala Ala
545 550 555 560

Ala Cys Thr Gly Cys Thr Gly Ala Thr Cys Thr Ala Cys Gly Ala Gly
565 570 575

Gly Cys Gly Thr Cys Thr Ala Ala Ala Cys Thr Gly Ala Cys Cys Thr
580 585 590

Cys Thr Gly Gly Thr Gly Thr Ala Cys Cys Gly Thr Cys Cys Cys Gly
595 600 605

Thr Thr Thr Cys Thr Cys Thr Gly Gly Cys Thr Cys Thr Gly Gly Cys
610 615 620

Thr Cys Thr Gly Gly Thr Ala Cys Gly Gly Ala Cys Thr Thr Cys Ala
625 630 635 640

Cys Thr Cys Thr Gly Ala Cys Cys Ala Thr Cys Thr Cys Cys Thr Cys
645 650 655

Thr Cys Thr Gly Cys Ala Gly Cys Cys Gly Gly Ala Ala Gly Ala Cys
660 665 670

Thr Thr Thr Gly Cys Ala Ala Cys Gly Thr Ala Cys Thr Ala Cys Thr
675 680 685

Gly Cys Gly Gly Thr Gly Gly Thr Gly Gly Thr Thr Ala Cys Thr Cys
690 695 700

Thr Thr Cys Cys Ala Thr Cys Thr Cys Thr Gly Ala Cys Ala Cys Cys
705 710 715 720

Ala Cys Gly Thr Thr Cys Gly Gly Thr Gly Gly Ala Gly Gly Cys Ala
725 730 735

Cys Cys Ala Ala Ala Gly Thr Thr Gly Ala Ala Ala Thr Cys Ala Ala
740 745 750

Ala Cys Gly Thr Ala Cys Gly Cys Ala Thr Cys Ala Cys Cys Ala Thr
755 760 765

Cys Ala Cys Cys Ala Thr Cys Ala Cys Cys Ala Thr Cys Ala Cys Cys
770 775 780

Ala Thr Cys Ala Cys
785

<210> SEQ ID NO 36
<211> LENGTH: 263
<212> TYPE: PRT
<213> ORGANISM: Artificial Sequence
<220> FEATURE:
<223> OTHER INFORMATION: 645 gH5gL4 specific to albumin

<400> SEQUENCE: 36

Glu Val Gln Leu Leu Glu Ser Gly Gly Gly Leu Val Gln Pro Gly Gly
1 5 10 15

```
Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Val Ser Ala Ser Val Gly Asp Arg Val
145                 150                 155                 160

Thr Ile Thr Cys Gln Ser Ser Pro Ser Val Trp Ser Asn Phe Leu Ser
                165                 170                 175

Trp Tyr Gln Gln Lys Pro Gly Lys Ala Pro Lys Leu Leu Ile Tyr Glu
            180                 185                 190

Ala Ser Lys Leu Thr Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gly Gly Gly Tyr Ser Ser Ile Ser Asp Thr
225                 230                 235                 240

Thr Phe Gly Gly Gly Thr Lys Val Glu Ile Lys Arg Thr His His His
                245                 250                 255

His His His His His His His
            260


<210> SEQ ID NO 37
<211> LENGTH: 789
<212> TYPE: PRT
<213> ORGANISM: Artificial Sequence
<220> FEATURE:
<223> OTHER INFORMATION: 645 gH5gL4ds specific to albumin

<400> SEQUENCE: 37

Gly Ala Gly Gly Thr Thr Cys Ala Gly Cys Thr Gly Cys Thr Gly Gly
1               5                   10                  15

Ala Gly Thr Cys Thr Gly Gly Ala Gly Gly Cys Gly Gly Gly Cys Thr
            20                  25                  30

Thr Gly Thr Cys Cys Ala Gly Cys Cys Thr Gly Gly Ala Gly Gly Gly
        35                  40                  45

Ala Gly Cys Cys Thr Gly Cys Gly Thr Cys Thr Cys Thr Cys Thr Thr
    50                  55                  60

Gly Thr Gly Cys Ala Gly Thr Ala Ala Gly Cys Gly Gly Cys Ala Thr
65                  70                  75                  80

Cys Gly Ala Cys Cys Thr Gly Thr Cys Cys Ala Ala Cys Thr Ala Cys
                85                  90                  95

Gly Cys Gly Ala Thr Thr Ala Ala Cys Thr Gly Gly Gly Thr Ala Cys
            100                 105                 110
```

```
Gly Thr Cys Ala Gly Gly Cys Ala Cys Cys Gly Gly Gly Thr Ala Ala
        115                 120                 125

Ala Thr Gly Cys Cys Thr Gly Gly Ala Ala Thr Gly Gly Ala Thr Cys
    130                 135                 140

Gly Gly Cys Ala Thr Cys Ala Thr Cys Thr Gly Gly Gly Cys Cys Thr
145                 150                 155                 160

Cys Thr Gly Gly Thr Ala Cys Gly Ala Cys Cys Thr Thr Cys Thr Ala
                165                 170                 175

Cys Gly Cys Thr Ala Cys Thr Thr Gly Gly Gly Cys Cys Ala Ala Ala
            180                 185                 190

Gly Gly Thr Cys Gly Thr Thr Thr Cys Ala Cys Cys Ala Thr Cys Thr
        195                 200                 205

Cys Cys Cys Gly Thr Gly Ala Cys Ala Ala Cys Thr Cys Thr Ala Ala
    210                 215                 220

Ala Ala Ala Cys Ala Cys Cys Gly Thr Gly Thr Ala Cys Cys Thr Gly
225                 230                 235                 240

Cys Ala Gly Ala Thr Gly Ala Ala Cys Thr Cys Thr Cys Thr Gly Cys
                245                 250                 255

Gly Thr Gly Cys Gly Gly Ala Ala Gly Ala Cys Ala Cys Thr Gly Cys
            260                 265                 270

Gly Gly Thr Thr Thr Ala Cys Thr Ala Thr Thr Gly Cys Gly Cys Gly
        275                 280                 285

Cys Gly Thr Ala Cys Cys Gly Thr Thr Cys Cys Gly Gly Gly Cys Thr
    290                 295                 300

Ala Thr Thr Cys Thr Ala Cys Thr Gly Cys Ala Cys Cys Gly Thr Ala
305                 310                 315                 320

Cys Thr Thr Cys Gly Ala Cys Cys Thr Gly Thr Gly Gly Gly Gly Thr
                325                 330                 335

Cys Ala Gly Gly Gly Thr Ala Cys Thr Cys Thr Gly Gly Thr Thr Ala
            340                 345                 350

Cys Cys Gly Thr Cys Thr Cys Gly Ala Gly Thr Gly Gly Ala Gly Gly
        355                 360                 365

Thr Gly Gly Cys Gly Gly Thr Thr Cys Thr Gly Gly Cys Gly Gly Thr
    370                 375                 380

Gly Gly Cys Gly Gly Thr Thr Cys Cys Gly Gly Thr Gly Gly Cys Gly
385                 390                 395                 400

Gly Thr Gly Gly Ala Thr Cys Gly Gly Gly Ala Gly Gly Thr Gly Gly
                405                 410                 415

Cys Gly Gly Thr Thr Cys Thr Gly Ala Thr Ala Thr Cys Cys Ala Gly
            420                 425                 430

Ala Thr Gly Ala Cys Cys Cys Ala Gly Ala Gly Thr Cys Cys Ala Ala
        435                 440                 445

Gly Cys Ala Gly Thr Gly Thr Thr Thr Cys Cys Gly Cys Cys Ala Gly
    450                 455                 460

Cys Gly Thr Ala Gly Gly Cys Gly Ala Thr Cys Gly Thr Gly Thr Gly
465                 470                 475                 480

Ala Cys Thr Ala Thr Thr Ala Cys Cys Thr Gly Thr Cys Ala Gly Thr
                485                 490                 495

Cys Cys Thr Cys Thr Cys Cys Gly Ala Gly Cys Gly Thr Thr Thr Gly
            500                 505                 510

Gly Thr Cys Cys Ala Ala Cys Thr Thr Cys Cys Thr Gly Ala Gly Cys
        515                 520                 525
```

```
Thr Gly Gly Thr Ala Cys Cys Ala Gly Cys Ala Gly Ala Ala Ala Cys
    530                 535                 540

Cys Gly Gly Gly Thr Ala Ala Ala Gly Cys Cys Cys Cys Gly Ala Ala
545                 550                 555                 560

Ala Cys Thr Gly Cys Thr Gly Ala Thr Cys Thr Ala Cys Gly Ala Gly
                565                 570                 575

Gly Cys Gly Thr Cys Thr Ala Ala Ala Cys Thr Gly Ala Cys Cys Thr
            580                 585                 590

Cys Thr Gly Gly Thr Gly Thr Ala Cys Cys Gly Thr Cys Cys Cys Gly
        595                 600                 605

Thr Thr Thr Cys Thr Cys Thr Gly Gly Cys Thr Cys Thr Gly Gly Cys
    610                 615                 620

Thr Cys Thr Gly Gly Thr Ala Cys Gly Gly Ala Cys Thr Thr Cys Ala
625                 630                 635                 640

Cys Thr Cys Thr Gly Ala Cys Cys Ala Thr Cys Thr Cys Cys Thr Cys
                645                 650                 655

Thr Cys Thr Gly Cys Ala Gly Cys Cys Gly Gly Ala Ala Gly Ala Cys
            660                 665                 670

Thr Thr Thr Gly Cys Ala Ala Cys Gly Thr Ala Cys Thr Ala Cys Thr
        675                 680                 685

Gly Cys Gly Gly Thr Gly Gly Thr Gly Gly Thr Thr Ala Cys Thr Cys
    690                 695                 700

Thr Thr Cys Cys Ala Thr Cys Thr Cys Thr Gly Ala Cys Ala Cys Cys
705                 710                 715                 720

Ala Cys Gly Thr Thr Cys Gly Gly Thr Thr Gly Thr Gly Gly Cys Ala
                725                 730                 735

Cys Cys Ala Ala Ala Gly Thr Thr Gly Ala Ala Ala Thr Cys Ala Ala
            740                 745                 750

Ala Cys Gly Thr Ala Cys Gly Cys Ala Thr Cys Ala Cys Cys Ala Thr
        755                 760                 765

Cys Ala Cys Cys Ala Thr Cys Ala Cys Cys Ala Thr Cys Ala Cys Cys
    770                 775                 780

Ala Thr Cys Ala Cys
785
```

<210> SEQ ID NO 38
<211> LENGTH: 263
<212> TYPE: PRT
<213> ORGANISM: Artificial Sequence
<220> FEATURE:
<223> OTHER INFORMATION: 645 gH5gL4ds specific to albumin

<400> SEQUENCE: 38

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95
```

-continued

```
Arg Thr Val Pro Gly Tyr Ser Thr Ala Pro Tyr Phe Asp Leu Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Val Ser Ala Ser Val Gly Asp Arg Val
145                 150                 155                 160

Thr Ile Thr Cys Gln Ser Ser Pro Ser Val Trp Ser Asn Phe Leu Ser
                165                 170                 175

Trp Tyr Gln Gln Lys Pro Gly Lys Ala Pro Lys Leu Leu Ile Tyr Glu
            180                 185                 190

Ala Ser Lys Leu Thr Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gly Gly Gly Tyr Ser Ser Ile Ser Asp Thr
225                 230                 235                 240

Thr Phe Gly Cys Gly Thr Lys Val Glu Ile Lys Arg Thr His His His
                245                 250                 255

His His His His His His His
            260
```

UNITED STATES PATENT AND TRADEMARK OFFICE
CERTIFICATE OF CORRECTION

PATENT NO. : 10,927,164 B2
APPLICATION NO. : 15/566231
DATED : February 23, 2021
INVENTOR(S) : Sam Philip Heywood and Gavin Barry Wild Page 1 of 1

It is certified that error appears in the above-identified patent and that said Letters Patent is hereby corrected as shown below:

In the Specification

Column 10,
Line 4, "(ATCC 27,325 _____)" should read --(ATCC 27,325)--.

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*